United States Patent [19]
Wells et al.

[11] Patent Number: 5,880,066
[45] Date of Patent: *Mar. 9, 1999

[54] SAFENED HERBICIDAL SULFONAMIDE COMPOSITIONS

[75] Inventors: Barbara Heard Wells, St. Louis; Harrison Ross Hakes, Ballwin; David James Mayonado, Chesterfield; John Paul Chupp, Kirkwood, all of Mo.

[73] Assignee: Monsanto Company, St. Louis, Mo.

[ * ] Notice: The portion of the term of this patent subsequent to Oct. 26, 2013, has been disclaimed.

[21] Appl. No.: 800,471

[22] Filed: Dec. 6, 1991

Related U.S. Application Data

[63] Continuation-in-part of Ser. No. 626,128, Dec. 11, 1990, abandoned.

[51] Int. Cl.$^6$ .............................. A01N 25/32; A01N 43/90
[52] U.S. Cl. ..................... 504/103; 504/104; 504/105; 504/106; 504/107; 504/108; 504/109; 504/110; 504/111; 504/112; 504/241

[58] Field of Search .................... 71/88, 92; 504/104, 504/107

[56] References Cited

U.S. PATENT DOCUMENTS

| 4,818,273 | 4/1989 | Kleschick et al. .......................... 71/90 |
| 5,041,157 | 8/1991 | Seiler et al. ................................ 71/92 |

FOREIGN PATENT DOCUMENTS 304409   2/1989   European Pat. Off. .

*Primary Examiner*—S. Mark Clardy
*Attorney, Agent, or Firm*—Jon H. Beusen; Arnold, White & Durkee

[57] ABSTRACT

The disclosure herein relates to the use of a variety of antidotal compounds to safen crop plants from the phytotoxicity of azolopyrimidine sulfonamide herbicides.

13 Claims, No Drawings

SAFENED HERBICIDAL SULFONAMIDE COMPOSITIONS

RELATED APPLICATION

This application is a continuation-in-part of application Ser. No. 07/626,128, filed on Dec. 11, 1990, abandoned.

FIELD OF THE INVENTION

The field of the invention contemplated herein pertains to the safening of herbicidal sulfonamide compounds with antidotal or safener compounds. Particular herbicides involved are those generically characterized as azolopyrimidine sulfonamides with or without co-herbicidal compounds, e.g., α-haloacetamides, α-haloacetanilides, thiocarbamates, and/or other classes of herbicides.

BACKGROUND OF THE INVENTION

Many herbicides injure crop plants at herbicide application rates necessary to control weed growth. Accordingly, many herbicides cannot be used for controlling weeds in the presence of certain crops. Uncontrolled weed growth, however, results in lower crop yield and reduced crop quality inasmuch as weeds compete with crops for light, water and soil nutrients. Reduction of herbicidal injury to crops without an unacceptable corresponding reduction of herbicidal action on the weeds can be accomplished by use of crop protectants known as herbicide "antagonists", "antidotes" or "safeners".

Weed control for crops, especially corn crops, is one of the oldest and most highly developed areas in weed science. For a herbicide product to be accepted commercially for corn crops, such herbicide product must provide a relatively high level of control of both grassy and broadleaf weeds in corn, in addition to meeting several other criteria. For example, the herbicide should possess relatively high unit activity so that lower rates of herbicide application are feasible. Lower application rates are desirable in order to minimize exposure of the environment to the herbicide. At the same time, such herbicide must be selective in herbicidal effect so as not to injure the crops. Herbicidal selectivity can be enhanced by use of an appropriate antidote in combination with the herbicide. But identification of an antidote which safens a herbicide in crops is a highly complicated task. Whether a compound or class of compounds provides efficacious antidote or safening activity is not a theoretical determination but must be done empirically. Safening activity is determined empirically by observing the complex interaction of several biological and chemical factors, namely: the type of herbicide compound; the type of weed to be controlled; the type of crop to be protected from weed competition and herbicidal injury; and the antidote compound itself. Moreover, the herbicide and antidote must each possess chemical and physical properties enabling preparation of a stable formulation which is environmentally safe and easy to apply to the field.

Among the various classes of compounds found to be suitable for various herbicidal purposes are the α-haloacetanilides and thiocarbamates. The former herbicides, e.g., alachlor, acetochlor, metolachlor, etc., are excellent preemergence or early post emergence herbicides for controlling annual grasses and many broadleaved weeds in corn, peanuts, soybeans and other crops. The latter herbicides, exemplified by EPTC, butylate, etc., are also used as selective preemergence herbicides suitable for the control of many annual and perennial weeds and some broadleaved species in a variety of crops.

It is a common agronomic practice to use various antidotal compounds to reduce the phytotoxicity of some herbicides to various crops. For example, fluorazole (active ingredient in SCREEN® safener) is used as a seed dressing to protect sorghum seed from alachlor (active ingredient in LASSO® herbicide). Similarly, cyometrinil (active ingredient in CONCEP® safener) is a corn seed safener for use with metolachlor and oxabetrinil (active ingredient in CONCEP II safener) is used to safen sorghum seed from injury by metolachlor. The compound N,N-diallyl dichloroacetamide (common name dichlormid is used to safen corn from injury by the thiocarbamate 5-ethyl-N,N-dipropyl-thiocarbamate (active ingredient in ERADICANE® herbicide) and acetochlor (active ingredient in HARNESS® herbicide).

It is an object of this invention to provide compositions of azolopyrimidine sulfonamide herbicides in combination with antidotes therefor, optionally containing one or more co-herbicides, which compositions are useful to reduce injury to crops, especially corn, due to phytotoxicity of said herbicides.

SUMMARY OF THE INVENTION

The present invention relates to herbicidal compositions comprising azolopyrimidine sulfonamides and antidotal compounds therefor to reduce injury to various crops, particularly corn, from the phytotoxic effects of said herbicide when used alone or in combination with other compounds, particularly α-haloacetamides and α-haloacetanilides, as co-herbicides. Except where noted herein the term "α-haloacetamides" generically includes α-haloacetanilides as a subgroup (which require a phenyl or substituted phenyl attached to the acetamide nitrogen atom) and acetamides which have substituents other than a (un)substituted phenyl on the amide nitrogen.

In more particular, in a major aspect, this invention relates to a composition comprising:

(a) a herbicidal compound according to Formula I or an agriculturally-acceptable salt thereof:

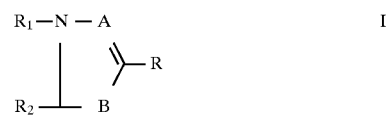

wherein

A and B are independently N or $CR_3$, provided that at least one of A or B is N;

R is $-N(R_4)SO_2R_5$ or $-SO_2N(R_6)R_7$;

$R_1$ is hydrogen, alkyl, alkenyl, alkynyl, acyl, acyloxy, cycloalkyl, cycloalkenyl, aryl, aralkyl, alkoxy, alkoxyalkyl, alkoxycarbonyl, aminocarbonyl, alkylsulfinyl, alkylsulfonyl or heterocyclic group or where not self inclusive any of these non-hydrogen radicals substituted with cyano, halogen, amino, mono- or di- $C_{1-4}$ alkylamino, $C_{1-6}$ alkyl, haloalkyl, alkylthio, alkoxy, alkoxyalkyl, alkoxycarbonyl, alkylthio, alkylsulphinyl or alkylsulfonyl;

$R_2$ is an $R_1$ member, halogen, cyano, amino, mono- or di- $C_{1-4}$ alkyl amino, pyrrolyl or pyrrolyl substituted with halogen, cyano, amino $C_{1-4}$ alkyl or alkoxy;

$R_1$ and $R_2$ may be combined to form a divalent group which together with the N and C atoms to which they are respectively attached form a heterocyclic ring fused with the azolo ring, said heterocyclic ring containing up to 10 ring members of which up to 4 are N, S and/or O atoms and having saturated and/or unsaturated bonds;

$R_3$ is an $R_2$ member or $NO_2$, $S(O)_nC_{1-4}$ alkyl, where n is an integer 0, 1, 2 or 3, $C(O)R_8$, phenyl, phenoxy, phenylthio, or these phenyl, phenoxy or phenylthio members substituted with from 1 to 4 halogen, CN, $CF_3$, $NO_2$ and/or $C_{1-4}$ alkyl or alkoxy members; $R_8$ is $C_{1-6}$ alkyl, haloalkyl, alkylthio, alkoxy, alkoxyalkyl, amino, mono- or di-$C_{1-4}$ alkylamino, phenyl or an $R_3$ phenyl-substituted member;

$R_4$ and $R_6$ are independently H or alkyl, acyl, alkenyl, alkenyloxy, alkenyloxycarbonyl, alkynyl, alkynyloxy, alkanoyl, alkoxy, haloalkoxy, haloalkylthio, alkoxyalkyl, alkoxycarbonyl, or alkoxythiocarbonyl, each having up to 10 carbon atoms; phenyl, benzyl, naphthylphenylthio, phenoxy, phenoxythio, phenoxycarbonyl, phenyl $S(O)_n$; phenyl $S(O)_nC_{1-4}$ alkyl; phenyl $S(O)_nC_m(K)_{2m}H$; phenyl $S(O)_nCK_m$, where n is 0, 1, 2 or 3, m is 1–3 and K is halogen; phenoxy- carbonyl, phenoxythio-carbonyl, aminocarbonyl, or where not self-inclusive said $R_4$ and $R_6$ members substituted with halogen, CN, $CF_3$, $NO_2$, OH and/or $C_{1-10}$ alkyl, haloalkyl, alkoxy, alkoxyalkoxy, hydroxyalkoxy, alkylthioalkoxy, alkoxycarbonyl, or polyalkoxycarbonyl, phenyl, halophenyl, benzyl, benzyloxy, phenoxyalkoxy and agriculturally-acceptable salts thereof when $R_4$ and $R_6$ are H and $R_5$ and $R_7$ are independently an aromatic hydrocarbon or heterocyclic radical having up to 10 ring members of which up to four may be N, O and/or S in the heterocyclic radical and said $R_5$ and $R_7$ members substituted with one or more $R_4$ members, 2-pyridyl, 2-pyridyloxy or 2-pyridylmethoxycarbonyl, dialkylaminoalkoxycarbonyl having up to 10 carbon atoms and the radical $C(O)ON=C(R_9)_2$, wherein $R_9$ is H, phenyl, phenylcarbonyl, benzyl, $C_{1-10}$ alkyl, alkoxy, mono- or di-$C_{1-6}$ alkylamino or -alkylaminocarbonyl, —$S(O)_nR_{10}$, where n is 0, 1, 2 or 3 and $R_{10}$ is $C_{1-6}$ alkyl, haloalkyl, mono- or di-$C_{1-4}$ alkylamino or alkylcarbonyl, said compound of Formula I being used alone or in admixture with other known herbicidal compounds as co-herbicides, preferably an α-haloacetamide of the formula

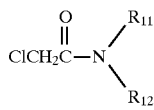

IV wherein $R_{11}$ and $R_{12}$ are independently hydrogen; $C_{1-8}$ alkyl, alkoxy, alkoxyalkyl, acylaminomethyl, acyl-lower alkyl-substituted aminomethyl; cycloalkyl, cycloalkylmethyl, mono- or polyunsaturated alkenyl, alkynyl, cycloalkenyl, cycloalkenylmethyl having up to 8 carbon atoms; phenyl; or $C_{4-10}$ heterocyclyl or heterocyclylmethyl containing from 1 to 4 ring hetero atoms selected independently from N, S or O; and wherein said $R_{11}$ and $R_{12}$ members may be substituted with alkyl, alkenyl, alkynyl, alkenyloxy, alkynyloxy, alkoxy, alkoxyalkyl, alkoxycarbomethyl or ethyl having up to 8 carbon atoms; nitro; halogen; cyano; amino or $C_{1-4}$ alkyl-substituted amino; and wherein $R_{11}$ and $R_{12}$ may be combined together with the N atom to which attached to form one of said heterocyclyl or substituted-heterocyclyl members and (b) an antidotally-effective amount of
 (i) a compound of the formula

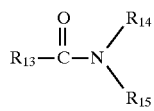

II wherein $R_{13}$ can be selected from the group consisting of haloalkyl; polyhaloalkyl; haloalkenyl; alkyl; alkenyl; cycloalkyl; cycloalkylalkyl; halogen; hydrogen; carboalkoxy; N-alkenylcarbamylalkyl; N-alkenylcarbamyl; N-alkyl-N-alkynylcarbamyl; N-alkyl-N-alkynylcarbamylalkyl; N-alkenylcarbamylalkoxyalkyl; N-alkyl-N-alkynylcarbamylalkoxyalkyl; alkynoxy; haloalkoxy; thiocyanatoalkyl; alkenylaminoalkyl; alkylcarboalkyl; cyanoalkyl; cyanatoalkyl; alkenylaminosulfonalkyl; alkylthioalkyl; haloalkylcarbonyloxyalkyl, alkoxycarboalkyl; haloalkenylcarbonyloxyalkyl; hydroxyhaloalkyloxyalkyl; hydroxyalkylcarboalkyoxyalkyl; hydroxyalkyl; alkoxysulfonoalkyl; furyl, thienyl; alkyldithiolenyl; thienalkyl; phenyl and substituted phenyl wherein said substituents can be selected from halogen, alkyl, haloalkyl, alkoxy, carbamyl, nitro, carboxylic acids and their salts, haloalkylcarbamyl; phenylalkyl; phenylhaloalkyl; phenylalkenyl; substituted phenylalkenyl wherein said substituents can be selected from halogen, alkyl, alkoxy, halophenoxy, phenylalkoxy; phenylalkylcarboxyalkyl; phenylcycloalkyl; halophenylalkenoxy; halothiophenylalkyl; halophenoxyalkyl; bicycloalkyl; alkenylcarbamylpyridinyl; alkynylcarbamylpyridinyl; dialkenylcarbamylbicycloalkenyl; alkynylcarbamylbicycloalkenyl;

$R_{14}$ and $R_{15}$ can be the same or different and can be selected from the group consisting of alkenyl; haloalkenyl; hydrogen; alkyl; haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkyl-N-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; cycloalkenyl; phenyl; substituted phenyl wherein said substituents can be selected from alkyl, halogen, haloalkyl, alkoxy, haloalkylamido, phthalamido, hydroxy, alkylcarbamyloxy, alkenylcarbamyloxy, alkylamido, haloalkylamido or alkylcarboalkenyl; phenylsulfonyl; substituted phenylalkyl wherein said substituents can be selected from halogen or alkyl; dioxyalkylene, halophenoxyalkylamidoalkyl; alkylthiodiazolyl; piperidyl; piperidylalkyl; dioxolanylalkyl, thiazolyl; alkylthiazolyl; benzothiazolyl; halobenzothiazolyl; furyl; alkyl-substituted furyl; furylalkyl; pyridyl; alkylpyridyl; alkyloxazolyl; tetrahydrofurylalkyl; 3-cyano, thienyl; alkyl-substituted thienyl; 4,5-polyalkylene-thienyl; α-haloalkylacetamidophenylalkyl; α-haloalkylacetamidonitrophenylalkyl; α-haloalkylacetamidohalophenylalkyl; cyanoalkenyl;

$R_{14}$ and $R_{15}$ when taken together can form a structure consisting of piperidinyl; alkylpiperidinyl; pyridyl; di- or tetrahydropyridinyl; alkyltetrahydropyridyl; morpholyl; alkylmorpholyl; azabicyclononyl; diazacycloalkanyl; benzoalkylpyrrolidinyl; oxazolidinyl; perhydrooxazolidinyl; alkyloxazolidyl; furyloxazolidinyl; thienyloxazolidinyl; pyridyloxazolidinyl; pyrimidinyloxazolidinyl; benzooxazolidinyl; $C_{3-7}$ spirocycloalkyloxazolidinyl; alkylaminoalkenyl; alkylideneimino; pyrrolidinyl; piperidonyl; perhydroazepinyl; perhydroazocinyl; pyrazolyl; dihydropyrazolyl; piperazinyl; perhydro-1,4-diazepinyl; quinolinyl; isoquinolinyl; dihydro-, tetrahydro- and perhydroquinolyl- or -isoquinolyl; indolyl and di- and perhydroindolyl and said combined $R_{14}$ and $R_{15}$ members substituted with those independent $R_{14}$ and $R_{15}$ radicals enumerated above; or (ii) one of the following compounds
 α-[(Cyanomethoxy)imino]benzeneacetonitrile,
 α-[(1,3-Dioxolan-2-yl-methoxy)-imino] benzeneacetonitrile,
 O-[1,3-Dioxolan-2-ylmethyl]-2,2,2-trifluoromethyl-4'-chloroacetophenone oxime, Benzenemethamine, N-[4-(dichloromethylene)-1,3-dithiolan-2-ylidene]-α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)-ethenyl] acetamide,
Ethylene glycol acetal of 1,1-dichloroacetone,
1,3-Dioxolane, 2-(dichloromethyl)-2-methyl-,
5-Thiazolecarboxylic Acid, 2-chloro-4-(trifluoromethyl)-, (phenylmethyl)ester,
Phosphorothioic acid, O,O-diethyl O-(3-methylphenyl) ester,
4-Pentenenitrile, 2-methyl-2-[(4-methylphenyl) thio]-,
5-Chloro-8-(cyanomethoxy)quinoline,
1-Methylhexyl-2-(5-chloro-8-quinolinoxy)-acetate or
O-(Methoxycarbonyl)-2-(8-quinolinoxy)-acetamide oxime.

Preferred herbicidal compounds according to Formula I are those wherein A and B are both nitrogen; R is —SO$_2$N(R$_6$) (R$_7$); R$_1$ is phenyl, pyrimidinyl, triazinyl, thiadiazolyl, pyrazinyl, pyridinyl, or any of said R$_1$ radicals substituted with cyano, halogen, amino, mono- or di-C$_{1-4}$ alkylamino, C$_{1-6}$ alkyl, haloalkyl, alkylthio, alkoxy, alkoxyalkyl, alkoxycarbonyl, alkylthio, alkylsulfinyl or alkylsulfonyl; R$_2$ is hydrogen, halogen, cyano, amino, mono- or di-C$_{1-4}$ alkylamino, C$_{1-6}$ alkyl, alkylsulfinyl, alkylsulfonyl, alkoxy, alkoxyalkyl, alkoxycarbonyl, acyl, acyloxy or pyrrolyl optionally substituted with C$_{1-4}$ alkyl; R$_6$ is hydrogen, C$_{1-4}$ alkyl, acyl, alkylsulfonyl, alkoxy, alkoxycarbonyl, dialkylcarbamoyl or benzyl and R$_7$ is furyl, thiophene or phenyl or those radicals substituted independently with one or more C$_{1-4}$ alkyl, haloalkyl, alkoxy, alkoxyalkyl, haloalkoxyalkyl, alkenyl, alkenyloxy, alkynyloxy, alkylsulfinyl, alkylsulfonyl, alkoxycarbonyl, mono- or di-alkylamino, amino, or nitro groups.

In the above embodiment of the invention, preferred species include N-(2,6-dichloro-3-methylphenyl)-1-(4-chloro-6-methoxypyrimidinyl-2-yl)-1H-1,2,4-triazole-3-sulphonamide; N-(2,6-difluorophenyl)-1-(pyrimidin-2-yl)-5-methyl-1,2,4-triazole-3-sulphonamide; N-(2,6-dichloro-3-methylphenyl)-1(pyrimidin-2-yl)-5-methyl-1,2,4-triazole-3-sulphonamide; N-(2-methyl-6-nitrophenyl)-1-pyrimidin-2-yl)-5-methyl-1,2,4-triazole-3-sulphonamide; N-(2,6-difluorophenyl)-1-(4,6-dimethylpyrimidin-2-yl)-5-methyl-1,2,4-triazole-3-sulphonamide; N-(2,6-dichlorophenyl)-1-pyrimidin-2-yl)-5-methyl-1,2,4-triazole-3-sulphonamide; N-(2,6-difluorophenyl)-1-(4-methylpyrimidin-2-yl)-5-methyl-1,2,4-triazole-3-sulphonamide; N-(2,6-difluorophenyl)-1-(4-methoxy-6-methylpyrimidin-2-yl)-5-methyl-1,2,4-triazole-3-sulphonamide; N-(2,6-dichlorophenyl)-1-(4,6-dimethoxy-1,3,5-triazin-2-yl)-5-methyl-1,2,4-triazole-3-sulphonamide; N-(2,6-dichlorophenyl)-1-(4,6-dimethyl-pyrimidin- 2-yl)-1,2,4-triazole-3-sulphonamide; N-(2,6-dichlorophenyl)-1-(4,6-dimethylpyrimidin-2-yl)-5-methyl-1,2,4-triazole-3-sulphonamide; N-(2-methyl-6-nitrophenyl)-1-(4,6-dimethylpyrimidin-2-yl)-5-methyl-1,2,4-triazole-3-sulphonamide; N-(2,6-dichlorophenyl)-5-(2,5-dimethylpyrrol-1-yl)-1,2,4-triazole-3-sulphonamide; N-(2,6-difluorophenyl)-5-(2,5-dimethylpyrrol-1-yl)-1,2,4-triazole-3-sulphonamide; N-(2,6-dichloro-3-methyl-phenyl)-1-(4,6-dimethylpyrimidin-2-yl)-1,2,4-triazole-3-sulphonamide; N-(2,6-dichlorophenyl)-5-amino-1-(4,6-dimethylpyrimidin-2-yl)-1,2,4-triazole-3-sulphonamide; or N-(2,6-dichloro-3-methylphenyl)-5-amino-1-(4,6-dimethoxy-1,3,5-triazin-2-yl)-1,2,4-triazole-3-sulphonamide.

In other embodiments of the invention, more preferred herbicidal compounds according to Formula I are those wherein A and B are both nitrogen (N), R is —SO$_2$N(R$_6$)(R$_7$) and R$_1$ and R$_2$ are combined to form one of the following divalent radicals:

(a)

(b)

(c)

(d)

(e)

(f)

(g)

wherein R$_6$ and R$_7$ are as defined above and X, Y and Z are independently an R$_4$ member, SO$_2$, or adjacent X and Y or Y and Z members may be combined to form a saturated, partially unsaturated or unsaturated homocyclic ring or heterocyclic ring containing up to 10 ring members of which up to 4 may be oxygen, sulfur and/or N and D is oxygen or sulfur.

Preferred compounds containing the above divalent structures are those wherein R$_6$ is hydrogen, alkyl, alkenyl, alkoxy, alkoxycarbonyl, alkoxythiocarbonyl, alkylsulfinyl or alkylsulfonyl having up to 6 carbon atoms; amino, mono- or di-C$_{1-4}$ alkylamino or -alkylaminocarbonyl; phenyl, benzyl, benzoyl or an R$_6$ member when not self-inclusive substituted with one or more halogen, nitro, C$_{1-4}$ alkyl, haloalkyl or alkoxy radicals; R$_7$ is unsubstituted phenyl or pyrazolyl or optionally substituted independently with one or more phenyl, halogen, nitro, trifluoromethyl, C$_{1-6}$ alkyl, alkoxy, alkoxyalkyl, alkoxycarbonyl, —S(O)$_n$ alkyl, —S(O)$_n$C$_m$(K)$_{2m}$H, —S(O)$_n$CK$_m$, amino, carbamyl, mono- or di-C$_{1-4}$ alkylamino or -alkyl carbamyl; X, Y and Z are independently hydrogen, halogen, C$_{1-4}$ alkyl, haloalkyl, alkoxy, alkylthio or alkylsulfonyl, preferably substituted in one meta position and one or both ortho positions; m and n are integers from 0–3 inclusive and K is halogen.

Among preferred species of compounds wherein R$_1$ and R$_2$ are combined to form the bivalent radical (a) above, its tetrahydro analogs of bivalent radical (b) or their agriculturally-acceptable salts are the following compounds:
5,7-di-methyl-N-(2,6-dichlorophenyl)-1,2,4-triazolo[1,5-a]-pyrimidine-2-sulfonamide;
5-methyl-N-(2,6-dichlorophenyl)-1,2,4-triazolo[1,5-a]-pyrimidine-2-sulfonamide;
5-methyl-N-(2-bromo-6-chlorophenyl)-1,2,4-triazolo[1,5-a]-pyrimidine-2-sulfonamide;
5-methyl-N-(2,6-difluoro-3-methylphenyl)-1,2,4-triazolo-[1,5-a]-pyrimidine-2-sulfonamide;
5-methyl-N-(2,6-difluorophenyl)-1,2,4-triazolo[1,5-a]-pyrimidine-2-sulfonamide;
5,7-dimethoxy-N-(2,6-dichloro-3-methylphenyl)-1,2,4-triazolo-[1,5-a]-pyrimidine-2-sulfonamide;
5,7-dimethoxy-N-(2-methoxy-6-trifluoromethylphenyl)-1,2,4-triazolo-[1,5-a]-pyrimidine-2-sulfonamide;

5-methyl-7-methylthio-N-(2,6-dichlorophenyl)-1,2,4-triazolo-[1,5-a]-pyrimidine-2-sulfonamide;

5-methyl-7-methylthio-N-(2-trifluoromethylphenyl)-1,2,4-triazolo-[1,5-a]-pyrimidine-2-sulfonamide;

7-ethoxy-5-methyl-N-(2,6-dichloro-3-methylphenyl)-1,2,4-triazolo-[1,5-a]pyrimidine-2-sulfonamide;

5,7-dimethyl-N-(2-chloro-6-phenylphenyl)-1,2,4-triazolo[1,5-a]pyrimidine-2-sulfonamide;

5-methyl-N-(2-methyl-6-nitrophenyl)-1,2,4-triazolo[1,5-a]-pyrimidine-2-sulfonamide;

5-methyl-N-(2-chloro-6-methylphenyl)-1,2,4-triazolo[1,5-a]-pyrimidine-2-sulfonamide;

Methyl-3-methyl-N-(5,7-dimethyl-1,2,4-triazolo-[1,5-a]-pyrimidine-2-sulfonyl)anthranilate;

Methyl-3-methyl-N-(5-methyl-7-ethoxy-1,2,4-triazolo-[1,5-a]-pyrimidine-2-sulfonyl)-anthranilate;

Isopropyl-3-methyl-N-(5-methyl-1,2,4-triazolo-[1,5-a]-pyrimidine-2-sulfonyl)anthranilate;

6-Methyl-N-(2-bromo-6-methylphenyl)-1,2,4-triazolo-[1,5-a]-pyrimidine-2-sulfonamide;

6-Methyl-N-(2-fluoro-6-chlorophenyl)-1,2,4-triazolo-[1,5-a]-pyrimidine-2-sulfonamide;

6-Methyl-N-(2-chloro-6-methylphenyl)-1,2,4-triazolo[1,5-a]-pyrimidine-2-sulfonamide;

6-Methyl-N-(2-methyl-6-nitrophenyl)-1,2,4-triazolo-[1,5-a]-pyrimidine-2-sulfonamide;

7-Ethoxy-5-methyl-N-(2-trifluoromethylphenyl)-1,2,4-triazolo-[1,5-a]-pyrimidine-2-sulfonamide;

7-Methoxy-5-methyl-N-(2,6-dichloro-3-methylphenyl)-1,2,4-triazolo-[1,5-a]-pyrimidine-2-sulfonamide;

7-Ethoxy-5-methyl-N-(2-bromo-6-chloro-3-methylphenyl)-1,2,4-triazolo-[1,5-a]-pyrimidine-2-sulfonamide;

5,7-Dimethoxy-N-(2,6-dibromo-3-methylphenyl)-1,2,4-triazolo-[1,5-a]-pyrimidine-2-sulfonamide;

5,7-Dimethoxy-N-(2,6-dichlorophenyl)-1,2,4-triazolo-[1,5-a]-pyrimidine-2-sulfonamide;

7-Methyl-N-(2,6-dichlorophenyl)-1,2,4-triazolo-[1,5-a]-pyrimidine-2-sulfonamide;

N-(2,6-Dichlorophenyl)-1,2,4-triazolo-[1,5-a]-pyrimidine-2-sulfonamide;

7-Ethoxy-5-methyl-N-(2,6-dibromo-3-methylphenyl)-1,2,4-triazolo-[1,5-a]-pyrimidine-2-sulfonamide;

6-Chloro-N-(2,6-difluorophenyl)-1,2,4-triazolo-[1,5-a]-pyrimidine-2-sulfonamide;

5-Methyl-7-trifluoromethyl-N-(2-methoxy-6-trifluoromethylphenyl)-1,2,4-triazolo-[1,5-a]-pyrimidine-2-sulfonamide;

Methyl-3-fluoro-N-(6-chloro-1,2,4-triazolo-[1,5-a]-pyrimidine-2-sulfonyl)anthranilate;

5,7-Dimethyl-N-(1,3-dimethyl-5-trifluoromethyl-4-pyrazolyl)-1,2,4-triazolo-[1,5-a]-pyrimidine-2-sulfonamide;

5-Methyl-N-(1,3-dimethyl-5-trifluoromethyl-4-pyrazolyl)-1,2,4-triazolo-[1,5-a]-pyrimidine-2-sulfonamide;

5,7-Dimethyl-N-(1-methyl-4-ethoxycarbonyl-5-pyrazolyl)-1,2,4-triazolo-[1,5-a]-pyrimidine-2-sulfonamide;

5,7-Dimethoxy-N-(2-chloro-1-napthyl)-1,2,4-triazolo-[1,5-a]pyrimidine-2-sulfonamide;

5-Methyl-7-methoxy-N-(2-chloro-1-naphthyl)-1,2,4-triazolo-[1,5-a]-pyrimidine-2-sulfonamide;

5-Methyl-7-ethoxy-N-(2-chloro-1-naphthyl)-1,2,4-triazolo-[1,5-a]-pyrimidine-2-sulfonamide;

5-Methyl-N-(2-methylpropanoyl)-N-(2,6-difluorophenyl)-1,2,4-triazolo-[1,5-a]-pyrimidine-2-sulfonamide;

5-Methyl-N-acetyl-N-(2,6-dichlorophenyl)-1,2,4-triazolo-[1,5-a]-pyrimidine-2-sulfonamide;

5,7-Dimethyl-2-(N-[2-chloro, 6-propargyloxyphenyl]-sulphamoyl)-1,2,4-triazolo[1,5-a]-pyrimidine;

5,7-Dimethyl-2-(N-[2-chloro-6-(2-ethoxyethoxy)-phenyl]-sulphamoyl)-1,2,4-triazolo[1,5-a]-pyrimidine;

5,7-Dimethyl-2-(N-[2-benzyloxy-6-chlorophenyl]-sulphamoyl)-1,2,4-triazolo[1,5-a]-pyrimidine;

5,7-Dimethyl-2-(N-[2-allyloxy-6-fluorophenyl]-sulphamoyl)-1,2,4-triazolo[1,5-a]-pyrimidine;

5,7-Dimethyl-2-(N-[2-chloro-6-(2-methoxymethoxy)-phenyl]-sulphamoyl)-1,2,4-triazolo[1,5-a]-pyrimidine;

5,7-Dimethyl-2-(N-[2-chloro-6-(2-hydroxyethoxy)-phenyl]-sulphamoyl)-1,2,4-triazolo[1,5-a]-pyrimidine;

5,7-Dimethyl-2-(N-[2-2-ethoxyethoxy)-6-fluorophenyl]-sulphamoyl)-1,2,4-triazolo[1,5-a]-pyrimidine;

5,7-Dimethyl-2-(N-[2-fluoro-6-(2-methylthioethoxy)-phenyl]-sulphamoyl)-1,2,4-triazolo-[1,5-a]-pyrimidine;

5,7-Dimethyl-2-(N-[2-chloro-6-(2-phenoxyethoxy)-phenyl]sulphamoyl)-1,2,4-triazolo[1,5-a]-pyrimidine;

5,7-Dimethyl-2-(N-[2-chloro-6-(2-methoxyethoxy)-phenyl]-sulphamoyl-1,2,4-triazolo-[1,5-a]-pyrimidine;

5,7-Dimethyl-2-(N-[2-chloro-6-(2-n-propoxyethoxy)-phenyl]-sulphamoyl)-1,2,4-triazolo[1,5-a]-pyrimidine;

5,7-Dimethyl-2-(N-[2-chloro-6-(3-methoxy-n-propoxy)phenyl]-sulphamoyl)-1,2,4-triazolo-[1,5-a]-pyrimidine;

5,7-Dimethyl-2-(N-[2-chloro-6-(2-isopropoxy)-ethoxyphenyl]-sulphamoyl)-1,2,4-triazolo-[1,5-a]-pyrimidine;

5,7-Dimethyl-(N-[2-fluoro-6-(2-n-propoxyethoxy)-phenyl)-sulphamoyl)-1,2,4-triazolo-[1,5-a]-pyrimidine;

5,7-Dimethyl-2-(N-[2-(2-ethoxyethoxy)phenyl]-sulphamoyl)-1,2,4-triazolo-[1,5-a)-pyrimidine;

5,7-Dimethyl-2-(N-[2,6-di(2-ethoxyethoxy)phenyl]-sulphamoyl)-1,2,4-triazolo-[1,5-a]-pyrimidine;

5,7-Dimethyl-2-(N-[2-2-ethoxyethoxy)-6-methoxyphenyl]-sulphamoyl)-1,2,4-triazolo[1,5-a]-pyrimidine;

5,7-Dimethyl)-2-(N-[2-chloro-6-tetrahydrofurfur-2-yloxyphenyl]-sulphamoyl)-1,2,4-triazolo-[1,5-a]-pyrimidine;

5,7-Dimethyl-2-(N-[2-(2-emthoxyethylamino)-phenyl]-sulphamoyl)-1,2,4-triazolo[1,5-a]-pyrimidine;

5,7-Dimethyl-2-(N-[2-(2-methoxyethylthio)phenyl]-sulphamoyl)-1,2,4-triazolo-[1,5-a]-pyrimidine;

5,7-Dimethyl-2-(N-acetyl-N-[2-chloro-6-(2-ethoxyethoxy)phenyl]-sulphamoyl)-1,2,4-triazolo-[1,5-a]-pyrimidine;

5,7-Dimethyl-2-(N-acetyl-N-[2-chloro-6-(2-methoxyethoxy)phenyl]-sulphamoyl)-1,2,4-triazolo-[1,5-a]-pyrimidine;

5,7-Dimethyl-2-(N-methyl-N-[2-chloro-6-(2-ethoxyethoxy)phenyl]-sulphamoyl)-1,2,4-triazolo-[1,5-a]-pyrimidine;

5,7-Dimethyl-2-(N-[2-(2-ethoxyethoxy)-6-nitrophenyl]sulphamoyl)-1,2,4-triazolo-[1,5-a]-pyrimidine; and 5-Methoxymethyl-N-(2-chloro-6-methylphenyl)-1,2,4-triazolo-[2,5-a]-pyrimidine-2-sulfonamide.

Other preferred herbicidal compounds for use herein wherein in Formula I $R_1$ and $R_2$ are combined to form divalent radical (a) above, i.e.,

and R is —$SO_2N(R_6)$ $(R_7)$, are those wherein A is $CR_3$, B is N and $R_6$, $R_7$, X, Y and Z have the above-defined meanings and $R_3$ is H, halogen, $NO_2$, CN, amino, phenyl, phenylthio, phenoxy, $C_{1-4}$ alkyl, mono- or di-$C_{1-4}$ alkylamino or alkoxy; —$S(O)_{0-3}$—$C_{1-4}$ alkyl; $C(O)C_{1-4}$ alkyl, -alkoxy, -alkylthio, mono- or dialkylamino or -phenyl; or a substitutable $R_3$ member substituted where not self-inclusive with halogen, NO₂, CN, CF₃ and/or C₁₋₃ alkyl, preferably methyl.

Preferred compounds according to the foregoing embodiment are those wherein:

X and Z are independently H, CN, halogen, amino, C₁₋₄ alkyl, haloalkyl, alkylthio, alkoxy or mono- or dialkylamino;

Y is H, CN, halogen, C₁₋₄ alkyl, haloalkyl or alkoxy;

R₃ is halogen, NO₂, CN, C₁₋₄ alkyl, haloalkyl, C(O)alkyl or C(O)alkoxy;

R₆ is H, benzyl, C(O)C₁₋₄alkyl or -haloalkyl and agriculturally-acceptable salts thereof when R₆ is H and R₇ is phenyl substituted in at least one ortho position with halogen, CN, NO₂, C₁₋₄ alkyl, haloalkyl or S(O)₁₋₃alkyl or haloalkyl; amino, mono- or di-C₁₋₄alkylamino, optionally substituted phenyl, phenylthio, phenoxy or benzyl, wherein said substituents are from 1 to 4 of halogen, NO₂, CF₃, CN or C₁₋₃ alkyl, preferably methyl; and at least one of the meta positions of the R₇ phenyl group is substituted with a C₁₋₃ alkyl, preferably methyl.

Representative species of the preceding compounds include the following:

N-(2,6-difluorophenyl)-4,6-dimethylimidazolo[1,2-a]-pyrimidine-2-sulfonamide;

N-(2,6-difluorophenyl)-3-chloro-4,6-dimethylimidazolo[1,2-a]-pyrimidine-2-sulfonamide;

N-(2,6-difluorophenyl)-3-bromo-4,6-dimethylimidazolo[1,2-a]-pyrimidine-2-sulfonamide;

N-(2,6-difluorophenyl)-3-methylthio-4,6-dimethylimidazolo[1,2-a]-pyrimidine-2-sulfonamide;

N-(2,6-dichlorophenyl)-4,6-dimethylimidazolo[1,2-a]-pyrimidine-2-sulfonamide;

N-(2,6-difluorophenyl)-3-cyano-4,6-dimethylimidazolo[1,2-a]-pyrimidine-2-sulfonamide;

N-(2,6-difluorophenyl)-N-benzyl-3-chloro-4,6-dimethylimidazolo[1,2-a]-pyrimidine-2-sulfonamide;

N-(2-trifluoromethylphenyl)-4,6-dimethylimidazolo[1,2-a]-pyrimidine-2-sulfonamide;

N-(2-trifluoromethylphenyl)-3-chloro-4,6-dimethylimidazolo[1,2-a]-pyrimidine-2-sulfonamide;

N-(2-carbomethoxy-6-methylphenyl)-3-chloro-4,6-dimethylimidazolo[1,2-a]-pyrimidine-2-sulfonamide;

N-(2,6-dichlorophenyl)-3-chloro-4,6-dimethylimidazolo[1,2-a]-pyrimidine-2-sulfonamide;

N-(2-chloro-6-methylphenyl-3-chloro-4,6-dimethylimidazolo[1,2-a]-pyrimidine-2-sulfonamide;

N-(2,6-difluorophenyl)-4-chloro-6-methylimidazolo[1,2-a]-pyrimidine-2-sulfonamide;

N-(2,6-difluorophenyl)-4-methoxy-6-methylimidazolo[1,2-a]-pyrimidine-2-sulfonamide;

N-(2,6-difluorophenyl)-4,6-dichloroimidazolo-[1,2-a]-pyrimidine-2-sulfonamide;

N-(2,6-difluorophenyl)-4,6-bismethoxyimidazolo-[1,2-a]-pyrimidine-2-sulfonamide monohydrate;

Preferred and representative herbicidal compounds according to Formula I wherein R₁ and R₂ are combined to form the bivalent radicals (c) and (d) above include tautomeric forms of the following compounds:

5,7-Dimethyl-N-(2-chloro-6-methylphenyl)-1,2,4-triazolo-[1,5-a]-[4H,7H]-dihydropyrimidine-2-sulphonamide, 7-Methyl-N-(2-chloro-6-methylphenyl)-1,2,4-triazolo-[1,5-a][4H,7H]-dihydropyrimidine-2-sulphonamide;

5,7-Dimethyl-N-(2-chloro-6-ethoxyphenyl)-1,2,4-triazolo-[1,5-a][4H,7H]-dihydropyrimidine-2-sulphonamide or 5,7-Dimethyl-N-(2-chloro-6-isopropoxyphenyl)-1,2,4-triazolo-[1,5-a][4H,7H]-dihydropyrimidine-2-sulphonamide.

Another group of preferred herbicidal compounds of Formula I are those wherein R₁ and R₂ combine to form the divalent radical (e) above, i.e.,

wherein

X is H, CF₃, CF₁₋₄ alkyl, alkylthio or alkoxy;

Y and Z are independently H, CF₃, CF₃, halogen or C₁₋₄ alkoxy; provided that at least one of X, Y or Z is C₁₋₄ alkoxy;

R₆ is H or C(O)C₁₋₄ alkyl or -haloalkyl and agriculturally-acceptable salts thereof when R₆ is H and R₇ is phenyl substituted in at least one ortho position with halogen, CN, NO₂, C₁₋₄ alkyl, haloalkyl or S(O)₁₋₃ alkyl or haloalkyl; amino, mono- or di- C₁₋₄ alkylamino, optionally-substituted phenyl, phenylthio, phenoxy or benzyl, wherein said substituents are from 1 to 4 of halogen, NO₂, CF₃, CN or C₁₋₃ alkyl, preferably methyl; and at least one of the meta positions of the R₇ phenyl group is substituted with a C₁₋₃ alkyl, preferably methyl.

One preferred compound according to those defined in the preceding paragraph is 5-fluoro-7-methoxy-N-(2,6-difluorophenyl)-1,2,4-triazolo[1,5-c]-pyrimidine-2-sulfonamide.

Still another group of herbicidal sulfonamide compounds useful in combination with antidotal compounds according to this invention are those identified as (6,7)-dihydro-[1,2,4]-triazolo[1,5-a]-[1,3,5]-triazine-2-sulfonamides. Such compounds are those according to Formula I wherein A and B are both N, R is SO₂N(R₆) (R₇) and R₁ and R₂ are combined to form divalent radical (f) above, i.e.,

wherein D is oxygen or sulfur;

X and Y are independently H, alkyl, alkenyl or alkynyl having up to 6 carbon atoms, phenyl, phenylalkyl, phenylalkenyl, phenylalkynyl or where not self-inclusive an X or Y member other than H substituted with one or more halogen, C₁₋₄ acyl, alkoxy, alkoxycarbonyl, alkoxycarbonyl-C₁₋₃ alkylene, carbamoyl, mono- or di-C₁₋₆ carbamoyl or S(O)₀₋₃C₁₋₆ alkyl;

R₆ is an X member or alkali metal atom or a single metal equivalent of an alkaline earth, other metal or ammonium anion, optionally substituted with C₁₋₆ alkyl and R₇ is preferably phenyl, naphthyl, pyridyl or thienyl, optionally substituted with halogen, CN, NO₂, S(O)₀₋₃C₁₋₆ alkyl, —C₂₋₆ alkenyl or alkynyl, amino, carbamoyl, mono- or di-C₁₋₄ alkylamino or -alkylcarbamoyl, C₁₋₆ alkyl, acyl, alkoxy, alkoxyalkyl, alkoxycarbanoyl-C₁₋₃ alkyl; phenyl or phenoxy optionally substituted with one or more C₁₋₄ alkyl, alkoxy, alkylthio, halogen, NO₂ or amino, which substituents where not self-inclusive and substitutable, substituted with alkyl, alkenyl or alkynyl having up to 6 carbons, which may optionally be substituted with one or more halogen, OH, CN, NO₂ or C₁₋₄ alkoxy or alkoxycarbonyl.

Exemplary preferred species according to the structure defined in the preceding paragraph include those wherein R₇ is phenyl substituted in the ortho positions independently with halogen, CF₃, NO₂, C₁₋₃ alkyl, alkoxy or alkoxycarbonyl and substituted in the meta and para positions with halogen, CF₃ or C₁₋₄ alkyl;

R₆ is H, C₁₋₄ acyl or a single equivalent of a metal ion and

X and Y are independently H, phenyl, alkyl, alkenyl or alkynyl having up to 6 carbon atoms.

Preferred species according to the preceding description include the following:

N-(2,6-Dichlorophenyl)-6,7-dihydro-N,5,6-trimethyl-7-oxo[1,2,4]triazolo[1,5-a][1,3,5]-triazine-2-sulphonamide;

N-(2,6-Dichlorophenyl)-6,7-dihydro-5,6-dimethyl-7-oxo[1,2,4]triazole[1,5-a][1,3,5]-triazine-2-sulphonamide;

N-(2,6-dichlorophenyl)-6,7-dihydro-5,6-dimethyl-7-thioxo-[1,2,4]triazolo[1,5-a]-[1,3,5]-triazine-2-sulphonamide;

N-(2,6-Dichlorophenyl)-6,7-dihydro-5,6-dimethyl-7-thioxo-[1,2,4]triazolo[1,5-a][1,3,5]triazine-2-sulphonamide;

N-(2,6-Dichloro-3-methylphenyl)-6,7-dihydro-5,6-dimethyl-7-thioxo-[1,2,4]triazolo[1,5-a][1,3,5]-triazine-2-sulphonamide;

6,7-Dihydro-5,6-dimethyl-N-(2-methyl-6-nitrophenyl)-7-thioxo-[1,2,4]triazolo-[1,5-a]-[1,3,5]-triazine-2-sulphonamide;

N-(2-Chloro-6-fluorophenyl)-6,7-dihydro-5,6-dimethyl-7-thioxo-[1,2,4]triazolo[1,5-a][1,3,5]-triazine-2-sulphonamide;

N-(2,6-Difluorophenyl)-6,7-dihydro-5,6-dimethyl-7-thioxo-[1,2,4]triazolo[1,5-a][1,3,5]-triazine-2-sulphonamide;

N-(2,6-Dibromophenyl)-6,7-dihydro-5,6-dimethyl-7-thioxo-[1,2,4]triazolo[1,5-a]-[1,3,5]-triazine-2-sulphonamide;

6,7-Dihydro-5,6-dimethyl-7-thioxo-N-(2-trifluoromethylphenyl)-[1,2,4]triazolo[1,5-a]-[1,3,5]-triazine-2-sulphonamide;

6,7-Dihydro-5,6-dimethyl-N-phenyl-7-thioxo-[1,2,4]-triazolo[1,5-a]-[1,3,5]-triazine-2-sulphonamide;

N-(2-Chlorophenyl)-6,7-dihydro-5,6-dimethyl-7-thioxo-[1,2,4]triazolo-(1,5-a]-[1,3,5]-triazine-2-sulfonamide.

A modification of the preceding 6,7-dihydrotriazolotriazine sulfonamides includes compounds according to Formula I wherein the only change is that B is $CR_3$, rather than N; D, X, Y, R, $R_6$, $R_7$ and $R_1$ combined with $R_2$ to form the divalent radical (f), have the same meanings as defined above and $R_3$ is defined to have the same members as X and Y.

Preferred compounds according to this embodiment of the invention herbicides include those wherein $R_3$ is H, CN, $NO_2$, $C_{1-4}$ acyl or alkoxycarbonyl; carbamoyl, $C_{1-4}$ mono- or dialkyl carbamoyl or $S(O)_{0-3}$ $C_{1-4}$ alkyl;

$R_7$ is phenyl substituted in the ortho positions independently with halogen, $CF_3$, $NO_2$, $C_{1-3}$ alkyl, alkoxy or alkoxycarbonyl and substituted in the meta and para positions with halogen $CF_3$ or $C_{1-4}$ alkyl;

$R_6$ is H, $C_{1-4}$ acyl or a single equivalent of a metal ion and

X and Y are independently H, phenyl, alkyl, alkenyl or alkynyl having up to 6 carbon atoms.

Preferred species according to the preceding description include the following:

N-(2,6-Dichlorophenyl)-6,7-dihydro-5,6-dimethyl-3-methoxycarbonyl-7-oxopyrazolo[1,5-a][1,3,5]-triazine-2-sulphonamide;

N-(2,6-Difluorophenyl)-6,7-dihydro-5,6-dimethyl-3-methoxycarbonyl-7-thioxopyrazolo[1,5-a][1,3,5]-triazine-2-sulphonamide;

N-(2,6-Difluorophenyl)-6,7-dihydro-5,6-dimethyl-3-methoxycarbonyl-7-oxopyrazolo[1,5-a][1,3,5]-triazine-2-sulphonamide;

N-(2,6-Dichlorophenyl)-6,7-dihydro-5,6-dimethyl-3-methoxycarbonyl-7-thioxopyrazolo[1,5-a][1,3,5]-triazine-2-sulphonamide;

N-(2,6-Dichloro-3-methylphenyl)-6,7-dihydro-5,6-dimethyl-3-methoxycarbonyl-7-oxopyrazolo[1,5-a]-[1,3,5]-triazine-2-sulphonamide;

N-(2,6-Dichloro-3-methylphenyl)-6,7-dihydro-5,6-dimethyl-3-methoxycarbonyl-7-thioxopyrazolo-[1,5-a][1,3,5]-triazine-2-sulphonamide;

N-(2-Chloro-6-fluorophenyl)-6,7-dihydro-5,6-dimethyl-3-methoxycarbonyl-7-oxopyrazolo-[1,5-a][1,3,5]-triazine-2-sulphonamide;

N-(2-Chloro-6-fluorophenyl)-6,7-dihydro-5,6-dimethyl-3-methoxycarbonyl-7-thioxopyrazolo-[1,5-a][1,3,5]-triazine-2-sulphonamide;

N-(2-Chloro-6-methylphenyl)-6,7-dihydro-5,6-dimethyl-3-methoxycarbonyl-7-oxopyrazolo-[1,5-a][1,3,5]-triazine-2-sulphonamide;

N-(2-Chloro-6-methylphenyl)-6,7-dihydro-5,6-dimethyl-3-methoxycarbonyl-7-thioxopyrazolo-[1,5-a][1,3,5]-triazine-2-sulphonamide;

N-(2,6-Dibromophenyl)-6,7-dihydro-5,6-dimethyl-3-methoxycarbonyl-7-oxopyrazolo[1,5-a][1,3,5]-triazine-2-sulphonamide;

N-(2,6-Dibromophenyl)-6,7-dihydro-5,6-dimethyl-3-methoxycarbonyl-7-thioxopyrazolo[1,5-a][1,3,5]-triazine-2-sulfonamide.

Another group of triazolosulfonamides safened according to this invention are those according to Formula I wherein $R_1$ and $R_2$ are combined to form the divalent radical (g) above, i.e.,

and are characterized as thiazolotriazole sulfonamides, wherein:

X and Y are independently H, OH, CN, $NO_2$, halogen; alkyl, acyl, alkoxy, alkoxycarbonyl, alkenyl, alkenyloxy, alkynyl or alkynyloxy each having up to 6 carbon atoms; aryl, aralkyl or heterocyclic radical having up to 10 ring members of which up to 4 may be O, S and/or N atoms; or X and Y may be combined to form an alkylene chain of 3 or 4 carbon atoms; or said X and Y substitutable members substituted with another X or Y member when not self-inclusive;

$R_6$ is H, acyl, alkyl, alkenyl or alkoxycarbonyl having up to 6 carbon atoms; aryl, alkaryl or heterocyclyl having up to 10 ring members of which up to 4 may be O, S and/or N atoms; an alkali metal ion, ammonium or $C_{1-4}$ alkylammonium; or a substitutable $R_6$ member when not self inclusive substituted with alkyl, alkoxy, acyl, alkenyl, alkenyloxy, alkynyl, alkynyloxy having up to 6 carbon atoms and $R_7$ is an aromatic or heteroaromatic $R_6$ member.

Preferred members within the above thiaazolotriazole sulfonamides are those wherein X and Y are independently H or $C_{1-6}$ alkyl, preferably methyl; $R_6$ is H and $R_7$ is phenyl substituted with one or more halogen, $NO_2$, $C_{1-4}$ alkyl, alkoxy, alkoxycarbonyl or alkylthio groups.

A preferred species according to the preceding group of compounds is N-(2,6-difluorophenyl)-thiazole[3,2-b][1,2,4]triazole-2-sulfonamide.

The preceding embodiments of triazolo- and imidazolopyrimidine sulfonamide herbicides according to Formula I used in this invention are characterized by the R moiety —$SO_2N(R_6)$ ($R_7$). In the following embodiments analogous herbicides used herein are characterized by the R moiety —$N(R_4)SO_2$—$R_5$. In these embodiments both A and B are N, although it is within the purview of the invention to replace either A or B with the $CR_3$ moiety as with the foregoing embodiments.

The first group of compounds according to this embodiment of analogous compounds described in the preceding paragraph are those wherein $R_1$ and $R_2$ are combined to form the above bivalent radical (a), i.e.,

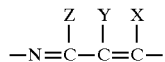 (a)

or their tetrahydro analogs of bivalent radical (b) above, i.e.,

 (b)

wherein X, Y, Z, $R_4$ and $R_5$ of Formula I have the same meanings as those described earlier herein.

Preferred compounds within this embodiment of herbicidal compounds are those wherein Y and $R_4$ are H;

X and Z are H or $C_{1-4}$ alkyl or alkoxy and $R_5$ is phenyl substituted in a first ortho position with halogen, $NO_2$, $CF_3$, CN, carboxyl or $C_{1-4}$ alkoxycarbonyl; in the other ortho position in H, halogen or $C_{1-4}$ alkoxycarbonyl and in the meta position adjacent said first ortho position with H, halogen or $C_{1-4}$ alkyl.

Preferred species in the foregoing group of compounds include the following:

N-5,7-dimethyl-4,5,6,7-tetrahydro-1,2,4-triazolo-[1,5-a]-pyrimidine-2-yl-2-(2,6-dichlorophenyl)-sulfonamide;

N-5-methyl-4,5,6,7-tetrahydro-1,2,4-triazolo[1,5-a]-pyrimidine-2-yl-2-(2,6-difluorophenyl)-sulfonamide;

N-(5,7-Dimethyl-1,2,4-triazolo[1,5-a]-pyrimidin-2-yl)-2-thiophene sulfonamide;

N-Acetyl-2,6-dichloro-N-(5,7-dimethyl-1,2,4-triazolo[1,5-a]-pyrimidin-2-yl)-benzenesulfonamide;

N-(5-Amino-1,2,4-triazol-3-yl)-2-nitrobenzenesulfonamide;

N-(5,7-Dimethyl-1,2,4-triazolo[1,5-a]-pyrimidin-2-yl)-2-nitrobenzenesulfonamide;

N-(5-Amino-1,2,4-triazol-3-yl)-2,5-dichlorobenzenesulfonamide;

N-(5,7-Dimethyl-1,2,4-triazolo[1,5-a]pyrimidin-2-yl)-2,5-dichlorobenzene-sulfonamide;

2-Chloro-N-(5-methyl-7-trifluoromethyl-1,2,4-triazolo[1,5-a]pyrimidin-2-yl)benzenesulfonamide 2-Chloro-N-(7-methyl-1,2,4-triazolo[1,5-a]-pyrimidin-2-yl)benzenesulfonamide;

2-Chloro-N-(1,2,4-triazolo[1,5-a]pyrimidin-2-yl)-benzenesulfonamide;

2-Chloro-N-(6-Chloro-1,2,4-triazolo[1,5-a]-pyrimidin-2-yl)benzenesulfonamide;

2-Chloro-N-(6-methyl-1,2,4-triazolo[1,5-a]-pyrimidin-2-yl)benzenesulfonamide;

N-(5-Amino-1,2,4-triazol-3-yl)-2,6-dichlorobenzenesulfonamide;

A second group of preferred herbicides in the class of those wherein in Formula I R is $N(R_4)SO_2R_5$ includes compounds wherein $R_1$ and $R_2$ are combined to form the bivalent radical (h), i.e.,

 (h)

wherein X, Y, $R_4$ and $R_5$ have the same general meanings and preferred members as described above in the first group of compounds wherein R is $N(R_4)SO_2(R_5)$.

Exemplary compounds within this group include the following compounds wherein $R_5$ is a substituted phenyl radical:

N-(5,7-dimethyl)-6,7-dihydro-[1,2,4]-triazole-[1,5-a][1,3,5]-triazine-2-(2,6-difluorophenyl)-sulfonamide;

N-(5-methyl)-6,7-dihydro-[1,2,4]-triazole[1,5-a]-[1,3,5]-triazine-2-(2,6-difluorophenyl)-sulfonamide;

N-(7-methoxy0-6,7-dihydro-[1,2,4]-triazole[1,5-a]-[1,3,5]-triazine-2-(2,6-dichlorophenyl)-sulfonamide;

N-(5,7-dimethoxy)-6,7-dihydro-[1,2,4]-triazole-[1,5-a][1,3,5]-triazine-2-(2,3,6-trimethylphenyl)sulfonamide;

N-(5-chloro)-6,7-dihydro-[1,2,4]-triazole[1,5-a]-[1,3,5)-triazine-2-(2-acetyl-6-methylphenyl)-sulfonamide and N-(5-methoxymethyl)-6,7-dihydro[1,2,4]-triazole-[1,5-a][1,3,5]-triazine-2-(2,6-difluorophenyl)-sulfonamide.

Other preferred compounds are those wherein $R_5$ is a substituted pyrazolyl, furanyl or thiophenyl radical. Representative $R_5$ pyrazolyl members are the pyrazol-4-yl sulfonamide compounds substituted in the 1-position with H, $C_{1-4}$ alkyl or phenyl and in the 3- and 5-positions with H, halogen, CN, $NO_2$, $CF_3$, phenyl, benzyl, $C_{1-4}$ alkyl, aminocarbonyl, mono- or dialkylamino carbonyl, alkoxycarbonyl, alkenyloxycarbonyl or alkynyloxycarbonyl, benzyloxycarbonyl or said phenyl and benzyl members substituted with halogen, $C_{1-4}$ alkyl or alkoxy.

Representative $R_5$ furanyl and thiophenyl members are the 2-yl and 3-yl isomers substituted in the substitutable positions of the 2-yl radical with one or more H, halogen or $C_{1-4}$ alkyl and in the 3-yl radical with one or more H, halogen or COO-alkyl, -alkenyl or -alkynyl having up to 6 carbon atoms. Examples of such compounds are:

N-(5,7-dimethyl)-6,7-dihydro-[1,2,4]-triazole-[1,5-a][1,3,5]-triazine-2-thiophene sulfonamide;

N-(5-methyl)-6,7-dihydro-[1,2,4]-triazole-[1,5-a]- [1,3,5]-triazine-2-thiophenesulfonamide;

N-(5,7-dimethoxy)-6,7-dihydro-[1,2,4]-triazole-[1,5-a][1,3,5]-triazine-2-furanesulfonamide;

N-(5-methoxymethyl)-6,7-dihydro-[1,2,4]-triazole-[1,5-a][1,3,5]-triazine-furane sulfonamide;

N-(5-methyl)-6,7-dihydro-[1,2,4]-triazole[1,3,5]-triazine-2-(3-chloro-1-methyl-5-trifluoromethylpyrazol-4-yl)sulfonamide and N-(5,7-dimethyl)-6,7-dihydro-[1,2,4]-triazole-[1,3,5]-triazine-2-[4-chloro-5-methylsulfonyl)-pyrazol-4-yl] sulfonamide.

As described herein, the aforementioned azolopyrimidine sulfonamides may be combined with antidotal compounds and used in that combined form or further combined with other herbicides as co-herbicides.

Preferred herbicidal compounds useful as co-herbicides herein are those according to Formula IV wherein the $R_{11}$ member is an alkoxyalkyl radical of the structure —(E)—O—L, wherein E and L are linear or branched-chain alkyl residues having a combined total of up to 8 carbon atoms; or a substituted or unsubstituted $C_{4-10}$ heterocyclyl or heterocyclylmethyl radical containing from 1 to 4 ring hetero atoms selected independently from N, S or O atoms and the $R_{12}$ member is also one of said heterocyclyl or heterocyclylmethyl radicals or an optionally-substituted phenyl radical. Preferably the phenyl radical is substituted with alkyl groups, especially in the ortho positions. Similarly, some preferred heterocyclic members are substituted with alkyl or alkoxy radicals.

Among the more important heterocyclic $R_{11}$ and/or $R_{12}$ members of Formula IV are mentioned independently, the furanyl, thienyl, pyrazolyl, pyrrolyl, isoxazolyl, isothiazolyl, triazolyl, imidazolyl, and pyrimidinyl radicals and their analogs having a methylene (—$CH_2$—) moiety connecting the heterocyclic radical to the acetamide nitrogen atom, e.g., pyrazol-1-ylmethyl. When the heterocyclic radical is attached directly to the amide nitrogen (with no intervening methylene moiety), the attachment may be through a ring carbon atom or a ring hetero atom as appropriate.

Other important $R_{11}$ and/or $R_{12}$ members include the following: propynyl, alkoxycarbomethyl or -ethyl, alkoxyiminoalkyl, benzyl, hydroxyalkyl, haloalkoxy and -alkoxyalkyl, cyanoalkoxy and -alkoxyalkyl, methyl, ethyl, propyl, butyl and their isomers, and the like.

Among preferred species of Formula IV are mentioned N-(2,4-dimethylthien-3-yl)-N-(1-methoxyprop-2-yl)-2-chloroacetamide, N-(1H-pyrazol-1-ylmethyl)-N-(2,4-dimethylthien-3-71)-2-chloroacetamide and N-(1-pyrazol-1-ylmethyl)-N-(4,6-dimethoxypyrimidin-5-yl)-2-chloroacetamide.

Another important subgenus of preferred α-haloacetamide compounds useful as co-herbicides are the α-chloroacetanilides according to Formula V

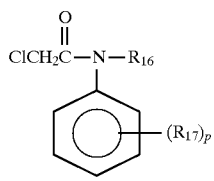

wherein $R_{16}$ is hydrogen, $C_{1-6}$ alkyl, haloalkyl, alkoxy or alkoxyalkyl, alkenyl, haloalkenyl, alkynyl or haloalkynyl having up to 6 carbon atoms, $C_{5-10}$ heterocyclyl or heterocyclylmethyl having O, S and/or N atoms and which may be substituted with halogen, $C_{1-4}$ alkyl, carbonylalkyl or carbonylalkoxyalkyl, nitro, amino or cyano groups;

$R_{17}$ is hydrogen, halogen, nitro, amino, $C_{1-6}$ alkyl, alkoxy or alkoxyalkyl, and p is 0–5.

The most preferred species of Formula V are 2-chloro-2'-ethyl-6'-methyl-N-(ethoxymethyl)acetanilide (common name "acetochlor"), 2-chloro-2',6'-diethyl-N-(methoxymethyl)acetanilide (common name "alachlor"), 2-chloro-2',6'-diethyl-N-(butoxymethyl)acetanilide (common name "butachlor"), 2-chloro-2'-ethyl-6'-methyl-N-(1-methyl-2-methoxyethyl)acetanilide (common name "metolachlor"), 2-chloro-2',6'-diethyl-N-(2-n-propoxyethyl)-acetanilide (common name "pretilachlor") and 2-chloro-2',6'-dimethyl-N-(pyrazolylmethyl)acetanilide (common name "metazachlor").

A larger group of preferred co-herbicides includes the particular preferred species of Formulae IV and V identified above.

One group of preferred antidotal compounds includes those according to Formula II wherein $R_{13}$ is $C_{1-3}$ haloalkyl, $R_{14}$ and $R_{15}$ are independently $C_{2-4}$ alkenyl or haloalkenyl or 1,3-dioxolan-2-yl-methyl and $R_{14}$ and $R_{15}$ when combined form a $C_{4-10}$ saturated or unsaturated heterocyclic ring containing O, S and/or N atoms and which may be substituted with $C_{1-5}$ alkyl, haloalkyl, alkoxy, or alkoxyalkyl or haloacyl groups. The preferred haloalkyl R member in formula II is dichloromethyl. Preferred species in this group of antidotal compounds are N,N-diallyl-dichloroacetamide and N-(2-propenyl)-N-(1,3-dioxolanylmethyl) dichloroacetamide.

Still more preferred antidotal compounds according to Formula II is a sub-group of substituted 1,3-oxazolidinyl dichloroacetamide having the formula

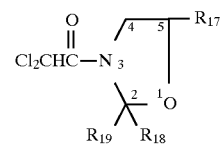

wherein $R_{17}$ is hydrogen, $C_{1-4}$ alkyl, alkylol, haloalkyl or alkoxy, $C_{2-6}$ alkoxyalkyl, a bicyclic hydrocarbon radical having up to 10 carbon atoms, phenyl or a saturated or unsaturated heterocyclic radical having $C_{4-10}$ ring atoms and containing O, S and/or N atoms, or said phenyl and heterocyclic radical substituted with one or more $C_{1-4}$ alkyl, haloalkyl, alkoxy, alkoxyalkyl, halogen or nitro radicals, and $R_{18}$ and $R_{19}$ are independently hydrogen, $C_{1-4}$ alkyl or haloalkyl, phenyl or a heterocyclic $R_{17}$ member or together with the carbon atom to which they are attached may form a $C_3$–$C_7$ spirocycloalkyl group.

Preferred members according to Formula III are those wherein $R_{17}$ is one of said heterocyclic members and $R_{18}$ and $R_{19}$ are independently methyl, trifluoromethyl or when combined with the carbon atom to which attached form a $C_5$ or $C_6$ cycloalkyl radical.

Preferred antidotal compounds according to Formula III are the following compounds:

Oxazolidine, 3-(dichloroacetyl)-2,2,5-trimethyl-,
Oxazolidine, 3-(dichloroacetyl)-2,2-dimethyl-5-phenyl-,
Oxazolidine, 3-(dichloroacetyl)-2,2-dimethyl-5-(2-furanyl)-,
Oxazolidine, 3-(dichloroacetyl)-2,2-dimethyl-5-(2-thienyl)-,
Pyridine, 3-[3-(dichloroacetyl)-2,2-dimethyl-5-oxazolidinyl]-,
4-(dichloroacetyl)-1-oxa-4-azaspiro-(4,5)-decane.

Another group of dichloroacetamide antidotal compounds according to Formula II are the following compounds:
4-(Dichloroacetyl)-3,4-dihydro-3-methyl-2H-2,4-benzoxazine,
Ethanone, 2,2-dichloro-1-(1,2,3,4-tetrahydro-1-methyl-2-isoquinolinyl)-,
N-(Dichloroacetyl)-1,2,3,4-tetrahydroquinaldine,
1-(Dichloroacetyl)-1,2,3,4-tetrahydroquinoline,
Cis/trans-piperazine, 1,4-bis(dichloro-1,4-acetyl)-2,5-dimethyl-,
1,5-Diazacyclononane, 1,5bis-(dichloroacetyl,
1-Azaspiro[4,4]nonane, 1-(dichloroacetyl),
Pyrrolo[1,2-a]-pyrimidine-[6(2H)]-one, 1-(dichloroacetyl)hexahydro-3,3,8a-trimethyl,
2,2-Dimethyl-3-(dichloroacetyl)-1,3-oxazole
and
2,2-Dimethyl-5-methoxy-3-(dichloroacetyl)-1,3-oxazole.

Still another preferred group of antidotal compounds are the following which have a structure not according to Formula II:

α-[(Cyanomethoxy)imino]benzeneacetonitrile,
α-[(1,3-Dioxolan-2-yl-methoxy)imino]benzeneacetonitrile,
O-[1,3-Dioxolan-2-ylmethyl]-2,2,2-trifluoromethyl-4'-chloroacetophenone oxime,
Benzenemethamine, N-[4-(dichloromethylene)-1,3-ditholan-2-ylidene]-α-methyl, hydrochloride,
Diphenylmethoxy acetic acid, methyl ester,
1,8-Naphthalic anhydride,
4,6-Dichloro-2-phenyl-pyrimidine,
2-Chloro-N-[1-(2,4,6-trimethylphenyl)-ethenyl]acetamide,
Ethylene glycol acetal of 1,1-dichloroacetone,
1,3-Dioxolane, 2-(dichloromethyl)-2-methyl-, 5-Thiazolecarboxylic Acid, 2-chloro-4-(trifluoromethyl)-, (phenylmethyl)-ester, Phosphorothioic acid, O,O-diethyl O-(3-methylphenyl) ester, 4-Pentenenitrile, 2-methyl-2-[(4-methylphenyl)thio]-, 5-Chloro-8-(cyanomethoxy)quinoline, 1-Methylhexyl-2-(5-chloro-8-quinolinoxy)-acetate or O-(Methoxycarbonyl)-2-(8-quinolinoxy)-acetamide oxime.

The herbicidal and antidotal compounds of Formulae I–V are known in the art. The sub-group of 1,3-oxazolidine dichloroacetamides of Formula III are the subject of copending application, Ser. No. 07/212,621, of common assignment herewith, priority application for EP 304409 published Feb. 22, 1989.

The term "haloalkyl" embraces radicals wherein any one or more of the carbon atoms, preferably from 1 to 4 in number, is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are perhaloalkyl groups such as trifluoromethyl and perfluoroethyl groups.

Where in Formulae III–V the halogen attached to the acetyl radical is the chlorine ion, it is contemplated that the other halogens, i.e., bromo, iodo or fluoro may be substituted for the chloro.

Preferred haloalkyl $R_{13}$ members of Formula II are dihalomethyl, particularly dichloromethyl, while the preferred haloalkyl $R_{14}$ member is a trihalogenated methyl radical, preferably trifluoromethyl.

Where the term "alkyl" is used either alone or in compound form (as in "haloalkyl"), it is intended to embrace linear or branched radicals having up to four carbon atoms, the preferred members being methyl and ethyl.

By "agriculturally-acceptable salts" of the compounds defined by the above formula is meant a salt or salts which readily ionize in aqueous media to form a cation or anion of said compounds and the corresponding salt anion or cation, which salts have no deleterious effect on the antidotal properties of said compounds or of the herbicidal properties of a given herbicide and which permit formulation of the herbicide-antidote composition without undue problems of mixing, suspension, stability, applicator equipment use, packaging, etc.

By "antidotally-effective" is meant the amount of antidote required to reduce the phytotoxicity level or effect of a herbicide, preferably by at least 10% or 15%, but naturally the greater the reduction in herbicidal injury the better.

By "herbicidally-effective" is meant the amount of herbicide required to effect a meaningful injury or destruction to a significant portion of affected undesirable plants or weeds. Although of no hard and fast rule, it is desirable from a commercial viewpoint that 80–85% or more of the weeds be destroyed, although commercially significant suppression of weed growth can occur at much lower levels, particularly with some very noxious, herbicide-resistant plants.

The terms "antidote", "safening agent", "safener", "antagonistic agent", "interferant", "crop protectant" and "crop protective", are often-used terms denoting a compound capable of reducing the phytotoxicity of a herbicide to a crop plant or crop seed. The terms "crop protectant" and "crop protective" are sometimes used to denote a composition containing as the active ingredients, a herbicide-antidote combination which provides protection from competitive weed growth by reducing herbicidal injury to a valuable crop plant while at the same time controlling or suppressing weed growth occurring in the presence of the crop plant. Antidotes protect crop plants by interfering with the herbicidal action of a herbicide on the crop plants so as to render the herbicide selective to weed plants emerging or growing in the presence of crop plants.

Herbicides which may be used as co-herbicides with the azolopyrimidine sulfonamides of Formula I with benefit in combination with an antidote as described herein include, preferably, thiocarbamates (including dithiocarbamates), α-haloacetamides, (described above) heterocyclyl phenyl ethers (especially phenoxypyrazoles), imidazolinones, pyridines and sulfonylureas. It is within the purview of this invention that many other classes of herbicides, e.g., triazines, ureas, diphenyl ethers, nitroanilines, thiazoles, isoxazoles, pyrrolidinones, aromatic and heterocyclic di- and triketones, etc., the individual members of which classes may be derivatives having one or more substituents selected from a wide variety of radicals may suitably be used as co-herbicides. Such combinations can be used to obtain selective weed control with low crop injury in several varieties of monocotyledonous crop plants such as corn, grain sorghum (milo), and cereals such as wheat, rice, barley, oats, and rye, as well as several varieties of dicotyledonous crop plants including oil-seed crops such as soybeans and cotton. Particular utility for the antidotal compounds of this invention has been experienced with various herbicides in corn, sorghum and soybeans.

Examples of important thiocarbamate herbicides are the following:

cis-/trans-2,3-dichloroallyl-diisopropyl-thiolcarbamate (common name "diallate");

Ethyl dipropylthiocarbamate (common name "EPTC");

S-ethyl diisobutyl (thiocarbamate) (common name "butylate");

S-propyl dipropyl(thiocarbamate) (common name "vernolate");

2,3,3-trichloroallyl-diisopropylthiocarbamate (common name "triallate").

Examples of important acetamide herbicides are the following:

2-chloro-N-isopropylacetanilide (common name "propachlor");

2-chloro-1',6'-diethyl-N-(methoxymethyl)-acetanilide (common name "alachlor");

2-chloro-2',6'-diethyl-N-(butoxymethyl)-acetanilide (common name "butachlor");

2-chloro-N-(ethoxymethyl)-6'-ethyl-o-acetotoluidide (common name "acetochlor");

Ethyl ester of N-chloroacetyl-N-(2,6-diethylphenyl) glycine (common name "diethatyl ethyl");

2-chloro-N-(2,6-dimethylphenyl)-N-(2-methoxyethyl) acetamide (common name "dimethachlor");

2-chloro-N-(2-n-propoxyethyl)-2',6'-diethylacetanilide (common name "pretilachlor");

2-chloro-N-(2-methoxy-1-methylethyl)-6'-ethyl-o-acetotoluidide (common name "metolachlor");

2-chloro-2',6'-dimethyl-N-(1-pyrazol-1-yl-methyl) acetanilide (common name "metazachlor");

2-chloro-N-(2,6-dimethyl-1-cyclohexen-1-yl)-N-(1H-pyrazol-1ylmethyl)acetamide;

2-chloro-N-isopropyl-1-(3,5,5-trimethylcyclohexen-1-yl) acetamide (common name "trimexachlor");

2-Chloro-2'-methyl-6'-methoxy-N-(isopropoxymethyl) acetanilide;

2-Chloro-2'-methyl-6'-trifluoromethyl-N-(ethoxymethyl) acetanilide.

N-(2,4-dimethylthien-3-yl)-N-(1-methoxyprop-2-yl)-2-chloroacetamide;

N-(1H-pyrazol-2-ylmethyl)-N-(2,4-dimethylthien-3-yl)-2-chloroacetamide and

N-(1-pyrazol-1-ylmethyl)-N-(4,6-dimethoxypyrimidin-5-yl)-2-chloroacetamide.

Examples of important pyridine herbicides include:

3-pyridinecarboxylic acid,-2(difluoromethyl)-5-4,5-dihydro-2-thiazolyl-4-(2-methylpropyl)-6-(trifluoromethyl)-, methyl ester;

3-pyridinecarboxylic acid, 2-(difluoromethyl)-4-(2-methylpropyl)-5-(1H-pyrazol-1-ylcarbonyl)-6-(trifluoromethyl)-, methyl ester;

3,5-pyridinedicarboxylic acid, 2-(difluoromethyl)-4-(2-methylpropyl)-6-trifluoromethyl, dimethyl ester.

3,5-pyridine dicarbothioic acid, 2-(difluoromethyl)-4-(2-methylpropyl)-6-(trifluoromethyl)-, S,S-dimethyl ester.

Examples of important heterocyclyl phenyl ethers include:

5-(trifluoromethyl)-4-chloro-3-(3'-[1-ethoxycarbonyl]-ethoxy-4'-nitrophenoxy)-1-methylpyrazole;

5-(trifluoromethyl)-4-chloro-3-(3'-methoxy-4'-nitrophenoxy)-1-methylpyrazole;

5-(trifluoromethyl)-4-chloro-3-(3'-[1-butoxycarbonyl]-ethoxy-4'-nitrophenoxy)-4-methylpyrazole;

5-(trifluoromethyl)-4-chloro-3-(3'-methylsulfamoylcarbonyl propoxy-4'-nitrophenoxy)-4-methylpyrazole;

5-(trifluoromethyl)-4-chloro-3-(3'-propoxycarbonylmethyloxime-4'-nitrophenoxy)-1-methylpyrazole;

(±)-2-(4-[[5-(trifluoromethyl)-2-pyridinyl]-oxy]phenoxy] propanoic acid.

Examples of important sulfonylureas include:

Benzenesulfonamide, 2-chloro-N-[[(4-methoxy-6-methyl-1,3,5-triazin-2-yl)amino]-carbonyl], (common name "chlorsulfuron");

Benzoic acid, 2-[[[[(4-chloro-6-methoxy-2-pyrimidin-2-yl)amino]carbonyl]amino]-sulfonyl]-ethyl ester, (common name "chlormuron ethyl");

2-Thiophenecarboxylic acid, 3-[[[[(4,6-dimethoxy-1,3,5-triazin-2-yl)amino]-carbonyl]-amino]sulfonyl]-, methyl ester (code No. DPX-M6316);

Benzoic acid, 2-[[[[(4,6-dimethyl-2-pyrimidinyl)amino] carbonyl]amino]sulfonyl]-methyl ester (common name "sulfometuron methyl");

Benzenesulfonamide, 2-(2-chloroethoxy)-N-[[(4-methoxy-6-methyl-1,3,5-triazin-2-yl)amino]-carbonyl] (common name "triasulfuron");

Benzoic acid, 2-[[[[(4-methoxy-6-methyl-1,3,5-triazin-2-yl)amino]carbonyl]-amino]sulfonyl]-methyl ester (common name "metsulfuron methyl");

Benzoic acid, 2-[[[[[4,6-bis(difluoromethoxy)-2-pyrimidin-2-yl]amino]-carbonyl]amino]sulfonyl]methyl ester; (common name "primisulfuron")

Pyridine, 3-[[[[(4,6-dimethyl-2-pyrimidin-2-yl)amino] carbonyl]amino]sulfonyl]-N,N-dimethylcarbamoyl, (common name "nicosulfuron");

Pyridine, 3-[[[[(4,6-dimethoxy-2-pyrimidin-2-yl)amino] carbonyl]amino]sulfonyl]-ethylsulfonyl, (code number "DPX E9636");

Benzenesulfonamide, 2-(methoxyethoxy)-N-[[(4,6-dimethoxy-1,3,5-traizin-2-yl)amino]carbonyl], (common name "cinosulfuron")

Methyl-2-[[[[[(4,6-dimethoxy-2-pyrimidin-2-yl)amino] carbonyl]amino]sulfonyl]-methyl]benzoate, (common name "bensulfuron methyl");

N-[(4,6-dimethoxypyrimidin-2-yl)aminocarbonyl]-3-chloro-4-methoxycarbonyl-1-methoxycarbonyl-1-methylpyrazole, (code number "NC-319";

N-[(4,6-dimethoxypyrimidin-2-yl)aminocarbonyl]-4-ethoxycarbonyl-1-methylpyrazole, (code number "NC-311");

N-[(4,6-dimethylpyrimidin-2-yl)aminocarbonyl]-1-(1-methylethyl)-1H-imidazole-2-sulfonamide;

N-[(4-methoxy-6-methylpyrimidin-2-yl)-aminocarbonyl] -1-(1-methylethyl)-1H-imidazole-2-sulfonamide;

N-[(4,6-dimethoxypyrimidin-2-yl)aminocarbonyl]-1-(1-methylethyl)-1H-imidazole-2-sulfonamide;

N-[(4,6-dimethylpyrimidin-2-yl)aminocarbonyl]-1-ethyl-1H-imidazole-2-sulfonamide;

N-[(4-methoxy-6-methylpyrimidin-2-yl)-aminocarbonyl] -1-ethyl-1H-imidazole-2-sulfonamide;

N-[(4,6-dimethoxypyrimidin-2-yl)aminocarbonyl]-1-ethyl-1H-imidazole-2-sulfonamide;

N-[(4,6-dimethoxypyrimidin-2-yl)aminocarbonyl]-5-bromo-1-methyl-1H-imidazole-4-sulfonamide.

Examples of important imidazolinone herbicides include:

3-Quinolinecarboxylic acid, 2-[4,5-dihydro-4-methyl-4-(1-methylethyl)-5-oxo-1H-imidazol-2-yl)-;

3-Pyridinecarboxylic acid, 2-[4,5-dihydro-4-methyl-4-(1-methylethyl)-5-oxo-1H-imidazol-2-yl]-;

Benzoic Acid, 2-[4,5-dihydro-4-methyl-4-(1-methylethyl)-5-oxo-1H-imidazol-2-yl]-4(or 5)-methyl;

3-pyridinecarboxylic acid, 5-ethyl-2-[4-methyl-4-(1-methylethyl)-5-oxo-1H-imidazol-2-yl]-;

3-pyridinecarboxylic acid, 2-[4,5-dihydro-4-methyl-4-(1-methylethyl)-5-oxo-1H-imidazol-2-yl]-5-methyl-, ammonium salt;

2-(5-Methyl-5-trifluoromethyl-1-H-imidazol-4-on-2-yl)-pyridin-3-carboxylic acid;

2-(5-Methyl-5-trifluoromethyl-1-H-imidazol-4-on-2-yl) 5-(m)ethyl isonicotinic acid;

2-[5-(1-Fluoroethyl)-5-(m)ethyl-H-imidazol-4-on-2-yl] isonicotinic acid;

2-(5-(Difluoromethyl-5-(m)ethyl-1-H-imidazol-4-on-2-yl]-5-(m)ethylisonicotinic acid;

2-(5-(1-Fluoroethyl)-5-(m)ethyl)-imidazol-4-on-2-yl] isonicotinic (m)ethyl ester;

Examples of important benzoic acid derivative herbicides include:

3,6-Dichloro-2-methoxybenzoic acid (common name "dicamba"), 2,5-Dichloro-3-aminobenzoic acid (common name "amiben" and "chloramiben"), 5-(2'-Chloro-4'-trifluoromethylphenoxy)-2-nitrobenzoic acid (common name "acifluorfen"), 2,6-Dichlorobenzonitrile (common name "dichlobenil"), 3,5,6-Trichloro-2-methoxybenzoic acid (common name "Tricamba"), 2,3,6-Trichlorobenzoic acid, and 2,3,5,6-Tetrachlorobenzoic acid, and salts, esters and amides of the above acids.

Examples of other important herbicides include:

2-Chloro-4-(ethylamino)-6-(isopropylamino)-s-triazine;

4-Amino-6-tertbutyl-3-(methylthio)as-triazine-5(4H)one;

Trifluoro-2,6-dinitro-N,N-dipropyl-p-toluidine;

Benzeneamine, N-(1-ethylpropyl)-3,4-dimethyl-2,6-dinitro-;

2-Pyrrolidinone, 3-chloro-4-(chloromethyl)-1-[3-(trifluoromethyl)phenyl], trans-;

3-Isoxazolidinone, 2-[(2-chlorophenyl)-methyl]-4,4-dimethyl-;

2-Imidazolidinone, 3-[5-(1,1-dimethylethyl)-3-isoxazolyl]-4-hydroxy-1-methyl-;

2-Chloro-4-(1-cyano-1-methylethylamino)-6-ethylamino-1,3,5-triazine;

Methyl 5-(2,4-dichlorophenoxy)-2-nitrobenzoate;

1'-(Carboethoxy)ethyl-5-[2-chloro-4-(trifluoromethyl)phenoxy]-2-nitrobenzoate;

Ammonium-DL-homoalanin-4-yl(methyl)-phosphinate;

1-[(2-Fluoro-4-chloro-5-(2,3-dimethylbutoxyphenyl0] tetrahydrophthalimide and 2-(3,4-Dichlorophenyl)-4-methyl-1,2,4-oxadiazolidine-3,5-dione.

The herbicides of particular and preferred interest as co-herbicides with the azolopyrimidine sulfonamides of Formula I in compositions with antidotes according to this invention include each of the abovementioned species from different chemical classes of compounds exemplified as important herbicides, particularly those of current commercial interest and use and those which may be determined of commercial utility.

Co-herbicidal compounds of preference include the following:

alachlor,
acetochlor,
butachlor,
metolachlor,
pretilachlor
metazachlor,
2-chloro-2',6'-dimethyl-N-(2-methoxyethyl)-acetanilide,
butylate and combinations thereof with the commercial antidotes R-29148 or PPG-1292 and EPTC and combinations thereof with the commercial antidotes R-25788, R-29148 or PPG-1292 any of which may further contain an extender, e.g., dietholate.

All of the above specifically-named antidotes and herbicides are known in the art.

As further detailed infra, while not necessary, the composition containing the herbicide-antidote combination may also contain other additaments, e.g., biocides such as insecticides, fungicides, nematocides, miticides, etc., fertilizers, inert formulation aids, e.g., surfactants, emulsifiers, defoamers, dyes, extenders, etc.

Combinations may be made of any one or more of the described antidote compounds with any one or more of the herbicide compounds of Formula I and co-herbicides mentioned herein.

It will be recognized by those skilled in the art that all herbicides have varying degrees of phytotoxicity to various plants because of the sensitivity of the plant to the herbicide. Thus, e.g., although certain crops such as corn and soybeans have a high level of tolerance (i.e., low sensitivity) to the phytotoxic effect of alachlor, other crops, e.g., milo (grain sorghum), rice and wheat, have a low level of tolerance (i.e., high sensitivity) to the phytotoxic effects of alachlor. The same type of sensitivity to herbicides as shown by crop plants is also exhibited by weeds, some of which are very sensitive, others very resistant to the phytotoxic effects of the herbicide.

When the sensitivity of a crop plant to a herbicide is low, whereas the sensitivity of a weed to that herbicide is high, the "selectivity factor" of the herbicide for preferentially injuring the weed while not injuring the crop is high.

In an analogous manner, but more complex, an antidotal compound may, and commonly does, have varying degrees of crop protective effect against different herbicides in different crops. Accordingly, as will be appreciated by those skilled in the art, the various antidotes of this invention, as with all classes of antidotal compounds, will have greater or lesser crop safening effects against various herbicides in various crops than in others. Thus, while a given antidotal compound may have no crop protective ability against a given herbicide in a given crop, that same antidotal compound may have a very high crop protective ability against the same given herbicide in a different crop or against a different herbicide in the same crop. This is an expected phenomenon.

DETAILED DESCRIPTION OF THE INVENTION

Antidote Compounds

As mentioned earlier, the antidotal compounds used in the practice of this invention are known compounds. The preferred compounds used herein are the 1,3-oxazolidine dichloroacetamides according to Formula III wherein the $R_{17}$ member is a heterocyclic radical. Those compounds and synthesis methods therefor are separately disclosed and claimed in the assignee's said copending application, Ser. No. 07/212,621 and its corresponding EP 304409, published Feb. 22, 1989.

Biological Evaluation

Effective weed control coupled with low crop injury is a result of treatment of a plant locus with a combination of herbicide compound and antidote compound. By application to the "plant locus" is meant application to the plant growing medium, such as soil, as well as to the seeds, emerging seedlings, roots, stems, leaves, or other plant parts.

The phrase "combination of herbicide compound and antidote compound" embraces various methods of treatment. For example, the soil of a plant locus may be treated with a "tank-mix" composition containing a mixture of the herbicide and the antidote which is "in combination". Or, the soil may be treated with the herbicide and antidote compounds separately so that the "combination" is made on, or in, the soil. After such treatments of the soil with a mixture of herbicide and antidote or by separate or sequential application of the herbicide and antidote to the soil, the herbicide and antidote may be mixed into or incorporated into the soil either by mechanical mixing of the soil with implements or by "watering in" by rainfall or irrigation. The soil of a plant locus may also be treated with antidote by application of the antidote in a dispersible-concentrate form such as a granule. The granule may be applied to a furrow which is prepared for receipt of the crop seed and the herbicide may be applied to the plant locus either before or after in-furrow placement of the antidote-containing granule so that the herbicide and antidote form a "combination". Crop seed may be treated or coated with the antidote compound either while the crop seed is in-furrow just after seeding or, more commonly, the crop seed may be treated or coated with antidote prior to seeding into a furrow. The herbicide may be applied to the soil plant locus before or after seeding and a "combination" is made when both herbicide and antidote-coated seed are in the soil. Also contemplated as a "combination" is a commercially-convenient association or presentation of herbicide and antidote. For example, the herbicide and antidote components in concentrated form may be contained in separate containers, but such containers may be presented for sale or sold together as a "combination" (composition). Or, the herbicide and antidote components in concentrated form may be in a mixture in a single container as a "combination". Either such "combination" may be diluted or mixed with adjuvants suitable for soil applications. Another example of a commercially-presented combination is a container of antidote-coated crop seed sold, or presented for sale, along with a container of herbicide material. These containers may, or may not, be physically attached to each other, but nonetheless constitute a "combination of herbicide and antidote" when intended for use ultimately in the same plant locus.

In the foregoing description of various modes of application of the herbicide-antidote combinations, it is inherent that each form of application requires that in some manner, the herbicide and antidote will physically combine to form a "composition" of those agents.

The amount of antidote employed in the methods and compositions of the invention will vary depending upon the particular herbicide with which the antidote is employed, the rate of application of the herbicide, the particular crop to be protected, and the manner of application to the plant locus. In each instance the amount of antidote employed is a safening-effective amount, that is, the amount which reduces, or protects against, crop injury that otherwise would result from the presence of the herbicide. The amount of antidote employed will be less than an amount that will substantially injure the crop plant.

The antidote can be applied to the crop plant locus in a mixture with the selected herbicide. For example, where the crop seed is first planted, a suitable mixture of antidote and herbicide, whether in a homogeneous liquid, emulsion, suspension or solid form, can be applied to the surface of, or incorporated in, the soil in which the seed has been planted. Or, the herbicide-antidote mixture may be applied to the soil, and then the seed thereafter "drilled" into the soil below the soil layer containing the herbicide-antidote mixture. The herbicide will reduce or eliminate the presence of undesirable weed plants. Where the herbicide would by itself injure the crop seedlings, the presence of the antidote will reduce or eliminate the injury to the crop seed caused by the herbicide. It is not essential that the application of herbicide and the antidote to the plant locus be made using the selected herbicide and antidote in the form of a mixture or composition. The herbicide and the antidote may be applied to the plant locus in a sequential manner. For example, the antidote may be first applied to the plant locus and thereafter the herbicide is applied. Or, the herbicide may be first applied to the plant locus and thereafter the antidote is applied.

The ratio of herbicide to antidote may vary depending upon the crop to be protected, weed to be inhibited, herbicide used, etc., but normally a herbicide-to-antidote ratio ranging from 1:25-to-60:1 (preferably 1:5-to-30:1) parts by weight may be employed, although much higher rates of antidote may be used, e.g., 1:100–1:300 parts by weight of herbicide-to-antidote. As indicated above, the antidote may be applied to the plant locus in a mixture, i.e., a mixture of a herbicidally-effective amount of herbicide and a safening-effective amount of an antidote, or sequentially, i.e., the plant locus may be treated with an effective amount of the herbicide followed by a treatment with the antidote or vice versa. In general, effective herbicidal amounts are in the range of about 0.03 to about 12 kilograms/hectare, but rates as low as 0.004 kg/ha may be used effectively. The preferred range of rate of application is from about 0.1 to about 10 kg/ha. Preferably, antidote application rates range from about 8–10 kg/ha down to about 0.05 kg/ha. It will be appreciated that at times amounts either below or above these ranges will be necessary to obtain the best results. The selection of the herbicide to inhibit the emergence and growth of weeds depends upon the species of weeds to be controlled and the crop to be protected.

The application of the antidote can be made directly to the seed before planting. In this practice, a quantity of crop seed is first coated with the antidote. The coated seed is thereafter planted. The herbicide may be applied to the soil before or after the coated seed is planted.

In field applications, the herbicide,. antidote, or a mixture thereof, may be applied to the plant locus without any adjuvants other than a solvent. Usually, the herbicide, antidote, or a mixture thereof, is applied in conjunction with one or more adjuvants in liquid or solid form. Compositions or formulations containing mixtures of an appropriate herbicide and antidote usually are prepared by admixing the herbicide and antidote with one or more adjuvants such as diluents, solvents, extenders, carriers, conditioning agents, water, wetting agents, dispersing agents, or emulsifying agents, or any suitable combination of these adjuvants. These mixtures may be in the form of particulate solids, granules, pellets, wettable powders, dusts, solutions, aqueous dispersions, or emulsions.

Application of the herbicide, antidote, or mixture thereof, can be carried out by conventional techniques utilizing, for example, hand-carried or tractor-mounted spreaders, power dusters, boom and hand sprayers, spray dusters, and granular applicators. If desired, application of the compositions of the invention to plants can be accomplished by incorporating the compositions in the soil or other media.

Evaluations of safening activity of a wide variety of representative antidote compounds of this invention were carried out using the specific procedure of Example 1 below in greenhouse testing. Measurements of biological response as reported in Tables 1–3 were made in the following manner. A visual comparison was made between a crop plant treated with a herbicide alone and crop plant having no herbicide or antidote treatment. A number was assigned to this visual comparison indicating the percent injury or inhibition to the herbicide-alone treated crop plant (column "WO" in the tables indicating herbicide "without" antidote). Also, a visual comparison was made between the crop plant treated with herbicide+antidote combination and the crop plant having no herbicide or antidote treatment. A number was assigned to this visual comparison indicating the percent injury or inhibition to the herbicide+antidote treated crop plant (column "W" in the tables indicating herbicide "with" antidote). Observations of response by the weed species to herbicide or herbicide+antidote were similarly recorded. The degree of reduction of herbicide injury provided by an antidote compound is indicated by the magnitude that the plant inhibition number of column "WO" exceeds the corresponding number of column "W". Also reported in the tables are data in parenthesis showing "safening effect" (defined below) for the herbicide+antidote combinations calculated from the plant inhibition numbers. These tables may show crop or weed column headings under which there are no data. The lack of such data is an indication of a failed test or that the particular herbicide+antidote rate combination was not tested with any crop or weed.

Listed below are the names of the antidotal compounds of preference herein and representative ones therein for which data are reported in the tables.

| Antidote No. | Nomenclature |
| --- | --- |
| 1 | 4-Pentenenitrile, 2-methyl-2-[(4-methylphenyl)thio], |
| 2 | Acetic acid, (diphenylmethoxy)-, methyl ester, |
| 3 | Benzenemethanamine, N-[4-(dichloromethylene)-1,3-dithiolan-2-ylidene]-α-methyl, hydrochloride, |
| 4 | Phosphorothioic acid, O,O-diethyl-O-(3-methylphenyl) ester, |
| 5 | 5-Thiazolecarboxylic acid, 2-chloro-4-(trifluoromethyl)-, (phenylmethyl ester), |
| 6 | Pyrimidine, 4,6-dichloro-2-phenyl-, |
| 7 | 1H, 3H-Naphtho[1,8-cd]pyran-1,3-dione, |
| 8 | Benzeneacetonitrile, α-{[(1,3-dioxolan-2-yl)methoxy]imino}-, |
| 9 | Acetamide, N,N-Bis(2-propenyl)-α,α-dichloro, (also, N,N-diallyl dichloroacetamide), |
| 10 | Oxazolidine, 3-(dichloroacetyl)-5-(2-furanyl)-2,2-dimethyl-, |
| 11 | Cis/Trans-piperazine, 1,4-bis(dichloroacetyl)-2,5-dimethyl, |
| 12 | 1-Oxa-4-azaspiro[4.5]decane, 4-(dichloroacetyl)-, (also, 4-dichloroacetyl-1-oxa-4-azaspiro-(4,5)decane), |
| 13 | Oxazolidine, 3-(dichloroacetyl)-2,2,5-trimethyl, |
| 14 | Oxazolidine, 3-(dichloroacetyl)-2,2-dimethyl, |
| 15 | Acetamide, 2,2-dichloro-N-(1,3-dioxolan-2-yl-methyl)-N-2-propenyl, |
| 16 | Ethanone, 2,2-dichloro-1-(1,2,3,4-tetrahydro-1-methyl-2-isoquinolinyl, |
| 17 | 1,3-Dioxolane, 2-(dichloromethyl)-2-methyl-, |
| 18 | 5-Chloro-8-(cyanomethoxy)quinoline, |
| 19 | 1-Methylhexyl-2-(5-chloro-8-quinolinoxy)acetate, |
| 20 | O-(Methoxycarbonyl)-2-(8-quinolinoxy)-acetamide oxime, |
| 21 | 4-(Dichloroacetyl)-2,3-dihydro-3-methyl-2H-1,4-benzoxazine. |

The following lists identify the herbicides and co-herbicides used in tests, the data for which is reported in the tables below:

| Herbicide No. | Nomenclature |
| --- | --- |
| 1 | 5,7-Dimethyl-N-(2,6-dichloro-3-methyl-phenyl)-1,2,4-triazolo[1,5-a]pyrimidine-2-sulfonamide, |
| 2 | 5-Methyl-N-(2,6-difluorophenyl)-1,2,4-triazolo-[1,5-a]-pyrimidine-2-sulfonamide, |
| 3 | 5,7-Dimethyl-N-(2-nitrophenyl)-1,2,4-triazolo-[1,5-a]-pyrimidine-2-sulfonamide, |
| 4 | 5,7-Dimethyl-N-[2-methoxy-6-(trifluoromethyl)phenyl]-1,2,4-triazolo-[1,5-a]-pyrimidine-2-sulfonamide, |
| 5 | 5-Methyl-7-ethoxy-N-(2,6-dichloro-3-methylphenyl)-1,2,4-triazolo-[1,5-a]-pyrimidine-2-sulfonamide, |
| 6 | N-(2,6-Difluorophenyl)-3-chloro-4,6-dimethylimidazolo-[1,2-a]-pyrimidine-2-sulfonamide, |
| 7 | N-(5,7-Dimethyl-1,2,4-triazolo-[1,5-a]-pyrimidin-2-yl)-2,6-dichlorophenyl-2-sulfonamide, |
| 8 | 5-Fluoromethyl-7-methoxy-N-(2,6-dichlorophenyl)-1,2,4-triazolo-[1,5-a]-pyrimidine-2-sulfonamide, |
| 9 | 5-Methoxy-7-fluoro-N-(2,6-difluorophenyl)-1,2,4-triazolo-[1,5-c]-pyrimidine-2-sulfonamide. |

| Co-Herbicide | Nomenclature |
| --- | --- |
| A | 2-Chloro-N-(ethoxymethyl)-6'-ethyl-o-acetotoluidide ("acetochlor"), |
| B | 2-Chloro-N-(2-methoxy-1-methylethyl)-6'-ethyl-o-acetotoluidide ("metolachlor"), |
| C | S-Ethyl-bis(2-methylpropyl)carbamothioate ("butylate"), |
| D | S-ethyl dipropylcarbamothioate, (common name "EPTC"), |
| E | N,N-Dimethyl-N'-[4-(1-methylethyl)-phenyl]urea, (common name "isoproturon"), |
| F | Benzoic acid, 2-[[[[[4,6-bis(difluoromethoxy)-2-pyrimidin-2-yl]amino]-carbonyl]amino]sulfonyl]methyl ester, (common name "primisulfuron"), |
| G | 2-Chloro-1',6'-diethyl-N-(methoxymethyl)acetanilide, (common name "alachlor"), |
| H | 2-Chloro-1',6'-diethyl-N-(butoxymethyl)acetanilide, (common name "butachlor"). |

In the foregoing lists, azolopyrimidine sulfonamide No. 2 in combination with Antidote Nos. 9, 10, 12, 13, 15 and 18–20 and with or without Co-herbicides A, B or C are particularly preferred.

EXAMPLE 1

The following procedure shows interaction between herbicide and antidote when both are incorporated in a soil cover layer before emergence of crop and weed species. Containers were filled and compacted with a fumigated silt loam top soil to a depth of about 1.3 cm from the top of the container. A first container was designated as an untreated control, a second container was designated as a herbicide control, and a third container was designated as a herbicide+antidote test container. Each of the containers was seeded with a crop species. A measured amount of each herbicide dispersed or dissolved in acetone or water was applied to a measured quantity of soil. To this same quantity of soil treated with herbicide, there was added a measured amount of antidote dispersed or dissolved in acetone or water. The quantity of soil treated with the herbicide and antidote was thoroughly mixed to incorporate the herbicide and antidote in the soil uniformly. The seed bed in the third container of soil was covered with the soil treated with the herbicide and antidote and the container was leveled. For each test series, the seed beds of the first and second containers were likewise covered by soil layers. The cover layer of the first container was not treated with herbicide or antidote. The cover layer of the second container had a measured quantity of herbicide alone incorporated therein. Each container received 0.6 mm of overhead irrigation. The containers were then placed on a bench in a greenhouse and sub-irrigated as required for the duration of the test. Plant response was observed about three weeks after initial treatment.

In the tables below, the rates of application of herbicides and antidotes are given in kilograms/hectare and, as noted above, the following symbols have the indicated meaning:

W=% Plant Inhibition caused by combination of herbicide and antidote.

WO=% Plant Inhibition caused by herbicide alone.

Data reported in parentheses=% Safening Effect.

$$(\_) = \frac{WO - W}{WO} \times 100$$

In this test, Antidote Nos. 1–12 were tested against Herbicide Nos. 1–5 in a plurality of crops, i.e., corn, grain sorghum, soybeans, wheat and rice, in the presence of the weeds, yellow foxtail and velvetleaf, having the symbols "YEFT" and "VELE", respectively. Results are reported in Table 1.

TABLE 1

| HERB. | | ANTI-DOTE | | % PLANT INHIBITION AND % SAFENING EFFECT ( ) | | | | | | | | | | | | | |
|---|---|---|---|---|---|---|---|---|---|---|---|---|---|---|---|---|---|
| | | | | CORN | | SORGHUM (GRAIN) | | SOYBEAN | | WHEAT | | RICE | | YEFT | | VELE | |
| NO. | RATE | NO. | RATE | W | WO | W | WO | W | WO | W | WO | W | WO | W | WO | W | WO |
| 1 | 2.24 | | | | 15 | | 85 | | 90 | | 30 | | 30 | | 60 | | 45 |
| 1 | 0.56 | | | | 0 | | 75 | | 80 | | 35 | | 25 | | 40 | | 45 |
| 1 | 0.14 | | | | 0 | | 20 | | 70 | | 10 | | 10 | | 20 | | 35 |
| 1 | 2.24 | 1 | 2.24 | 25 (0) | 60 | 60 (29) | | 80 (11) | | 25 (17) | | 15 (50) | | 60 (0) | | 45 (0) | |
| 1 | 0.56 | 1 | 2.24 | 10 (0) | | 35 (53) | | 80 (0) | | 10 (71) | | 15 (40) | | 50 (0) | | 45 (0) | |
| 1 | 0.14 | 1 | 2.24 | 10 (0) | | 20 (0) | | 80 (0) | | 0 (100) | | 0 (100) | | 20 (0) | | 30 (14) | |
| 1 | 2.24 | 2 | 2.24 | 25 (0) | | 60 (29) | | 80 (11) | | 15 (50) | | 20 (33) | | 45 (25) | | 45 (0) | |
| 1 | 0.56 | 2 | 2.24 | 15 (0) | | 20 (73) | | 80 (0) | | 10 (71) | | 10 (60) | | 40 (0) | | 35 (22) | |
| 1 | 0.14 | 2 | 2.24 | 10 (0) | | 10 (50) | | 75 (0) | | 10 (0) | | 0 (100) | | 40 (0) | | 30 (14) | |
| 1 | 2.24 | 3 | 2.24 | 10 (33) | | 70 (18) | | 80 (11) | | 30 (0) | | 23 (17) | | 55 (8) | | 45 (0) | |
| 1 | 0.56 | 3 | 2.24 | 0 (0) | | 30 (60) | | 80 (0) | | 25 (29) | | 15 (40) | | 50 (0) | | 35 (22) | |
| 1 | 0.14 | 3 | 2.24 | 0 (0) | | 25 (0) | | 75 (0) | | 15 (0) | | 0 (100) | | 45 (0) | | 30 (0) | |
| 1 | 2.24 | 4 | 2.24 | 23 (0) | | 70 (18) | | 85 (5) | | 40 (0) | | 45 (0) | | 80 (0) | | 50 (0) | |
| 1 | 0.56 | 4 | 2.24 | 10 (0) | | 30 (60) | | 75 (6) | | 40 (0) | | 25 (0) | | 65 (0) | | 40 (11) | |
| 1 | 0.14 | 4 | 2.24 | 10 (0) | | 25 (0) | | 75 (0) | | 15 (0) | | 10 (0) | | 45 (0) | | 20 (43) | |
| 1 | 2.24 | 5 | 2.24 | 15 (0) | | 30 (65) | | 80 (11) | | 15 (50) | | 15 (50) | | 60 (0) | | 60 (0) | |
| 1 | 0.56 | 5 | 2.24 | 10 (0) | | 15 (80) | | 80 (0) | | 15 (57) | | 10 (60) | | 50 (0) | | 40 (11) | |
| 1 | 0.14 | 5 | 2.24 | 0 (0) | | 10 (50) | | 70 (0) | | 10 (0) | | 0 (100) | | 30 (0) | | 30 (14) | |
| 1 | 2.24 | 6 | 2.24 | 35 (0) | | 95 (0) | | 90 (0) | | 55 (0) | | 50 (0) | | 65 (0) | | 75 (0) | |
| 1 | 0.56 | 6 | 2.24 | 20 (0) | | 90 (0) | | 80 (0) | | 20 (43) | | 15 (40) | | 25 (38) | | 50 (0) | |
| 1 | 0.14 | 6 | 2.24 | 0 (0) | | 20 (0) | | 70 (0) | | 10 (0) | | 0 (100) | | 20 (0) | | 30 (14) | |
| 1 | 2.24 | 7 | 2.24 | 15 (0) | | 30 (65) | | 85 (5) | | 30 (0) | | 45 (0) | | 70 (0) | | 40 (11) | |
| 1 | 0.56 | 7 | 2.24 | 0 (0) | | 0 (100) | | 80 (0) | | 15 (57) | | 0 (100) | | 35 (13) | | 30 (33) | |
| 1 | 0.14 | 7 | 2.24 | 0 (0) | | 0 (100) | | 70 (0) | | 0 (100) | | 0 (100) | | 20 (0) | | 25 (29) | |
| 1 | 2.24 | 8 | 2.24 | 10 (33) | | 10 (88) | | 85 (5) | | 30 (0) | | 45 (0) | | 30 (50) | | 40 (11) | |
| 1 | 0.56 | 8 | 2.24 | 0 (0) | | 0 (100) | | 80 (0) | | 15 (57) | | 10 (60) | | 20 (50) | | 30 (33) | |
| 1 | 0.14 | 8 | 2.24 | 0 (0) | | 0 (100) | | 80 (0) | | 10 (0) | | 0 (100) | | 0 (100) | | 20 (43) | |
| 1 | 2.24 | 9 | 2.24 | 15 (0) | | 40 (53) | | 85 (6) | | 25 (17) | | 35 (0) | | 45 (25) | | 45 (0) | |
| 1 | 0.56 | 9 | 2.24 | 0 (0) | | 35 (53) | | 85 (0) | | 20 (43) | | 30 (0) | | 40 (0) | | 45 (0) | |
| 1 | 0.14 | 9 | 2.24 | 10 (0) | | 15 (33) | | 80 (0) | | 10 (0) | | 15 (0) | | 20 (0) | | 30 (14) | |
| 1 | 2.24 | 10 | 2.24 | 15 | | 20 | | 85 | | 25 | | 40 | | 50 | | 45 | |

TABLE 1-continued

% PLANT INHIBITION AND % SAFENING EFFECT ( )

| HERB. NO. | RATE | ANTI-DOTE NO. | RATE | CORN | SORGHUM (GRAIN) | SOYBEAN | WHEAT | RICE | YEFT | VELE |
|---|---|---|---|---|---|---|---|---|---|---|
| | | | | (0) | (76) | (6) | (17) | (0) | (17) | (0) |
| 1 | 0.56 | 10 | 2.24 | 10 (0) | 15 (80) | 80 (0) | 15 (57) | 20 (20) | 40 (0) | 35 (22) |
| 1 | 0.14 | 10 | 2.24 | 0 (0) | 0 (100) | 75 (0) | 0 (100) | 0 (100) | 35 (0) | 30 (14) |
| 1 | 2.24 | 11 | 2.24 | 10 (33) | 25 (71) | 85 (6) | 40 (0) | 40 (0) | 35 (42) | 45 (0) |
| 1 | 0.56 | 11 | 2.24 | 0 (0) | 30 (60) | 80 (0) | 40 (0) | 35 (0) | 20 (50) | 40 (11) |
| 1 | 0.14 | 11 | 2.24 | 0 (0) | 10 (50) | 75 (0) | 15 (0) | 0 (100) | 15 (25) | 30 (14) |
| 1 | 2.24 | 12 | 2.24 | 15 (0) | 45 (47) | 85 (6) | 15 (50) | 20 (33) | 70 (0) | 45 (0) |
| 1 | 0.56 | 12 | 2.24 | 10 (0) | 10 (87) | 80 (0) | 10 (71) | 15 (40) | 60 (0) | 40 (11) |
| 1 | 0.14 | 12 | 2.24 | 10 (0) | 0 (100) | 75 (0) | 0 (100) | 0 (100) | 25 (0) | 30 (14) |
| 2 | 1.12 | | | 70 | 100 | 75 | 70 | 95 | 98 | 80 |
| 2 | 0.28 | | | 30 | 99 | 70 | 20 | 20 | 70 | 50 |
| 2 | 0.07 | | | 10 | 60 | 45 | 15 | 10 | 60 | 35 |
| 2 | 1.12 | 1 | 2.24 | 80 (0) | 100 (0) | 85 (0) | 75 (0) | 90 (0) | 99 (0) | 80 (0) |
| 2 | 0.28 | 1 | 2.24 | 30 (0) | 100 (0) | 60 (14) | 30 (0) | 45 (0) | 90 (0) | 50 (0) |
| 2 | 0.07 | 1 | 2.24 | 0 (100) | 90 (0) | 35 (22) | 15 (0) | 10 (0) | 45 (25) | 30 (0) |
| 2 | 1.12 | 2 | 2.24 | 40 (43) | 100 (0) | 65 (13) | 60 (14) | 90 (5) | 95 (0) | 60 (25) |
| 2 | 0.28 | 2 | 2.24 | 10 (69) | 95 (0) | 45 (36) | 20 (0) | 30 (0) | 65 (7) | 40 (20) |
| 2 | 0.07 | 2 | 2.24 | 0 (100) | 70 (0) | 50 (0) | 0 (100) | 0 (100) | 40 (33) | 30 (14) |
| 2 | 1.12 | 3 | 2.24 | 45 (36) | 100 (0) | 65 (13) | 80 (0) | 99 (0) | 99 (0) | 65 (19) |
| 2 | 0.28 | 3 | 2.24 | 25 (17) | 100 (0) | 45 (36) | 45 (0) | 40 (0) | 85 (0) | 45 (10) |
| 2 | 0.07 | 3 | 2.24 | 0 (100) | 75 (0) | 40 (11) | 10 (33) | 0 (100) | 45 (25) | 35 (0) |
| 2 | 1.12 | 4 | 2.24 | 99 (0) | 100 (0) | 90 (0) | 95 (0) | 100 (0) | 100 (0) | 80 (0) |
| 2 | 0.28 | 4 | 2.24 | 90 (0) | 100 (0) | 60 (14) | 80 (0) | 80 (0) | 99 (0) | 60 (0) |
| 2 | 0.07 | 4 | 2.24 | 45 (0) | 100 (0) | 55 (0) | 60 (0) | 50 (0) | 95 (0) | 55 (0) |
| 2 | 1.12 | 5 | 2.24 | 45 (36) | 100 (0) | 70 (6) | 70 (0) | 95 (0) | 100 (0) | 75 (0) |
| 2 | 0.28 | 5 | 2.24 | 15 (50) | 98 (0) | 60 (14) | 40 (0) | 60 (0) | 75 (0) | 60 (0) |
| 2 | 0.07 | 5 | 2.24 | 0 (100) | 70 (0) | 45 (0) | 10 (30) | 0 (0) | 65 (0) | 40 (0) |
| 2 | 1.12 | 6 | 2.24 | 85 (0) | 100 (0) | 65 (13) | 65 (7) | 95 (0) | 95 (0) | 70 (13) |
| 2 | 0.28 | 6 | 2.24 | 35 (0) | 100 (0) | 55 (21) | 50 (0) | 70 (0) | 80 (0) | 65 (0) |
| 2 | 0.07 | 6 | 2.24 | 0 (100) | 85 (0) | 40 (11) | 15 (0) | 10 (0) | 15 (75) | 35 (0) |
| 2 | 1.12 | 7 | 2.24 | 35 (50) | 100 (0) | 75 (0) | 75 (0) | 90 (5) | 80 (18) | 80 (0) |
| 2 | 0.28 | 7 | 2.24 | 15 (50) | 99 (0) | 60 (0) | 35 (0) | 40 (0) | 55 (21) | 45 (10) |
| 2 | 0.07 | 7 | 2.24 | 0 (100) | 20 (67) | 35 (22) | 10 (33) | 10 (0) | 30 (50) | 35 (0) |
| 2 | 1.12 | 8 | 2.24 | 20 (71) | 100 (0) | 80 (0) | 80 (0) | 90 (5) | 95 (0) | 70 (13) |
| 2 | 0.28 | 8 | 2.24 | 0 (100) | 45 (55) | 40 (43) | 40 (0) | 65 (0) | 35 (50) | 40 (20) |
| 2 | 0.07 | 8 | 2.24 | 0 (100) | 10 (83) | 40 (11) | 10 (33) | 10 (0) | 30 (50) | 30 (14) |
| 2 | 1.12 | 9 | 2.24 | 10 (86) | 100 (0) | 70 (6) | 65 (7) | 98 (0) | 100 (0) | 75 (6) |
| 2 | 0.28 | 9 | 2.24 | 0 (100) | 99 (0) | 65 (7) | 45 (0) | 90 (0) | 99 (0) | 65 (0) |

TABLE 1-continued

% PLANT INHIBITION AND % SAFENING EFFECT ( )

| HERB. NO. | RATE | ANTI-DOTE NO. | RATE | CORN W | WO | SORGHUM (GRAIN) W | WO | SOYBEAN W | WO | WHEAT W | WO | RICE W | WO | YEFT W | WO | VELE W | WO |
|---|---|---|---|---|---|---|---|---|---|---|---|---|---|---|---|---|---|
| 2 | 0.07 | 9 | 2.24 | 0 (100) | 70 (0) | 45 (0) | | 15 (0) | | 15 (0) | | 70 (0) | | 35 (0) | |
| 2 | 1.12 | 10 | 2.24 | 20 (71) | 100 (0) | 80 (0) | | 85 (0) | | 98 (0) | | 95 (0) | | 70 (13) | |
| 2 | 0.28 | 10 | 2.24 | 20 (33) | 85 (14) | 40 (43) | | 25 (0) | | 50 (0) | | 60 (14) | | 45 (10) | |
| 2 | 0.07 | 10 | 2.24 | 10 (0) | 60 (0) | 30 (33) | | 10 (33) | | 15 (0) | | 35 (42) | | 30 (0) | |
| 2 | 1.12 | 11 | 2.24 | 35 (50) | 100 (0) | 0 45 (40) | | 65 (7) | | 90 (5) | | 98 (0) | | 50 (38) | |
| 2 | 0.28 | 11 | 2.24 | 20 (33) | 98 (0) | 35 (50) | | 30 (0) | | 15 (25) | | 80 (0) | | 45 (10) | |
| 2 | 0.07 | 11 | 2.24 | 0 (100) | 80 (0) | 30 (33) | | 15 (0) | | 15 (0) | | 60 (0) | | 30 (14) | |
| 2 | 1.12 | 12 | 2.24 | 35 (50) | 100 (0) | 45 (40) | | 60 (14) | | 100 (0) | | 90 (8) | | 65 (19) | |
| 2 | 0.28 | 12 | 2.24 | 10 (67) | 99 (0) | 40 (43) | | 50 (0) | | 90 (0) | | 70 (0) | | 60 (0) | |
| 2 | 0.07 | 12 | 2.24 | 0 (100) | 40 (33) | 25 (44) | | 20 (0) | | 40 (0) | | 35 (42) | | 40 (0) | |
| 3 | 4.48 | | 2.24 | 35 | 70 | 80 | | 25 | | 75 | | 40 | | 60 | |
| 3 | 1.12 | | 2.24 | 15 | 55 | 70 | | 25 | | 35 | | 25 | | 20 | |
| 3 | 0.28 | | 2.24 | 10 | 35 | 70 | | 20 | | 15 | | 20 | | 10 | |
| 3 | 4.48 | 1 | 2.24 | 60 (0) | 75 (0) | 80 (0) | | 30 (0) | | 60 (20) | | 65 (0) | | 55 (8) | |
| 3 | 1.12 | 1 | 2.24 | 20 (0) | 45 (18) | 70 (0) | | 20 (20) | | 50 (0) | | 60 (0) | | 45 (0) | |
| 3 | 0.28 | 1 | 2.24 | 0 (100) | 25 (29) | 60 (14) | | 20 (0) | | 35 (0) | | 40 (9) | | 35 (0) | |
| 3 | 4.48 | 2 | 2.24 | 35 (0) | 65 (7) | 85 (0) | | 35 (0) | | 65 (13) | | 80 (0) | | 80 (0) | |
| 3 | 1.12 | 2 | 2.24 | 20 (0) | 25 (55) | 70 (0) | | 30 (0) | | 60 (0) | | 45 (0) | | 35 (0) | |
| 3 | 0.28 | 2 | 2.24 | 15 (0) | 10 (72) | 55 (21) | | 15 (25) | | 45 (0) | | 30 (0) | | 30 (0) | |
| 3 | 4.48 | 3 | 2.24 | 45 (0) | 90 (0) | 75 (6) | | 35 (0) | | 90 (0) | | 60 (0) | | 60 (0) | |
| 3 | 1.12 | 3 | 2.24 | 25 (0) | 65 (0) | 55 (21) | | 25 (0) | | 45 (0) | | 40 (0) | | 35 (0) | |
| 3 | 0.28 | 3 | 2.24 | 10 (0) | 30 (14) | 45 (38) | | 20 (0) | | 35 (0) | | 25 (0) | | 20 (0) | |
| 3 | 4.48 | 4 | 2.24 | 99 (0) | 100 (0) | 90 (0) | | 55 (0) | | 85 (0) | | 75 (0) | | 75 (0) | |
| 3 | 1.12 | 4 | 2.24 | 90 (0) | 99 (0) | 70 (0) | | 35 (0) | | 60 (0) | | 60 (0) | | 30 (0) | |
| 3 | 0.28 | 4 | 2.24 | 40 (0) | 80 (0) | 63 (7) | | 25 (0) | | 40 (0) | | 30 (0) | | 20 (0) | |
| 3 | 4.48 | 5 | 2.24 | 35 (0) | 60 (14) | 80 (0) | | 30 (0) | | 55 (27) | | 75 (0) | | 65 (0) | |
| 3 | 1.12 | 5 | 2.24 | 0 (100) | 20 (64) | 70 (0) | | 20 (0) | | 45 (0) | | 30 (0) | | 55 (0) | |
| 3 | 0.28 | 5 | 2.24 | 0 (100) | 10 (71) | 50 (29) | | 10 (50) | | 15 (0) | | 35 (0) | | 25 (0) | |
| 3 | 4.48 | 6 | 2.24 | 60 (0) | 75 (0) | 85 (0) | | 35 (0) | | 55 (27) | | 65 (0) | | 60 (0) | |
| 3 | 1.12 | 6 | 2.24 | 20 (0) | 65 (0) | 60 (14) | | 25 (0) | | 30 (14) | | 60 (0) | | 45 (0) | |
| 3 | 0.28 | 6 | 2.24 | 0 (100) | 43 (0) | 55 (21) | | 15 (25) | | 30 (0) | | 65 (0) | | 40 (0) | |
| 3 | 4.48 | 7 | 2.24 | 20 (43) | 75 (0) | 80 (0) | | 25 (0) | | 90 (0) | | 45 (0) | | 40 (33) | |
| 3 | 1.12 | 7 | 2.24 | 15 (0) | 30 (45) | 65 (7) | | 20 (20) | | 45 (0) | | 55 (0) | | 35 (0) | |
| 3 | 0.28 | 7 | 2.24 | 10 (0) | 10 (71) | 65 (7) | | 15 (25) | | 15 (0) | | 25 (0) | | 20 (0) | |
| 3 | 4.48 | 8 | 2.24 | 25 (29) | 40 (43) | 80 (0) | | 30 (0) | | 85 (0) | | 35 (13) | | 45 (25) | |
| 3 | 1.12 | 8 | 2.24 | 20 (0) | 20 (64) | 65 (7) | | 20 (20) | | 60 (0) | | 20 (20) | | 20 (0) | |
| 3 | 0.28 | 8 | 2.24 | 10 (0) | 10 (71) | 40 (43) | | 15 (25) | | 25 (0) | | 15 (25) | | 10 (0) | |
| 3 | 4.48 | 9 | 2.24 | 15 | 70 | 85 | | 35 | | 75 | | 45 | | 55 | |

TABLE 1-continued

| HERB. NO. | HERB. RATE | ANTIDOTE NO. | ANTIDOTE RATE | CORN | SORGHUM (GRAIN) | SOYBEAN | WHEAT | RICE | YEFT | VELE |
|---|---|---|---|---|---|---|---|---|---|---|
|  |  |  |  | (57) | (0) | (0) | (0) | (0) | (0) | (0) (8) |
| 3 | 1.12 | 9 | 2.24 | 10 (33) | 45 (18) | 65 (7) | 30 (0) | 60 (0) | 40 (0) | 30 (0) |
| 3 | 0.28 | 9 | 2.24 | 0 (100) | 0 (100) | 30 (57) | 20 (0) | 40 (0) | 0 (100) | 10 (0) |
| 3 | 4.48 | 10 | 2.24 | 35 (0) | 70 (0) | 80 (0) | 35 (0) | 80 (0) | 30 (25) | 35 (42) |
| 3 | 1.12 | 10 | 2.24 | 15 (0) | 20 (64) | 50 (29) | 20 (20) | 45 (0) | 30 (0) | 25 (0) |
| 3 | 0.28 | 10 | 2.24 | 10 (0) | 6 (100) | 55 (21) | 10 (50) | 10 (33) | 15 (25) | 25 (0) |
| 3 | 4.48 | 11 | 2.24 | 25 (29) | 80 (0) | 75 (6) | 30 (0) | 85 (0) | 55 (0) | 65 (0) |
| 3 | 1.12 | 11 | 2.24 | 20 (0) | 45 (18) | 50 (29) | 20 (20) | 65 (0) | 25 (0) | 25 (0) |
| 3 | 0.28 | 11 | 2.24 | 10 (0) | 10 (71) | 35 (50) | 10 (50) | 20 (0) | 10 (50) | 20 (0) |
| 3 | 4.48 | 12 | 2.24 | 30 (14) | 75 (0) | 70 (13) | 30 (0) | 85 (0) | 75 (0) | 65 (0) |
| 3 | 1.12 | 12 | 2.24 | 15 (0) | 55 (0) | 55 (21) | 30 (0) | 70 (0) | 30 (0) | 30 (0) |
| 3 | 0.28 | 12 | 2.24 | 15 (0) | 30 (14) | 40 (43) | 20 (0) | 30 (0) | 15 (25) | 15 (0) |
| 4 | 0.018 |  |  | 99 | 100 | 75 | 75 | 65 | 90 | 40 |
| 4 | 0.004 |  |  | 45 | 95 | 40 | 50 | 35 | 65 | 20 |
| 4 | 0.001 |  |  | 0 | 25 | 30 | 15 | 20 | 20 | 0 |
| 4 | 0.018 | 1 | 2.24 | 100 (0) | 100 (0) | 90 (0) | 60 (20) | 70 (0) | 98 (0) | 65 (0) |
| 4 | 0.004 | 1 | 2.24 | 45 (0) | 80 (16) | 60 (0) | 20 (60) | 35 (0) | 35 (46) | 20 (0) |
| 4 | 0.001 | 1 | 2.24 | 0 (0) | 20 (20) | 65 (0) | 15 (0) | 15 (25) | 25 (0) | 10 (0) |
| 4 | 0.018 | 2 | 2.24 | 90 (9) | 100 (0) | 80 (0) | 45 (40) | 40 (38) | 90 (0) | 60 (0) |
| 4 | 0.004 | 2 | 2.24 | 25 (44) | 90 (5) | 60 (0) | 15 (70) | 20 (43) | 45 (31) | 25 (0) |
| 4 | 0.001 | 2 | 2.24 | 0 (0) | 35 (0) | 40 (0) | 15 (0) | 20 (0) | 30 (0) | 15 (0) |
| 4 | 0.018 | 3 | 2.24 | 90 (9) | 95 (5) | 70 (7) | 60 (20) | 65 (0) | 75 (17) | 45 (0) |
| 4 | 0.004 | 3 | 2.24 | 25 (44) | 90 (5) | 45 (0) | 15 (70) | 10 (71) | 35 (46) | 15 (25) |
| 4 | 0.001 | 3 | 2.24 | 0 (0) | 35 (0) | 40 (0) | 10 (33) | 0 (100) | 15 (25) | 10 (0) |
| 4 | 0.018 | 4 | 2.24 | 100 (0) | 100 (0) | 70 (6) | 65 (13) | 60 (8) | 90 (0) | 60 (0) |
| 4 | 0.004 | 4 | 2.24 | 70 (0) | 80 (16) | 40 (0) | 25 (50) | 20 (43) | 75 (0) | 15 (25) |
| 4 | 0.001 | 4 | 2.24 | 30 (0) | 35 (0) | 35 (0) | 20 (0) | 15 (25) | 20 (0) | 15 (0) |
| 4 | 0.018 | 5 | 2.24 | 95 (4) | 100 (0) | 65 (13) | 30 (60) | 65 (0) | 95 (0) | 35 (13) |
| 4 | 0.004 | 5 | 2.24 | 35 (22) | 80 (16) | 40 (0) | 15 (70) | 10 (71) | 40 (38) | 20 (0) |
| 4 | 0.001 | 5 | 2.24 | 15 (0) | 10 (60) | 25 (17) | 15 (0) | 0 (100) | 30 (0) | 15 (0) |
| 4 | 0.018 | 6 | 2.24 | 100 (0) | 100 (0) | 80 (0) | 70 (6) | 65 (0) | 80 (11) | 65 (0) |
| 4 | 0.004 | 6 | 2.24 | 80 (0) | 95 (0) | 70 (0) | 30 (40) | 35 (0) | 80 (0) | 30 (0) |
| 4 | 0.001 | 6 | 2.24 | 0 (0) | 10 (60) | 20 (33) | 15 (0) | 20 (0) | 10 (50) | 15 (0) |
| 4 | 0.018 | 7 | 2.24 | 90 (9) | 95 (5) | 80 (0) | 70 (6) | 70 (0) | 80 (11) | 35 (13) |
| 4 | 0.004 | 7 | 2.24 | 35 (22) | 75 (21) | 65 (0) | 30 (40) | 25 (29) | 15 (77) | 20 (0) |
| 4 | 0.001 | 7 | 2.24 | 25 (0) | 15 (40) | 25 (17) | 15 (0) | 15 (25) | 15 (25) | 15 (0) |
| 4 | 0.018 | 8 | 2.24 | 90 (9) | 95 (5) | 80 (0) | 65 (13) | 70 (0) | 60 (33) | 45 (0) |
| 4 | 0.004 | 8 | 2.24 | 10 (78) | 55 (53) | 45 (0) | 20 (60) | 20 (43) | 40 (38) | 35 (0) |

TABLE 1-continued

| | | | | % PLANT INHIBITION AND % SAFENING EFFECT ( ) | | | | | | | | | | | | | |
|---|---|---|---|---|---|---|---|---|---|---|---|---|---|---|---|---|---|
| HERB. | | ANTI-DOTE | | CORN | | SORGHUM (GRAIN) | | SOYBEAN | | WHEAT | | RICE | | YEFT | | VELE | |
| NO. | RATE | NO. | RATE | W | WO | W | WO | W | WO | W | WO | W | WO | W | WO | W | WO |
| 4 | 0.001 | 8 | 2.24 | 0 (0) | | 10 (60) | | 25 (17) | | 15 (0) | | 15 (25) | | 25 (0) | | 20 (0) | |
| 4 | 0.018 | 9 | 2.24 | 55 (44) | | 100 (0) | | 80 (0) | | 40 (47) | | 70 (0) | | 99 (0) | | 25 (38) | |
| 4 | 0.004 | 9 | 2.24 | 15 (67) | | 75 (21) | | 50 (0) | | 20 (60) | | 15 (57) | | 45 (31) | | 15 (25) | |
| 4 | 0.001 | 9 | 2.24 | 10 (0) | | 10 (60) | | 35 (0) | | 15 (0) | | 15 (25) | | 25 (0) | | 10 (0) | |
| 4 | 0.018 | 10 | 2.24 | 60 (39) | | 100 (0) | | 75 (0) | | 70 (6) | | 65 (0) | | 90 (0) | | 60 (0) | |
| 4 | 0.004 | 10 | 2.24 | 25 (44) | | 70 (26) | | 50 (0) | | 20 (60) | | 20 (43) | | 25 (62) | | 20 (0) | |
| 4 | 0.001 | 10 | 2.24 | 10 (0) | | 20 (20) | | 25 (17) | | 15 (0) | | 20 (0) | | 15 (25) | | 15 (0) | |
| 4 | 0.018 | 11 | 2.24 | 65 (34) | | 100 (0) | | 65 (13) | | 45 (40) | | 45 (31) | | 80 (11) | | 40 (0) | |
| 4 | 0.004 | 11 | 2.24 | 10 (78) | | 80 (16) | | 35 (13) | | 25 (50) | | 35 (0) | | 25 (62) | | 20 (0) | |
| 4 | 0.001 | 11 | 2.24 | 0 (0) | | 40 (0) | | 30 (0) | | 25 (0) | | 30 (0) | | 15 (25) | | 20 (0) | |
| 4 | 0.018 | 12 | 2.24 | 40 (60) | | 100 (0) | | 75 (0) | | 15 (80) | | 45 (31) | | 30 (67) | | 30 (25) | |
| 4 | 0.004 | 12 | 2.24 | 15 (67) | | 90 (5) | | 35 (13) | | 15 (70) | | 30 (14) | | 30 (54) | | 30 (0) | |
| 4 | 0.001 | 12 | 2.24 | 0 (0) | | 0 (100) | | 25 (0) | | 10 (33) | | 20 (0) | | 20 (0) | | 20 (0) | |
| 5 | 1.12 | | | | 55 | | 85 | | 85 | | 90 | | 75 | | 80 | | 70 |
| 5 | 0.28 | | | | 25 | | 20 | | 80 | | 80 | | 60 | | 80 | | 60 |
| 5 | 0.07 | | | | 15 | | 10 | | 80 | | 40 | | 25 | | 25 | | 25 |
| 5 | 1.12 | 1 | 2.24 | 55 (0) | | 80 (60 | | 85 (0) | | 85 (6) | | 80 (0) | | 90 (0) | | 90 (0) | |
| 5 | 0.28 | 1 | 2.24 | 30 (0) | | 45 (0) | | 80 (0) | | 80 (0) | | 70 (0) | | 70 (13) | | 85 (0) | |
| 5 | 0.07 | 1 | 2.24 | 0 (100) | | 0 (100) | | 80 (0) | | 15 (63) | | 10 (60) | | 0 (100) | | 20 (20) | |
| 5 | 1.12 | 2 | 2.24 | 50 (9) | | 95 (0) | | 90 (0) | | 90 (0) | | 80 (0) | | 85 (0) | | 85 (0) | |
| 5 | 0.28 | 2 | 2.24 | 25 (0) | | 70 (0) | | 90 (0) | | 90 (0) | | 65 (0) | | 75 (6) | | 75 (0) | |
| 5 | 0.07 | 2 | 2.24 | 15 (0) | | 25 (0) | | 90 (0) | | 35 (13) | | 15 (40) | | 0 (100) | | 30 (0) | |
| 5 | 1.12 | 3 | 2.24 | 50 (9) | | 95 (0) | | 90 (0) | | 90 (0) | | 75 (0) | | 95 (0) | | 90 (0) | |
| 5 | 0.28 | 3 | 2.24 | 20 (20) | | 65 (0) | | 80 (0) | | 80 (0) | | 65 (0) | | 75 (6) | | 65 (0) | |
| 5 | 0.07 | 3 | 2.24 | 15 (0) | | 10 (0) | | 80 (0) | | 45 (0) | | 15 (40) | | 20 (20) | | 20 (20) | |
| 5 | 1.12 | 4 | 2.24 | 55 (0) | | 95 (0) | | 99 (0) | | 90 (0) | | 75 (0) | | 95 (0) | | 90 (0) | |
| 5 | 0.28 | 4 | 2.24 | 30 (0) | | 45 (0) | | 90 (0) | | 80 (0) | | 45 (25) | | 70 (13) | | 70 (0) | |
| 5 | 0.07 | 4 | 2.24 | 0 (100) | | 35 (0) | | 80 (0) | | 15 (63) | | 0 (100) | | 0 (100) | | 20 (20) | |
| 5 | 1.12 | 5 | 2.24 | 25 (55) | | 50 (41) | | 80 (6) | | 70 (22) | | 55 (27) | | 80 (0) | | 75 (0) | |
| 5 | 0.28 | 5 | 2.24 | 15 (40) | | 40 (0) | | 85 (0) | | 40 (50) | | 15 (75) | | 80 (0) | | 50 (17) | |
| 5 | 0.07 | 5 | 2.24 | 10 (33) | | 20 (0) | | 80 (0) | | 25 (38) | | 0 (100) | | 15 (40) | | 20 (20) | |
| 5 | 1.12 | 6 | 2.24 | 50 (9) | | 90 (0) | | 90 (0) | | 90 (0) | | 75 (0) | | 90 (0) | | 80 (0) | |
| 5 | 0.28 | 6 | 2.24 | 30 (0) | | 75 (0) | | 80 (0) | | 55 (31) | | 60 (0) | | 75 (6) | | 65 (0) | |
| 5 | 0.07 | 6 | 2.24 | 15 (0) | | 30 (0) | | 80 (0) | | 15 (63) | | 10 (60) | | 40 (0) | | 30 (0) | |
| 5 | 1.12 | 7 | 2.24 | 55 (0) | | 85 (0) | | 85 (0) | | 70 (0) | | 75 (0) | | 85 (0) | | 80 (0) | |
| 5 | 0.28 | 7 | 2.24 | 25 (0) | | 75 (0) | | 85 (0) | | 80 (0) | | 65 (0) | | 80 (0) | | 80 (0) | |
| 5 | 0.07 | 7 | 2.24 | 0 (100) | | 15 (0) | | 80 (0) | | 0 (100) | | 10 (60) | | 0 (100) | | 25 (0) | |
| 5 | 1.12 | 8 | 2.24 | 80 | | 90 | | 85 | | 90 | | 65 | | 80 | | 75 | |

TABLE 1-continued

| HERB. NO. | RATE | ANTI-DOTE NO. | RATE | CORN W | WO | SORGHUM (GRAIN) W | WO | SOYBEAN W | WO | WHEAT W | WO | RICE W | WO | YEFT W | WO | VELE W | WO |
|---|---|---|---|---|---|---|---|---|---|---|---|---|---|---|---|---|---|
| | | | | | (0) | | (0) | | (0) | | (0) | | (13) | | (0) | | (0) |
| 5 | 0.28 | 8 | 2.24 | 30 | | 45 | | 85 | | 75 | | 65 | | 65 | | 60 | |
| | | | | | (0) | | (0) | | (0) | | (6) | | (0) | | (19) | | (0) |
| 5 | 0.07 | 8 | 2.24 | 15 | | 15 | | 80 | | 30 | | 10 | | 0 | | 25 | |
| | | | | | (0) | | (0) | | (0) | | (25) | | (60) | | (100) | | (0) |
| 5 | 1.12 | 9 | 2.24 | 55 | | 90 | | 90 | | 95 | | 80 | | 95 | | 85 | |
| | | | | | (0) | | (0) | | (0) | | (0) | | (0) | | (0) | | (0) |
| 5 | 0.28 | 9 | 2.24 | 35 | | 45 | | 80 | | 55 | | 40 | | 70 | | 35 | |
| | | | | | (0) | | (0) | | (0) | | (31) | | (33) | | (13) | | (42) |
| 5 | 0.07 | 9 | 2.24 | 0 | | 0 | | 75 | | 15 | | 0 | | 15 | | 25 | |
| | | | | | (100) | | (100) | | (6) | | (63) | | (100) | | (40) | | (0) |
| 5 | 1.12 | 10 | 2.24 | 55 | | 75 | | 85 | | 85 | | 65 | | 70 | | 80 | |
| | | | | | (0) | | (12) | | (0) | | (6) | | (13) | | (13) | | (0) |
| 5 | 0.28 | 10 | 2.24 | 20 | | 25 | | 85 | | 55 | | 30 | | 70 | | 60 | |
| | | | | | (20) | | (0) | | (0) | | (2) | | (40) | | (13) | | (0) |
| 5 | 0.07 | 10 | 2.24 | 10 | | 15 | | 80 | | 35 | | 15 | | 60 | | 40 | |
| | | | | | (33) | | (0) | | (0) | | (13) | | (40) | | (0) | | (0) |
| 5 | 1.12 | 11 | 2.24 | 55 | | 95 | | 85 | | 90 | | 80 | | 90 | | 80 | |
| | | | | | (0) | | (0) | | (0) | | (0) | | (0) | | (0) | | (0) |
| 5 | 0.28 | 11 | 2.24 | 30 | | 80 | | 80 | | 50 | | 45 | | 40 | | 35 | |
| | | | | | (0) | | (0) | | (0) | | (38) | | (25) | | (50) | | (42) |
| 5 | 0.07 | 11 | 2.24 | 15 | | 20 | | 80 | | 30 | | 60 | | 15 | | 20 | |
| | | | | | (0) | | (0) | | (0) | | (25) | | (60) | | (40) | | (20) |
| 5 | 1.12 | 12 | 2.24 | 45 | | 60 | | 85 | | 55 | | 35 | | 25 | | 35 | |
| | | | | | (10) | | (29) | | (0) | | (39) | | (53) | | (69) | | (50) |
| 5 | 0.28 | 12 | 2.24 | 35 | | 70 | | 90 | | 65 | | 45 | | 25 | | 45 | |
| | | | | | (0) | | (0) | | (0) | | (19) | | (25) | | (69) | | (25) |
| 5 | 0.07 | 12 | 2.24 | 20 | | 50 | | 80 | | 45 | | 40 | | 30 | | 40 | |
| | | | | | (0) | | (0) | | (0) | | (0) | | (0) | | (0) | | (0) |

EXAMPLE 2

Following the same procedure described in Example 1, Antidote Nos. 1, 3–11 and 13–17 were tested for their efficacy against Herbicide No. 6. The same crop and weed species used in Example 1 were used in this test. Results are reported in Table 2.

TABLE 2

| HERB. NO. | RATE | ANTI-DOTE NO. | RATE | CORN W | WO | SORGHUM (GRAIN) W | WO | SOYBEAN W | WO | WHEAT W | WO | RICE W | WO | VELE W | WO | YEFT W | WO |
|---|---|---|---|---|---|---|---|---|---|---|---|---|---|---|---|---|---|
| 6 | 0.07 | 4 | 2.24 | 15 | | 25 | | 0 | | 0 | | 0 | | 0 | | 0 | |
| 6 | 0.28 | 4 | 2.24 | 50 | 20 | 90 | 25 | 70 | 40 | 30 | | 10 | | 40 | 10 | 70 | 10 |
| 6 | 1.12 | 4 | 2.24 | 95 | 65 | 98 | 95 | 90 | 80 | 75 | 15 | 50 | 40 | 40 | 75 | 80 | 75 |
| | | | | | | | | | | | | | | (47) | | | |
| 6 | 0.07 | 9 | 2.24 | 0 | | 0 | | 0 | | 0 | | 0 | | 0 | | 0 | |
| 6 | 0.28 | 9 | 2.24 | 10 | 20 | 45 | 25 | 70 | 40 | 0 | | 20 | | 40 | 10 | 50 | 10 |
| | | | | (50) | | | | | | | | | | | | | |
| 6 | 1.12 | 9 | 2.24 | 20 | 65 | 95 | 95 | 80 | 80 | 20 | 15 | 35 | 40 | 40 | 75 | 50 | 75 |
| | | | | (70) | | (0) | | (0) | | | | (13) | | (47) | | (23) | |
| 6 | 0.07 | 3 | 2.24 | 0 | | 0 | | 0 | | 0 | | 0 | | 0 | | 0 | |
| 6 | 0.28 | 3 | 2.24 | 20 | 20 | 65 | 25 | 70 | 40 | 15 | | 10 | | 40 | | 50 | 10 |
| | | | | (0) | | | | | | | | | | | | | |
| 6 | 1.12 | 3 | 2.24 | 75 | 65 | 95 | 95 | 80 | 80 | 35 | 15 | 35 | 40 | 50 | 75 | 70 | 75 |
| | | | | | | (0) | | (0) | | | | (13) | | (34) | | (7) | |
| 6 | 0.07 | 7 | 2.24 | 0 | | 0 | | 0 | | 0 | | 0 | | 0 | | 0 | |
| 6 | 0.28 | 7 | 2.24 | 0 | 20 | 20 | 25 | 50 | 40 | 0 | | 0 | | 20 | 10 | 20 | 10 |
| | | | | (100) | | (20) | | | | | | | | | | | |
| 6 | 1.12 | 7 | 2.24 | 65 | 65 | 95 | 95 | 80 | 80 | 20 | 15 | 40 | 40 | 60 | 75 | 70 | 75 |
| | | | | (0) | | (0) | | (0) | | | | (0) | | (20) | | (7) | |
| 6 | 0.07 | 11 | 2.24 | 0 | | 0 | | 0 | | 0 | | 0 | | 0 | | 0 | |
| 6 | 0.28 | 11 | 2.24 | 0 | 20 | 25 | 25 | 40 | 40 | 0 | | 0 | | 30 | 10 | 30 | 10 |
| | | | | (10) | | (0) | | (0) | | | | | | | | | |
| 6 | 1.12 | 11 | 2.24 | 25 | 65 | 95 | 95 | 85 | 80 | 20 | 15 | 30 | 40 | 40 | 75 | 60 | 75 |
| | | | | (62) | | (0) | | | | | | (25) | | (47) | | (20) | |

TABLE 2-continued

| HERB. | | ANTI-DOTE | | \% PLANT INHIBITION AND \% SAFENING EFFECT ( ) | | | | | | | | | | | | | |
|---|---|---|---|---|---|---|---|---|---|---|---|---|---|---|---|---|---|
| | | | | CORN | | SORGHUM (GRAIN) | | SOYBEAN | | WHEAT | | RICE | | VELE | | YEFT | |
| NO. | RATE | NO. | RATE | W | WO | W | WO | W | WO | W | WO | W | WO | W | WO | W | WO |
| 6 | 0.07 | 5 | 2.24 | 0 | | 0 | | 0 | | 0 | | 0 | | 0 | | 0 | |
| 6 | 0.28 | 5 | 2.24 | 10 | 20 | 20 | 25 | 40 | 40 | 0 | | 0 | | 30 | 10 | 30 | 10 |
| | | | | (50) | | (20) | | (0) | | | | | | | | | |
| 6 | 1.12 | 5 | 2.24 | 65 | 65 | 80 | 95 | 85 | 80 | 0 | 15 | 20 | 40 | 40 | 75 | 50 | 75 |
| | | | | (0) | | (16) | | | | (100) | | (50) | | (47) | | (34) | |
| 6 | 0.07 | 13 | 2.24 | 0 | | 0 | | 0 | | 0 | | 0 | | 0 | | 0 | |
| 6 | 0.28 | 13 | 2.24 | 0 | 20 | 40 | 25 | 50 | 40 | 0 | | 30 | | 40 | 10 | 40 | 10 |
| | | | | (100) | | | | | | | | | | | | | |
| 6 | 1.12 | 13 | 2.24 | 5 | 65 | 80 | 95 | 80 | 80 | 0 | 15 | 30 | 40 | 50 | 75 | 60 | 75 |
| | | | | (93) | | (16) | | (0) | | (100) | | (25) | | (34) | | (20) | |
| 6 | 0.07 | 14 | 2.24 | 0 | | 0 | | 0 | | 0 | | 0 | | 0 | | 0 | |
| 6 | 0.28 | 14 | 2.24 | 0 | 20 | 20 | 25 | 50 | 40 | 0 | | 10 | | 30 | 10 | 20 | 10 |
| | | | | (100) | | (20) | | | | | | | | | | | |
| 6 | 1.12 | 14 | 2.24 | 20 | 65 | 65 | 95 | 80 | 80 | 20 | 15 | 25 | 40 | 50 | 75 | 55 | 75 |
| | | | | (70) | | (32) | | (0) | | | | (38) | | (34) | | (27) | |
| 6 | 0.07 | 2 | 2.24 | | | | | | | | | | | | | | |
| 6 | 0.28 | 2 | 2.24 | | | | | | | | | | | | | | |
| 6 | 1.12 | 2 | 2.24 | | | | | | | | | | | | | | |
| 6 | 0.07 | 8 | 2.24 | 0 | | 0 | | 0 | | 0 | | 0 | | 0 | | 0 | |
| 6 | 0.28 | 8 | 2.24 | 15 | 20 | 10 | 25 | 70 | 40 | 0 | | 0 | | 10 | 10 | 10 | 10 |
| | | | | (25) | | (60) | | | | | | | | (0) | | (0) | |
| 6 | 1.12 | 8 | 2.24 | 25 | 65 | 40 | 95 | 80 | 80 | 0 | 15 | 5 | 40 | 40 | 75 | 40 | 75 |
| | | | | (62) | | (58) | | (0) | | (100) | | (88) | | (47) | | (47) | |
| 6 | 0.07 | 15 | 2.24 | 0 | | 0 | | 0 | | 0 | | 0 | | 0 | | 0 | |
| 6 | 0.28 | 15 | 2.24 | 0 | 20 | 30 | 25 | 70 | 40 | 0 | | 0 | | 20 | 10 | 30 | 10 |
| | | | | (100) | | | | | | | | | | | | | |
| 6 | 1.12 | 15 | 2.24 | 25 | 65 | 95 | 95 | 80 | 80 | 30 | 15 | 40 | 40 | 65 | 75 | 70 | 75 |
| | | | | (62) | | (0) | | (0) | | | | (0) | | (14) | | (7) | |
| 6 | 0.07 | 16 | 2.24 | 0 | | 0 | | 0 | | 0 | | 0 | | 0 | | 0 | |
| 6 | 0.28 | 16 | 2.24 | 0 | 20 | 25 | 25 | 50 | 40 | 0 | | 0 | | 10 | 10 | 0 | 10 |
| | | | | (100) | | (0) | | | | | | | | (0) | | (100) | |
| 6 | 1.12 | 16 | 2.24 | 25 | 65 | 75 | 95 | 80 | 80 | 0 | 15 | 25 | 40 | 30 | 75 | 50 | 75 |
| | | | | (62) | | (22) | | (0) | | (100) | | (38) | | (60) | | (34) | |
| 6 | 0.07 | 17 | 2.24 | 0 | | 0 | | 0 | | 0 | | 0 | | 0 | | 0 | |
| 6 | 0.28 | 17 | 2.24 | 15 | 20 | 60 | 25 | 60 | 40 | 0 | | 20 | | 40 | 10 | 40 | 10 |
| | | | | (25) | | | | | | | | | | | | | |
| 6 | 1.12 | 17 | 2.24 | 60 | 65 | 80 | 95 | 80 | 80 | 10 | 15 | 25 | 40 | 50 | 75 | 70 | 75 |
| | | | | (8) | | (16) | | (0) | | (34) | | (38) | | (34) | | (7) | |
| 6 | 0.07 | 6 | 2.24 | 0 | | 0 | | 0 | | 0 | | 0 | | 0 | | 0 | |
| 6 | 0.28 | 6 | 2.24 | 15 | 20 | 50 | 25 | 60 | 40 | 0 | | 0 | | 30 | 10 | 20 | 10 |
| | | | | (25) | | | | | | | | | | | | | |
| 6 | 1.12 | 6 | 2.24 | 60 | 65 | 80 | 95 | 80 | 80 | 10 | 15 | 30 | 40 | 60 | 75 | 70 | 75 |
| | | | | (8) | | (16) | | (0) | | (34) | | (25) | | (20) | | (7) | |
| 6 | 0.07 | 1 | 2.24 | 0 | | 0 | | 0 | | 0 | | 0 | | 0 | | 0 | |
| 6 | 0.28 | 1 | 2.24 | 0 | 20 | 20 | 25 | 50 | 40 | 0 | | 0 | | 20 | 10 | 20 | 10 |
| | | | | (100) | | (20) | | | | | | | | | | | |
| 6 | 1.12 | 1 | 2.24 | 50 | 65 | 90 | 95 | 80 | 80 | 10 | 15 | 20 | 40 | 50 | 75 | 70 | 75 |
| | | | | (24) | | (6) | | (0) | | (34) | | (50) | | (34) | | (7) | |
| 6 | 0.07 | 10 | 2.24 | 0 | | 0 | | 0 | | 0 | | 0 | | 0 | | 0 | |
| 6 | 0.28 | 10 | 2.24 | 0 | 20 | 25 | 25 | 65 | 40 | 0 | | 0 | | 20 | 10 | 40 | 10 |
| | | | | (100) | | (0) | | | | | | | | | | | |
| 6 | 1.12 | 10 | 2.24 | 10 | 65 | 80 | 95 | 85 | 80 | 10 | 15 | 30 | 40 | 70 | 75 | 70 | 75 |
| | | | | (85) | | (16) | | | | (34) | | (25) | | (7) | | (7) | |

EXAMPLE 3

Additional tests were conducted according to the procedure in Examples 1 and 2 in order to evaluate the antidotal effect of various antidotes against invention Herbicide No. 1 alone and in combination with co-herbicides A, B and C. Also, combinations of these co-herbicidal compounds and invention Herbicide No. 2 were also tested. In this test the crops were corn and sorghum and eight (8) weeds having the following identification by symbol:

| | |
|---|---|
| MOGL | Morningglory |
| COBU | Cocklebur |
| VELE | Velvetleaf |
| BLNS | Black nightshade |
| YEFT | Yellow foxtail |
| YENS | Yellow nutsedge |
| BYGR | Barnyardgrass |
| SHCA | Shattercane |

Results of this test are shown in Table 3.

TABLE 3

| CO-HERB. NO. | RATE | HERB. NO. | RATE | ANTI-DOTE NO.* | MOGL WO | MOGL W | COBU WO | COBU W | VELE WO | VELE W | BLNS WO | BLNS W | CORN WO | CORN W | SORG WO | SORG W | YEFT WO | YEFT W | YENS WO | YENS W | BYGR WO | BYGR W | SHCA WO | SHCA W |
|---|---|---|---|---|---|---|---|---|---|---|---|---|---|---|---|---|---|---|---|---|---|---|---|---|
| — | | 1 | 2.24 | — | 80 | | 80 | | 85 | | 95 | | 55 | | 100 | | 98 | | 100 | | 50 | | 55 | |
| — | | 1 | 1.12 | — | 70 | | 80 | | 85 | | 95 | | 60 | | 100 | | 90 | | 100 | | 45 | | 55 | |
| — | | 1 | 0.56 | — | 60 | | 80 | | 80 | | 95 | | 20 | | 70 | | 95 | | 98 | | 30 | | 40 | |
| — | | 1 | 0.28 | — | 60 | | 75 | | 75 | | 85 | | 10 | | 50 | | 90 | | 99 | | 20 | | 20 | |
| — | | 1 | 0.14 | — | 40 | | 65 | | 70 | | 80 | | 15 | | 25 | | 75 | | 80 | | 10 | | 10 | |
| — | | 1 | 0.07 | — | 20 | | 60 | | 65 | | 70 | | 0 | | 15 | | 45 | | 50 | | 0 | | 0 | |
| — | | 1 | 0.04 | — | 15 | | 60 | | 45 | | 70 | | 0 | | 0 | | 25 | | 35 | | 0 | | 0 | |
| — | | 1 | 2.24 | 10 | (0) | 80 | (0) | 80 | (0) | 95 | (0) | 95 | (45) | 30 | (10) | 90 | (3) | 95 | (0) | 100 | (0) | 75 | (0) | 70 |
| — | | 1 | 1.12 | 10 | (0) | 70 | (0) | 80 | (0) | 85 | (0) | 95 | (67) | 20 | (20) | 80 | (0) | 90 | (0) | 100 | (0) | 55 | (0) | 60 |
| — | | 1 | 0.56 | 10 | (0) | 70 | (0) | 80 | (0) | 80 | (0) | 85 | (0) | 25 | (0) | 75 | (16) | 80 | (0) | 100 | (0) | 50 | (0) | 60 |
| — | | 1 | 0.28 | 10 | (0) | 60 | (7) | 70 | (0) | 80 | (11) | 80 | (0) | 15 | (0) | 40 | (28) | 65 | (0) | 99 | (0) | 30 | (0) | 35 |
| — | | 1 | 0.14 | 10 | (0) | 50 | (7) | 75 | (0) | 75 | (6) | 85 | (0) | 10 | (20) | 15 | (20) | 60 | (0) | 98 | (0) | 20 | (0) | 25 |
| — | | 1 | 0.07 | 10 | (0) | 35 | (8) | 55 | (0) | 65 | (0) | 70 | (0) | 10 | (40) | 16 | (0) | 60 | (0) | 70 | (0) | 0 | (0) | 0 |
| — | | 1 | 0.04 | 10 | (0) | 30 | (17) | 50 | (0) | 60 | (7) | 65 | (0) | 0 | (33) | 0 | (0) | 40 | (0) | 55 | (0) | 0 | (0) | 0 |
| — | | 1 | 2.24 | 12 | (0) | 90 | (0) | 95 | (0) | 95 | (7) | 99 | (0) | 45 | (0) | 80 | (0) | 80 | (0) | 99 | (20) | 40 | (27) | 40 |
| — | | 1 | 1.12 | 12 | (0) | 80 | (0) | 90 | (0) | 95 | (18) | 98 | (20) | 30 | (20) | 75 | (18) | 80 | (1) | 100 | (22) | 35 | (36) | 35 |
| — | | 1 | 0.56 | 12 | (0) | 75 | (0) | 90 | (0) | 95 | (0) | 95 | (50) | 15 | (25) | 65 | (11) | 80 | (0) | 100 | (0) | 30 | (13) | 35 |
| — | | 1 | 0.28 | 12 | (0) | 70 | (0) | 90 | (0) | 90 | (0) | 98 | (25) | 10 | (7) | 60 | (10) | 85 | (13) | 85 | (0) | 20 | (0) | 30 |
| — | | 1 | 0.14 | 12 | (0) | 70 | (0) | 90 | (0) | 90 | (0) | 95 | (0) | 10 | (0) | 35 | (6) | 85 | (24) | 75 | (0) | 20 | (0) | 20 |
| — | | 1 | 0.07 | 12 | (0) | 40 | (0) | 65 | (8) | 60 | (0) | 90 | (33) | 0 | (33) | 10 | (0) | 45 | (6) | 30 | (0) | 0 | (0) | 0 |
| — | | 1 | 0.04 | 12 | (0) | 35 | (0) | 60 | (0) | 60 | (0) | 90 | (0) | 0 | (0) | 0 | (0) | 40 | (40) | 30 | (20) | 40 | (0) | 40 |
| — | | 1 | 2.24 | 9 | (0) | 90 | (0) | 85 | (0) | 95 | (0) | 95 | (73) | 15 | (20) | 80 | (8) | 90 | (14) | 100 | (22) | 35 | (36) | 35 |
| — | | 1 | 1.12 | 9 | (0) | 80 | (0) | 85 | (0) | 90 | (0) | 90 | (67) | 20 | (15) | 85 | (0) | 90 | (0) | 100 | (0) | 75 | (0) | 70 |
| — | | 1 | 0.56 | 9 | (0) | 75 | (0) | 85 | (0) | 90 | (5) | 90 | (25) | 15 | (29) | 50 | (8) | 85 | (3) | 100 | (0) | 70 | (0) | 70 |
| — | | 1 | 0.28 | 9 | (0) | 60 | (0) | 75 | (0) | 80 | (5) | 90 | (0) | 10 | (60) | 20 | (11) | 80 | (11) | 95 | (0) | 60 | (0) | 55 |
| — | | 1 | 0.14 | 9 | (0) | 55 | (0) | 65 | (0) | 75 | (0) | 85 | (33) | 10 | (60) | 10 | (11) | 70 | (3) | 100 | (0) | 40 | (0) | 40 |
| — | | 1 | | 9 | (0) | | (0) | | (0) | | (0) | | (33) | | (60) | | (7) | | (0) | 95 | (0) | 35 | (0) | 35 |

TABLE 3-continued

| | | | | 40 | 45 | 60 | 75 | 15 | 10 | 50 | 65 | 15 | 15 |
|---|---|---|---|---|---|---|---|---|---|---|---|---|---|
| — | 1 | | | 30 (0) | 55 (25) | 55 (8) | 70 (0) | 0 (0) | 0 (33) | 40 (0) | 30 (0) | 0 (0) | 0 (0) |
| — | 1 | 0.07 | 9 | 90 (0) | 90 (8) | 98 (0) | 100 (0) | 20 (0) | 80 (0) | 100 (0) | 100 (14) | 100 (0) | 80 (0) |
| A | | 0.04 | 9 | | | | | | | | | | |
| A | 1 | 2.24 | 10 | 85 (0) | 90 (0) | 98 (0) | 100 (0) | 20 (64) | 85 (20) | 100 (0) | 100 (0) | 98 (0) | 75 (0) |
| A | 0.14 | 1.12 | 10 | 85 (0) | 90 (0) | 95 (0) | 95 (0) | 25 (67) | 55 (15) | 100 (0) | 100 (0) | 98 (0) | 55 (0) |
| A | 0.14 | 0.56 | 10 | 80 (0) | 95 (0) | 90 (0) | 100 (0) | 20 (0) | 45 (21) | 100 (0) | 99 (0) | 98 (0) | 50 (0) |
| A | 0.14 | 0.28 | 10 | 70 (0) | 85 (0) | 90 (0) | 100 (0) | 15 (0) | 30 (10) | 100 (0) | 100 (0) | 98 (0) | 40 (0) |
| A | 0.14 | 0.14 | 10 | 60 (0) | 80 (0) | 80 (0) | 100 (0) | 10 (0) | 15 (0) | 100 (0) | 95 (0) | 98 (0) | 20 (0) |
| A | 0.14 | 0.07 | 10 | 50 (0) | 70 (0) | 70 (0) | 99 (0) | 10 (0) | 10 (0) | 100 (0) | 100 (0) | 99 (0) | 20 (0) |
| A | 0.14 | 0.04 | 10 | 85 (0) | 90 (0) | 98 (0) | 100 (0) | 25 (55) | 100 (0) | 100 (0) | 100 (0) | 100 (0) | 90 (0) |
| A | 0.14 | 2.24 | 12 | 80 (0) | 90 (0) | 98 (0) | 99 (0) | 35 (42) | 99 (1) | 80 (11) | 98 (1) | 98 (0) | 80 (0) |
| A | 0.14 | 1.12 | 12 | 80 (0) | 95 (0) | 95 (0) | 100 (0) | 20 (0) | 80 (0) | 100 (0) | 100 (0) | 100 (0) | 65 (0) |
| A | 0.14 | 0.56 | 12 | 80 (0) | 90 (0) | 98 (0) | 99 (0) | 15 (0) | 80 (0) | 100 (0) | 100 (0) | 98 (0) | 60 (0) |
| A | 0.14 | 0.28 | 12 | 80 (0) | 80 (0) | 90 (0) | 98 (0) | 15 (0) | 60 (0) | 100 (0) | 95 (0) | 99 (0) | 40 (0) |
| A | 0.14 | 0.14 | 12 | 80 (0) | 75 (0) | 85 (0) | 100 (0) | 0 (0) | 35 (0) | 100 (0) | 100 (0) | 98 (0) | 35 (0) |
| A | 0.14 | 0.07 | 12 | 70 (0) | 75 (0) | 80 (0) | 100 (0) | 0 (0) | 15 (0) | 77 (0) | 100 (0) | 99 (0) | 25 (0) |
| A | 0.14 | 0.04 | 12 | 50 (0) | 85 (0) | 95 (0) | 100 (0) | 20 (0) | 100 (0) | 100 (0) | 100 (0) | 99 (0) | 90 (0) |
| A | 0.14 | 2.24 | 9 | 80 (0) | 85 (0) | 100 (0) | 100 (0) | 25 (64) | 99 (1) | 100 (0) | 100 (0) | 100 (0) | 80 (0) |
| A | 0.14 | 1.12 | 9 | 80 (0) | 85 (0) | 95 (0) | 100 (0) | 15 (58) | 55 (1) | 100 (0) | 100 (0) | 100 (0) | 70 (0) |
| A | 0.14 | 0.56 | 9 | 80 (0) | 90 (0) | 95 (0) | 98 (0) | 15 (25) | 40 (21) | 100 (0) | 100 (0) | 98 (0) | 70 (0) |
| A | 0.14 | 0.28 | 9 | 70 (0) | 90 (0) | 90 (0) | 100 (0) | 15 (0) | 20 (10) | 100 (0) | 100 (0) | 98 (0) | 70 (0) |
| A | 0.14 | 0.14 | 9 | 60 (0) | 75 (0) | 85 (0) | 98 (0) | 15 (0) | 15 (20) | 99 (0) | 99 (0) | 95 (0) | 65 (0) |
| A | 0.14 | 0.07 | 9 | 50 (0) | 80 (0) | 70 (0) | 99 (0) | 0 (0) | 20 (0) | 100 (0) | 100 (0) | 100 (0) | 65 (0) |
| A | 0.14 | 0.04 | 9 | | | | | | | | | | |

* Antidote application rate is 0.56.

TABLE 3-continued

| CO-HERB. NO. | RATE | HERB. NO. | RATE | ANTI-DOTE NO.** | MOGL WO | MOGL W | COBU WO | COBU W | VELE WO | VELE W | BLNS WO | BLNS W | CORN WO | CORN W | SORG WO | SORG W | YEFT WO | YEFT W | YENS WO | YENS W | BYGR WO | BYGR W | SHCA WO | SHCA W |
|---|---|---|---|---|---|---|---|---|---|---|---|---|---|---|---|---|---|---|---|---|---|---|---|---|
| A | 0.56 | 2 | 1.12 |   | 85 |   | 90 |   | 95 |   | 99 |   | 85 |   | 100 |   | 100 |   | 100 |   | 100 |   | 99 |   |
| A | 0.28 | 2 | 1.12 |   | 75 |   | 80 |   | 90 |   | 99 |   | 25 |   | 100 |   | 100 |   | 100 |   | 100 |   | 95 |   |
| B | 1.12 | 2 | 1.12 |   | 75 |   | 80 |   | 80 |   | 99 |   | 80 |   | 100 |   | 100 |   | 100 |   | 95 |   | 90 |   |
| B | 0.28 | 2 | 1.12 |   | 70 |   | 95 |   | 75 |   | 80 |   | 20 |   | 100 |   | 99 |   | 100 |   | 98 |   | 85 |   |
| C | 1.12 | 2 | 1.12 |   | 85 |   | 85 |   | 98 |   | 90 |   | 80 |   | 100 |   | 100 |   | 99 |   | 90 |   | 90 |   |
| C | 0.28 | 2 | 1.12 |   | 70 |   | 70 |   | 80 |   | 95 |   | 15 |   | 100 |   | 98 |   | 99 |   | 80 |   | 85 |   |
| A | 0.56 | 2 | 1.12 | 9 | (0) | 90 | (4) | 85 | (0) | 95 | (0) | 100 | ( ) | 50 | (0) | 100 | (0) | 100 | (0) | 100 | (0) | 100 | (9) | 90 |
| A | 1.12 | 2 | 0.28 | 9 | (0) | 80 | (0) | 90 | (11) | 80 | (0) | 99 | (20) | 40 | (2) | 98 | (0) | 100 | (0) | 100 | (0) | 100 | (11) | 85 |
| B | 1.12 | 2 | 0.28 | 9 | (0) | 80 | (0) | 80 | (0) | 85 | (0) | 99 | (50) | 20 | (0) | 100 | (0) | 100 | (0) | 100 | (9) | 99 | (11) | 80 |
| B | 1.12 | 2 | 1.12 | 9 | (0) | 70 | (0) | 75 | (0) | 80 | (0) | 95 | (0) | 50 | (4) | 95 | (1) | 99 | (1) | 99 | (3) | 95 | (18) | 70 |
| C | 1.12 | 2 | 0.28 | 9 | (0) | 80 | (0) | 80 | (8) | 75 | (0) | 98 | (38) | 30 | (0) | 100 | (1) | 90 | (4) | 95 | (0) | 90 | (21) | 80 |
| C | 1.12 | 2 | 1.12 | 9 | (6) | 75 | (0) | 85 | (6) | 85 | (0) | 95 | (0) | 40 | (0) | 99 | (8) | 100 | (9) | 100 | (0) | 80 | (21) | 75 |
| A | 0.56 | 2 | 1.12 | 10 | (0) | 75 | (11) | 90 | (11) | 85 | (1) | 98 | (53) | 25 | (1) | 100 | (0) | 100 | (0) | 100 | (0) | 100 | (9) | 90 |
| A | 1.12 | 2 | 0.28 | 10 | (12) | 80 | (0) | 90 | (11) | 80 | (0) | 100 | (0) | 60 | (5) | 95 | (0) | 99 | (0) | 100 | (0) | 100 | (16) | 85 |
| B | 1.12 | 2 | 0.28 | 10 | (0) | 85 | (0) | 90 | (11) | 95 | (0) | 99 | (25) | 30 | (0) | 100 | (0) | 99 | (0) | 100 | (0) | 95 | (5) | 75 |
| B | 1.12 | 2 | 1.12 | 10 | (0) | 80 | (0) | 85 | (0) | 80 | (0) | 99 | (0) | 50 | (5) | 100 | (1) | 95 | (0) | 99 | (13) | 85 | (12) | 80 |
| C | 1.12 | 2 | 0.28 | 10 | (0) | 85 | (0) | 90 | (3) | 95 | (0) | 95 | (38) | 50 | (5) | 95 | (4) | 99 | (1) | 100 | (11) | 80 | (11) | 80 |
| C | 1.12 | 2 | 1.12 | 12 | (0) | 80 | (0) | 80 | (5) | 85 | (0) | 95 | (0) | 15 | (0) | 100 | (1) | 80 | (0) | 99 | (19) | 65 | (24) | 65 |
| A | 0.56 | 2 | 1.12 | 12 | (0) | 90 | (5) | 85 | (6) | 80 | (9) | 100 | (0) | 40 | (5) | 95 | (0) | 100 | (0) | 100 | (1) | 99 | (14) | 85 |
| A | 1.12 | 2 | 0.28 | 12 | (0) | 80 | (0) | 90 | (6) | 80 | (0) | 100 | (53) | 25 | (0) | 100 | (0) | 100 | (0) | 100 | (0) | 100 | (10) | 80 |
| B | 1.12 | 2 | 0.28 | 12 | (0) | 75 | (0) | 85 | (0) | 75 | (0) | 90 | (0) | 40 | (0) | 100 | (0) | 99 | (0) | 99 | (0) | 99 | (11) | 75 |
| B | 1.12 | 2 | 1.12 | 12 | (0) | 75 | (5) | 90 | (6) | 75 | (9) | 98 | (50) | 35 | (0) | 98 | (1) | 98 | (1) | 99 | (0) | 90 | (11) | 85 |
| C | 1.12 | 2 | 0.28 | 12 | (0) | 85 | (6) | 80 | (3) | 95 | (0) | 95 | (0) | 45 | (2) | 100 | (2) | 85 | (1) | 99 | (0) | 90 | (12) | 85 |
| C | 1.12 | 2 | 1.12 | 12 | (0) | 70 | (6) | 80 | (3) | 80 | (0) | 100 | (44) | 20 | (1) | 99 | (13) | 85 | (19) | 80 | (6) | 75 | (5) | 80 |
| C |   |   |   |   | (0) |   | (0) |   | (0) |   | (0) |   | (0) |   |   |   |   |   |   |   |   |   | (6) |   |

** Antidote application rate is 2.24.

EXAMPLE 4

Following the same procedure described in Example 1, eighteen (18) different antidotes were tested for their efficacy against Herbicide No. 9 in corn, grain sorghum, soybean and rice crops in the presence of velvetleaf and yellow foxtail weeds. Observations were taken eleven days after treatment. The test results are shown in Table 4, wherein the following symbols are used:

GRSO (grain sorghum);
SOBE (soybean);
WH (wheat);
VELE (velvetleaf) and
YEFT (yellow foxtail).

Plant injury is recorded as percent inhibition of growth.

TABLE 4

| Anti- dote No. | Rate Kg/Ha | Herb. No. 9 Kg/Ha | % Plant Inhibition | | | | | | |
|---|---|---|---|---|---|---|---|---|---|
| | | | Corn | GRSO | SOBE | WH | Rice | VELE | YEFT |
| — | — | 0.14 | 55 | 100 | 35 | 85 | 95 | 80 | 90 |
| — | — | 0.04 | 10 | 90 | 25 | 30 | 85 | 40 | 60 |
| — | — | 0.009 | 0 | 90 | 0 | 10 | 60 | 20 | 30 |
| 4 | 2.24 | 0.009 | 40 | 85 | 10 | 20 | 70 | 10 | 40 |
| 4 | 2.24 | 0.04 | 50 | 90 | 10 | 65 | 85 | 40 | 60 |
| 4 | 2.24 | 0.14 | 95 | 99 | 25 | 98 | 99 | 80 | 98 |
| 9 | 2.24 | 0.009 | 0 | 35 | 0 | 0 | 50 | 0 | 30 |
| 9 | 2.24 | 0.04 | 10 | 90 | 30 | 20 | 90 | 30 | 70 |
| 9 | 2.24 | 0.14 | 15 | 98 | 20 | 60 | 90 | 70 | 85 |
| 3 | 2.24 | 0.009 | 0 | 30 | 30 | 0 | 60 | 0 | 0 |
| 3 | 2.24 | 0.04 | 0 | 85 | 0 | 10 | 80 | 50 | 60 |
| 3 | 2.24 | 0.14 | 35 | 95 | 20 | 70 | 90 | 80 | 90 |
| 7 | 2.24 | 0.009 | 0 | 60 | 0 | 0 | 60 | 0 | 0 |
| 7 | 2.24 | 0.04 | 0 | 80 | 0 | 10 | 85 | 70 | 40 |
| 7 | 2.24 | 0.14 | 20 | 98 | 30 | 60 | 98 | 80 | 80 |
| 11 | 2.24 | 0.009 | 0 | 80 | 0 | 0 | 40 | 0 | 0 |
| 11 | 2.24 | 0.04 | 0 | 95 | 0 | 0 | 70 | 30 | 40 |
| 11 | 2.24 | 0.14 | 5 | 98 | 0 | 40 | 95 | 90 | 95 |
| 5 | 2.24 | 0.009 | 0 | 0 | 0 | 0 | 25 | 0 | 0 |
| 5 | 2.24 | 0.04 | 0 | 80 | 0 | 0 | 65 | 50 | 70 |
| 5 | 2.24 | 0.14 | 35 | 95 | 20 | 15 | 90 | 80 | 95 |
| 13 | 2.24 | 0.009 | 0 | 30 | 0 | 0 | 60 | 30 | 40 |
| 13 | 2.24 | 0.04 | 10 | 90 | 25 | 10 | 90 | 60 | 80 |
| 13 | 2.24 | 0.14 | 15 | 98 | 30 | 35 | 100 | 85 | 90 |
| 14 | 2.24 | 0.009 | 0 | 40 | 0 | 0 | 80 | 0 | 0 |
| 14 | 2.24 | 0.04 | 10 | 85 | 30 | 20 | 90 | 30 | 40 |
| 14 | 2.24 | 0.14 | 20 | 98 | 35 | 70 | 98 | 85 | 90 |
| 2 | 2.24 | 0.009 | 0 | 20 | 0 | 0 | 20 | 0 | 0 |
| 2 | 2.24 | 0.04 | 0 | 90 | 10 | 0 | 40 | 50 | 50 |
| 2 | 2.24 | 0.14 | 10 | 98 | 0 | 20 | 98 | 85 | 90 |
| 8 | 2.24 | 0.009 | 0 | 0 | 0 | 0 | 40 | 30 | 20 |
| 8 | 2.24 | 0.04 | 0 | 45 | 20 | 0 | 70 | 20 | 40 |
| 8 | 2.24 | 0.14 | 10 | 98 | 15 | 50 | 95 | 85 | 90 |
| 12 | 2.24 | 0.009 | 0 | 60 | 0 | 0 | 40 | 20 | 0 |
| 12 | 2.24 | 0.04 | 0 | 98 | 0 | 0 | 80 | 50 | 60 |
| 12 | 2.24 | 0.14 | 0 | 98 | 20 | 20 | 95 | 80 | 80 |
| 15 | 2.24 | 0.009 | 0 | 80 | 0 | 0 | 60 | 0 | 0 |
| 15 | 2.24 | 0.04 | 0 | 90 | 10 | 25 | 80 | 40 | 70 |
| 15 | 2.24 | 0.14 | 10 | 98 | 20 | 50 | 95 | 70 | 90 |
| 16 | 2.24 | 0.009 | 0 | 55 | 0 | 0 | 30 | 0 | 0 |
| 16 | 2.24 | 0.04 | 0 | 90 | 0 | 0 | 80 | 0 | 20 |
| 16 | 2.24 | 0.14 | 20 | 100 | 40 | 60 | 100 | 90 | 98 |
| 17 | 2.24 | 0.009 | 0 | 60 | 0 | 0 | 30 | 0 | 0 |
| 17 | 2.24 | 0.04 | 10 | 90 | 20 | 0 | 90 | 70 | 85 |
| 17 | 2.24 | 0.14 | 55 | 100 | 20 | 40 | 95 | 85 | 90 |
| 6 | 2.24 | 0.009 | 0 | 70 | 0 | 0 | 20 | 0 | 0 |
| 6 | 2.24 | 0.04 | 10 | 90 | 10 | 0 | 55 | 20 | 40 |
| 6 | 2.24 | 0.14 | 60 | 90 | 20 | 80 | 95 | 80 | 90 |
| 1 | 2.24 | 0.009 | 0 | 20 | 0 | 0 | 40 | 0 | 20 |
| 1 | 2.24 | 0.04 | 10 | 90 | 0 | 0 | 60 | 60 | 70 |
| 1 | 2.24 | 0.14 | 70 | 95 | 10 | 70 | 98 | 90 | 98 |
| 10 | 2.24 | 0.009 | 0 | 35 | 0 | 0 | 40 | 0 | 20 |
| 10 | 2.24 | 0.04 | 0 | 85 | 0 | 0 | 90 | 60 | 70 |
| 10 | 2.24 | 0.14 | 0 | 90 | 20 | 60 | 95 | 85 | 90 |
| 18 | 2.24 | 0.009 | 0 | 35 | 0 | 0 | 60 | 0 | 0 |
| 18 | 2.24 | 0.04 | 0 | 90 | 10 | 0 | 90 | 60 | 70 |
| 18 | 2.24 | 0.14 | 15 | 95 | 0 | 0 | 98 | 90 | 95 |

All antidotes at 2.24 kg/ha, except Antidote No. 4, provided safening to Herbicide No. 9 at 0.14 kg/ha to one or more of the tested crops. Antidote Nos. 10 and 12 were the most active corn safeners, reducing injury from 55% to 0%. Antidote No. 5 (flurazole) exhibited the best sorghum safening, reducing injury from 90% to 0%. Antidote No. 18 was the most efficacious safener for corn and soybeans; this compound reduced soybean injury from 35% to 0%. Antidote No. 4 anomalously enhanced corn injury from Herbicide No. 9. However, that safener did reduce injury to soybeans from 25% (commercially unsatisfactory) to 10% at 0.04 kg/ha.

EXAMPLE 5

The test procedure, crops and weeds and antidotes used in this example were the same as those used in the test of Example 4, but the herbicide in this example was Herbicide No. 8. Observation of test results was made thirteen days after treatment. Test data are reported in Table 5.

In this test Antidote No. 10 was the most active to safen Herbicide No. 8 to corn, although all antidotes did provide some corn safening. At 2.24 kg/ha Antidote No. 10 reduced corn injury from 60% at 0.04 kg/ha to 25%. Antidote No. 5 was the most efficacious for safening Herbicide No. 8 to sorghum. Most safeners except No. 15 and No. 12 provided sorghum safening to some extent. At 2.24 kg/ha, Antidote No. 5 reduced sorghum injury by the herbicide at 0.009 kg/ha from 60% to 0%. Antidote No. 18 at 2.24 kg/ha reduced wheat injury and soybean injury from Herbicide No. 8 at 0.04 kg/ha from 50% to 10% and 55% to 20%, respectively.

TABLE 5

| Anti-dote No. | Rate Kg/Ha | Herb. No. 8 Kg/Ha | % Plant Inhibition | | | | | | |
|---|---|---|---|---|---|---|---|---|---|
| | | | Corn | GRSO | SOBE | WH | Rice | VELE | YEFT |
| — | — | 0.14 | 78 | 95 | 75 | 85 | 85 | 90 | 70 |
| — | — | 0.04 | 60 | 90 | 55 | 50 | 75 | 50 | 30 |
| — | — | 0.009 | 20 | 60 | 30 | 10 | 40 | 20 | 0 |
| 4 | 2.24 | 0.14 | 85 | 98 | 90 | 90 | 90 | 70 | 60 |
| 4 | 2.24 | 0.04 | 40 | 80 | 60 | 70 | 80 | 50 | 50 |
| 4 | 2.24 | 0.009 | 20 | 20 | 10 | 0 | 30 | 0 | 0 |
| 9 | 2.24 | 0.14 | 75 | 98 | 95 | 90 | 90 | 90 | 80 |
| 9 | 2.24 | 0.04 | 35 | 75 | 60 | 70 | 80 | 60 | 50 |
| 9 | 2.24 | 0.009 | 15 | 20 | 0 | 0 | 30 | 0 | 0 |
| 3 | 2.24 | 0.14 | 90 | 95 | 95 | 90 | 90 | 90 | 85 |
| 3 | 2.24 | 0.04 | 35 | 75 | 40 | 55 | 75 | 70 | 40 |
| 3 | 2.24 | 0.009 | 15 | 20 | 0 | 0 | 25 | 25 | 0 |
| 7 | 2.24 | 0.14 | 75 | 95 | 75 | 80 | 90 | 90 | 85 |
| 7 | 2.24 | 0.04 | 40 | 65 | 50 | 40 | 70 | 40 | 20 |
| 7 | 2.24 | 0.009 | 0 | 20 | 0 | 0 | 40 | 0 | 0 |
| 11 | 2.24 | 0.14 | 70 | 95 | 90 | 80 | 90 | 80 | 65 |
| 11 | 2.24 | 0.04 | 40 | 90 | 70 | 65 | 75 | 50 | 30 |
| 11 | 2.24 | 0.009 | 0 | 15 | 0 | 0 | 30 | 0 | 0 |
| 5 | 2.24 | 0.14 | 85 | 98 | 95 | 90 | 95 | 85 | 85 |
| 5 | 2.24 | 0.04 | 40 | 35 | 40 | 35 | 65 | 50 | 10 |
| 5 | 2.24 | 0.009 | 0 | 0 | 0 | 0 | 40 | 0 | 0 |
| 13 | 2.24 | 0.14 | 80 | 95 | 95 | 90 | 90 | 90 | 80 |
| 13 | 2.24 | 0.04 | 35 | 70 | 55 | 50 | 80 | 50 | 30 |
| 13 | 2.24 | 0.009 | 0 | 20 | 25 | 0 | 40 | 0 | 0 |
| 14 | 2.24 | 0.14 | 75 | 95 | 90 | 90 | 90 | 90 | 85 |
| 14 | 2.24 | 0.04 | 45 | 80 | 40 | 65 | 80 | 30 | 20 |
| 14 | 2.24 | 0.009 | 0 | 20 | 15 | 0 | 40 | 0 | 0 |
| 2 | 2.24 | 0.14 | 75 | 95 | 90 | 90 | 95 | 95 | 80 |
| 2 | 2.24 | 0.04 | 45 | 70 | 60 | 50 | 80 | 50 | 40 |
| 2 | 2.24 | 0.009 | 10 | 40 | 0 | 0 | 20 | 0 | 0 |
| 8 | 2.24 | 0.14 | 95 | 95 | 100 | 95 | 98 | 95 | 85 |
| 8 | 2.24 | 0.04 | 45 | 80 | 70 | 60 | 80 | 30 | 30 |
| 8 | 2.24 | 0.009 | 0 | 25 | 0 | 40 | 40 | 0 | 0 |
| 12 | 2.24 | 0.14 | 75 | 98 | 90 | 95 | 95 | 95 | 90 |
| 12 | 2.24 | 0.04 | 45 | 90 | 70 | 40 | 80 | 70 | 60 |
| 12 | 2.24 | 0.009 | 10 | 60 | 35 | 0 | 30 | 20 | 0 |
| 15 | 2.24 | 0.14 | 90 | 98 | 90 | 95 | 95 | 95 | 90 |
| 15 | 2.24 | 0.04 | 45 | 95 | 70 | 40 | 85 | 70 | 40 |
| 15 | 2.24 | 0.009 | 0 | 60 | 20 | 10 | 30 | 30 | 0 |
| 16 | 2.24 | 0.14 | 90 | 98 | 95 | 95 | 95 | 98 | 98 |
| 16 | 2.24 | 0.04 | 55 | 95 | 75 | 45 | 80 | 80 | 65 |
| 16 | 2.24 | 0.009 | 0 | 20 | 30 | 0 | 10 | 20 | 0 |
| 17 | 2.24 | 0.14 | 80 | 95 | 95 | 90 | 95 | 85 | 80 |
| 17 | 2.24 | 0.04 | 55 | 95 | 65 | 70 | 95 | 70 | 50 |
| 17 | 2.24 | 0.009 | 10 | 30 | 30 | 10 | 20 | 0 | 0 |
| 6 | 2.24 | 0.14 | 80 | 95 | 90 | 85 | 90 | 90 | 80 |
| 6 | 2.24 | 0.04 | 50 | 90 | 70 | 75 | 80 | 60 | 40 |
| 6 | 2.24 | 0.009 | 10 | 30 | 10 | 0 | 40 | 20 | 0 |
| 1 | 2.24 | 0.14 | 80 | 95 | 95 | 90 | 95 | 75 | 80 |
| 1 | 2.24 | 0.04 | 40 | 95 | 70 | 70 | 80 | 30 | 40 |
| 1 | 2.24 | 0.009 | 20 | 40 | 0 | 0 | 70 | 20 | 0 |
| 10 | 2.24 | 0.14 | 80 | 95 | 90 | 90 | 90 | 80 | 85 |
| 10 | 2.24 | 0.04 | 25 | 90 | 50 | 55 | 80 | 70 | 40 |
| 10 | 2.24 | 0.009 | 10 | 25 | 10 | 0 | 40 | 30 | 0 |
| 18 | 2.24 | 0.14 | 85 | 98 | 95 | 75 | 95 | 80 | 85 |
| 18 | 2.24 | 0.04 | 45 | 80 | 20 | 10 | 90 | 60 | 40 |
| 18 | 2.24 | 0.0009 | 15 | 60 | 20 | 0 | 40 | 30 | 0 |

EXAMPLE 6

In this example, a test was conducted to determine the antidotal efficacy of Antidote Nos. 10 and 18 against Herbicide No. 2 in corn, soybean, sorghum, wheat and rice crops in the presence of yellow foxtail and velvetleaf weeds. Test results are shown in Table 6.

EXAMPLE 7

Another test was conducted according to the procedure described and used in the foregoing examples in which six (6) different antidotes were tested against four (4) different herbicides according to Formula I. Test results were observed twelve days after treatment and are shown in Table 7.

TABLE 6

| Herbicide No. 2 | Antidote No. 10 | Antidote No. 18 | % Plant Inhibition | | | | | | |
|---|---|---|---|---|---|---|---|---|---|
| Kg/Ha | Kg/Ha | Kg/Ha | Corn | GRSO | SOBE | WH | Rice | VELE | YEFT |
| 1.12 | — | — | 30 | 90 | 40 | 25 | 40 | 40 | 65 |
| — | 1.12 | — | 0 | 0 | 15 | 0 | 0 | 0 | 0 |
| — | — | 1.12 | 0 | 0 | 10 | 0 | 0 | 0 | 0 |
| 1.12 | 1.12 | — | 0 | 90 | 20 | 15 | 35 | 35 | 70 |
| 0.28 | 1.12 | — | 5 | 40 | 10 | 0 | 35 | 0 | 30 |
| 1.12 | — | 4.48 | 10 | 50 | 40 | 20 | 30 | 45 | 70 |
| 0.28 | — | 4.48 | 0 | 15 | 0 | 0 | 25 | 20 | 40 |
| 1.12 | — | 2.24 | 10 | 90 | 20 | 10 | 50 | 50 | 70 |
| 0.28 | — | 2.24 | 0 | 60 | 20 | 10 | 30 | 10 | 30 |
| 1.12 | — | 1.12 | 20 | 90 | 65 | 10 | 55 | 60 | 70 |
| 0.28 | — | 1.12 | 0 | 50 | 30 | 0 | 20 | 10 | 30 |
| 1.12 | — | 0.56 | 25 | 98 | 70 | 0 | 60 | 70 | 70 |
| 0.18 | — | 0.56 | 10 | 65 | 20 | 0 | 40 | 0 | 30 |
| 1.12 | — | 0.28 | 25 | 80 | 75 | 10 | 70 | 60 | 75 |
| 0.28 | — | 0.28 | 10 | 40 | 60 | 0 | 50 | 10 | 35 |

In this test, Antidote No. 10 was twice or greater as active as Antidote No. 18 as a corn safener against Herbicide No. 2. At 2.24 kg/ha, Antidote No. 18 reduced corn injury by the herbicide from 30% to 10% and at 4.48 kg/ha sorghum injury by the herbicide was reduced from 55% to 15% by Antidote No. 18.

TABLE 7

| Antidote No. | Rate Kg/Ha | Herbicide No. | Rate Kg/Ha | % Plant Inhibition | | | | | | |
|---|---|---|---|---|---|---|---|---|---|---|
| | | | | Corn | GRSO | SOBE | WH | Rice | YEFT | VELE |
| — | — | 1 | 2.24 | 20 | 30 | 80 | 30 | 20 | 75 | 75 |
| — | — | 1 | 0.56 | 0 | 20 | 80 | 0 | 20 | 60 | 60 |
| — | — | 1 | 0.14 | 0 | 0 | 70 | 0 | 0 | 20 | 20 |
| — | — | 2 | 1.12 | 55 | 98 | 65 | 80 | 95 | 95 | 85 |
| — | — | 2 | 0.28 | 10 | 90 | 35 | 20 | 70 | 40 | 40 |
| — | — | 2 | 0.07 | 0 | 60 | 25 | 0 | 60 | 40 | 20 |
| — | — | 5 | 1.12 | 80 | 98 | 95 | 95 | 70 | 95 | 95 |
| — | — | 5 | 0.28 | 30 | 60 | 95 | 80 | 25 | 50 | 80 |
| — | — | 5 | 0.07 | 0 | 10 | 80 | 10 | 0 | 0 | 30 |
| 13 | 2.24 | 5 | 1.12 | 55 | 98 | 95 | 98 | 70 | 90 | 95 |
| 13 | 2.24 | 5 | 0.28 | 25 | 60 | 95 | 80 | 20 | 60 | 80 |
| 13 | 2.24 | 5 | 0.07 | 0 | 10 | 70 | 20 | 0 | 20 | 50 |
| 13 | 2.24 | 2 | 1.12 | 15 | 90 | 60 | 75 | 95 | 85 | 80 |
| 13 | 2.24 | 2 | 0.28 | 0 | 85 | 60 | 15 | 80 | 40 | 40 |
| 13 | 2.24 | 2 | 0.07 | 0 | 40 | 30 | 0 | 60 | 30 | 20 |
| 13 | 2.24 | 1 | 2.24 | 15 | 20 | 80 | 10 | 30 | 70 | 70 |
| 13 | 2.24 | 1 | 0.56 | 10 | 0 | 70 | 0 | 0 | 40 | 60 |
| 13 | 2.24 | 1 | 0.14 | 0 | 0 | 70 | 0 | 0 | 20 | 20 |
| 14 | 2.24 | 5 | 1.12 | 80 | 98 | 95 | 98 | 80 | 90 | 95 |
| 14 | 2.24 | 5 | 0.28 | 15 | 45 | 90 | 85 | 30 | 70 | 80 |
| 14 | 2.24 | 5 | 0.07 | 0 | 0 | 80 | 30 | 10 | 30 | 60 |
| 14 | 2.24 | 2 | 1.12 | 0 | 90 | 60 | 80 | 95 | 85 | 85 |
| 14 | 2.24 | 2 | 0.28 | 0 | 90 | 60 | 80 | 95 | 85 | 85 |
| 14 | 2.24 | 2 | 0.07 | 0 | 25 | 35 | 0 | 50 | 20 | 20 |
| 14 | 2.24 | 1 | 2.24 | 10 | 20 | 80 | 10 | 40 | 70 | 80 |
| 14 | 2.24 | 1 | 0.56 | 0 | 0 | 70 | 0 | 10 | 40 | 60 |
| 14 | 2.24 | 1 | 0.14 | 0 | 0 | 70 | 0 | 0 | 10 | 30 |
| 15 | 2.24 | 5 | 1.12 | 85 | 100 | 95 | 95 | 75 | 90 | 90 |
| 15 | 2.24 | 5 | 0.28 | 55 | 65 | 95 | 85 | 55 | 80 | 90 |
| 15 | 2.24 | 5 | 0.07 | 15 | 10 | 80 | 30 | 10 | 30 | 50 |
| 15 | 2.24 | 2 | 1.12 | 0 | 98 | 40 | 70 | 90 | 90 | 85 |

TABLE 7-continued

| Antidote No. | Rate Kg/Ha | Herbicide No. | Rate Kg/Ha | % Plant Inhibition | | | | | | |
|---|---|---|---|---|---|---|---|---|---|---|
| | | | | Corn | GRSO | SOBE | WH | Rice | YEFT | VELE |
| 15 | 2.24 | 2 | 0.28 | 0 | 75 | 20 | 20 | 70 | 40 | 55 |
| 15 | 2.24 | 2 | 0.07 | 0 | 25 | 10 | 0 | 40 | 30 | 30 |
| 15 | 2.24 | 1 | 2.24 | 20 | 80 | 80 | 60 | 50 | 75 | 85 |
| 15 | 2.24 | 1 | 0.56 | 0 | 10 | 80 | 0 | 20 | 55 | 70 |
| 15 | 2.24 | 1 | 0.14 | 0 | 0 | 70 | 0 | 0 | 20 | 20 |
| 16 | 2.24 | 5 | 1.12 | 50 | 95 | 95 | 95 | 70 | 90 | 95 |
| 16 | 2.24 | 5 | 0.28 | 30 | 65 | 95 | 80 | 30 | 60 | 70 |
| 16 | 2.24 | 5 | 0.07 | 10 | 10 | 95 | 35 | 0 | 20 | 20 |
| 16 | 2.24 | 2 | 1.12 | 18 | 95 | 60 | 70 | 90 | 80 | 80 |
| 16 | 2.24 | 2 | 0.28 | 10 | 75 | 40 | 20 | 60 | 40 | 40 |
| 16 | 2.24 | 2 | 0.07 | 0 | 40 | 50 | 0 | 30 | 30 | 20 |
| 16 | 2.24 | 1 | 2.24 | 10 | 60 | 80 | 60 | 50 | 90 | 80 |
| 16 | 2.24 | 1 | 0.56 | 0 | 10 | 80 | 0 | 20 | 60 | 70 |
| 16 | 2.24 | 1 | 0.14 | 0 | 0 | 70 | 0 | 0 | 20 | 20 |
| 17 | 2.24 | 5 | 1.12 | 60 | 100 | 95 | 95 | 75 | 90 | 95 |
| 17 | 2.24 | 5 | 0.28 | 40 | 80 | 95 | 85 | 60 | 80 | 80 |
| 17 | 2.24 | 5 | 0.07 | 15 | 0 | 90 | 30 | 0 | 20 | 30 |
| 17 | 2.24 | 2 | 1.12 | 25 | 95 | 25 | 60 | 95 | 80 | 80 |
| 17 | 2.24 | 2 | 0.28 | 10 | 90 | 40 | 20 | 80 | 60 | 60 |
| 17 | 2.24 | 2 | 0.07 | 0 | 65 | 15 | 0 | 40 | 20 | 20 |
| 17 | 2.24 | 1 | 2.24 | 35 | 90 | 90 | 50 | 70 | 90 | 85 |
| 17 | 2.24 | 1 | 0.56 | 20 | 50 | 80 | 10 | 40 | 80 | 70 |
| 17 | 2.24 | 1 | 0.14 | 0 | 10 | 70 | 0 | 10 | 40 | 40 |
| 18 | 2.24 | 5 | 1.12 | 70 | 98 | 95 | 95 | 80 | 90 | 90 |
| 18 | 2.24 | 5 | 0.28 | 45 | 70 | 90 | 80 | 60 | 75 | 70 |
| 18 | 2.24 | 5 | 0.07 | 0 | 30 | 90 | 20 | 10 | 30 | 40 |
| 18 | 2.24 | 2 | 1.12 | 20 | 98 | 70 | 15 | 95 | 85 | 85 |
| 18 | 2.24 | 2 | 0.28 | 0 | 80 | 20 | 15 | 75 | 45 | 50 |
| 18 | 2.24 | 2 | 0.07 | 0 | 40 | 20 | 0 | 50 | 20 | 20 |
| 18 | 2.24 | 1 | 2.24 | 30 | 80 | 90 | 30 | 60 | 85 | 85 |
| 18 | 2.24 | 1 | 0.56 | 0 | 10 | 70 | 0 | 10 | 40 | 40 |
| 18 | 2.24 | 1 | 0.14 | 0 | 0 | 80 | 0 | 0 | 20 | 30 |

EXAMPLE 8

The same procedure described in Example 7 was conducted using the same antidotes to safen the same crops against Herbicide No. 4. Observations were taken thirteen days after treatment. Test results are shown in Table 8.

TABLE 8

| Antidote No. | Rate Kg/Ha | Herb. No. 4 Kg/Ha | Corn | GRSO | SOBE | WH | Rice | YEFT | VELE |
|---|---|---|---|---|---|---|---|---|---|
| — | — | 0.02 | 70 | 95 | 95 | 60 | 80 | 80 | 0 |
| — | — | 0.004 | 10 | 40 | 50 | 10 | 40 | 50 | 0 |
| — | — | 0.001 | 0 | 20 | 40 | 0 | 0 | 0 | 0 |
| 13 | 2.24 | 0.02 | 15 | 90 | 98 | 30 | 60 | 80 | 30 |
| 13 | 2.24 | 0.004 | 0 | 50 | 60 | 0 | 10 | 30 | 0 |
| 13 | 2.24 | 0.001 | 0 | 20 | 40 | 0 | 0 | 0 | 0 |
| 14 | 2.24 | 0.02 | 45 | 90 | 98 | 70 | 80 | 80 | 60 |
| 14 | 2.24 | 0.004 | 0 | 40 | 60 | 0 | 30 | 0 | 0 |
| 14 | 2.24 | 0.001 | 0 | 0 | 60 | 0 | 0 | 0 | 0 |
| 15 | 2.24 | 0.02 | 35 | 90 | 98 | 60 | 70 | 80 | 40 |
| 15 | 2.24 | 0.004 | 0 | 50 | 40 | 0 | 30 | 40 | 20 |
| 15 | 2.24 | 0.001 | 0 | 10 | 40 | 0 | 0 | 0 | 0 |
| 16 | 2.24 | 0.02 | 35 | 95 | 98 | 30 | 70 | 90 | 70 |
| 16 | 2.24 | 0.004 | 10 | 40 | 80 | 10 | 40 | 40 | 10 |
| 16 | 2.24 | 0.001 | 0 | 20 | 0 | 0 | 0 | 0 | 0 |
| 17 | 2.24 | 0.02 | 75 | 95 | 100 | 35 | 80 | 90 | 30 |
| 17 | 2.24 | 0.004 | 0 | 50 | 30 | 0 | 25 | 30 | 30 |
| 17 | 2.24 | 0.001 | 0 | 20 | 30 | 0 | 0 | 20 | 0 |
| 18 | 2.24 | 0.02 | 60 | 90 | 95 | 20 | 70 | 90 | 30 |
| 18 | 2.24 | 0.004 | 20 | 60 | 60 | 10 | 50 | 80 | 20 |
| 18 | 2.24 | 0.001 | 0 | 0 | 0 | 0 | 0 | 0 | 0 |

Referring to the data in Tables 7 and 8, the test results indicated that the more readily safened herbicides were Nos. 2 and 4. Antidote Nos. 14 and 15 were the most active to safen corn against Herbicide No. 2, although all safeners were active to varying degrees against that herbicide. At 2.24 kg/ha, Antidotes 14 and 15 reduced corn injury by Herbicide No. 2 at 1.12 kg/ha from 55% to 0%. For safening Herbicide No. 4 to corn, Antidote No. 13 at 2.24 kg/ha was the most active safener followed by Antidote Nos. 15 and 16. Antidote No. 13 reduced corn injury by Herbicide No. 4 at 0.02 kg/ha from 70% to 15%. Antidote Nos. 13, 16 and 17 at 2.24 kg/ha reduced corn injury from Herbicide No. 5 at 1.12 kg/ha from 80% to 50–60%.

Antidote No. 18 at 2.24 kg/ha reduced wheat injury from Herbicide No. 2 at 1.12 kg/ha from 80% to 15%, and injury by Herbicide No. 4 at 0.02 kg/ha from 60% to 40%.

Antidote Nos. 16 and 18 at 2.24 kg/ha reduced soybean injury from Herbicide No. 4 at 0.001 kg/ha from 40% to 0%.

Finally, Antidote Nos. 13 and 14 reduced sorghum injury by Herbicide No. 2 at 1.12 kg/ha from 60% to 25–40%. Unexpectedly, injury by Herbicide No. 1 at 2.24 kg/ha was enhanced noticeably by Antidote Nos. 15, 16, 17 and 18.

This reflects the unpredictability of antidotal action by various antidotes against various herbicides, at least under some test conditions.

EXAMPLE 9

In this example, the safening action by Antidote Nos. 10 and 21 was tested against Herbicide Nos. 1–6 and 8 in the same plant species as in the preceding examples. The procedure described in Example 1 was followed in this test. Test results were observed twelve (12) days after treatment and are shown in Table 9.

TABLE 9

| Antidote No. | Rate Kg/Ha | Herbicide No. | Rate Kg/Ha | % Plant Inhibition | | | | | | |
|---|---|---|---|---|---|---|---|---|---|---|
| | | | | Corn | GRSO | SOBE | WH | Rice | YEFT | VELE |
| — | — | 1 | 2.24 | 65 | 98 | 95 | 70 | 95 | 90 | 90 |
| — | — | 1 | 0.56 | 35 | 95 | 75 | 65 | 90 | 85 | 80 |
| — | — | 1 | 0.14 | 0 | 45 | 60 | 0 | 20 | 40 | 60 |
| — | — | 2 | 1.12 | 35 | 95 | 25 | 60 | 90 | 90 | 90 |
| — | — | 2 | 0.28 | 0 | 90 | 0 | 40 | 80 | 60 | 70 |
| — | — | 2 | 0.07 | 0 | 20 | 0 | 0 | 60 | 40 | 20 |
| — | — | 3 | 4.48 | 60 | 95 | 80 | 55 | 95 | 80 | 80 |
| — | — | 3 | 1.12 | 0 | 35 | 40 | 15 | 70 | 0 | 20 |
| — | — | 3 | 0.28 | 0 | 20 | 0 | 0 | 65 | 0 | 0 |
| — | — | 4 | 0.02 | 45 | 95 | 70 | 80 | 90 | 20 | 95 |
| — | — | 4 | 0.004 | 15 | 55 | 0 | 0 | 80 | 10 | 70 |
| — | — | 4 | 0.001 | 0 | 0 | 0 | 0 | 0 | 0 | 0 |
| — | — | 5 | 1.12 | 85 | 80 | 90 | 90 | 95 | 95 | 95 |
| — | — | 5 | 0.28 | 70 | 65 | 75 | 90 | 90 | 90 | 90 |
| — | — | 5 | 0.07 | 0 | 0 | 70 | 60 | 90 | 80 | 60 |
| — | — | 6 | 1.12 | 70 | 90 | 65 | 50 | 90 | 60 | 90 |
| — | — | 6 | 0.28 | 40 | 40 | 20 | 0 | 70 | 10 | 70 |
| — | — | 6 | 0.007 | 0 | 0 | 0 | 0 | 0 | 0 | 0 |
| — | — | 8 | 0.14 | 85 | 98 | 65 | 90 | 95 | 60 | 90 |
| — | — | 8 | 0.04 | 45 | 80 | 10 | 70 | 90 | 20 | 40 |
| — | — | 8 | 0.009 | 0 | 0 | 0 | 0 | 80 | 0 | 40 |
| — | — | 9 | 0.14 | 20 | 95 | 20 | 90 | 100 | 90 | 95 |
| — | — | 9 | 0.04 | 0 | 80 | 0 | 40 | 95 | 70 | 70 |
| — | — | 9 | 0.009 | 0 | 40 | 0 | 0 | 70 | 0 | 60 |
| 21 | 2.24 | 9 | 0.009 | 0 | 0 | 0 | 0 | 30 | 0 | 0 |
| 21 | 2.24 | 9 | 0.04 | 0 | 35 | 0 | 0 | 85 | 80 | 60 |
| 21 | 2.24 | 9 | 0.14 | 0 | 100 | 0 | 20 | 95 | 80 | 80 |
| 21 | 2.24 | 8 | 0.009 | 0 | 0 | 0 | 0 | 80 | 0 | 0 |
| 21 | 2.24 | 8 | 0.04 | 20 | 70 | 10 | 60 | 90 | 20 | 40 |
| 21 | 2.24 | 8 | 0.14 | 65 | 95 | 50 | 90 | 95 | 60 | 90 |
| 21 | 2.24 | 6 | 0.07 | 0 | 0 | 0 | 0 | 0 | 0 | 0 |
| 21 | 2.24 | 6 | 0.28 | 0 | 20 | 20 | 10 | 30 | 20 | 40 |
| 21 | 2.24 | 6 | 1.12 | 30 | 85 | 50 | 40 | 75 | 60 | 60 |
| 21 | 2.24 | 5 | 0.07 | 0 | 0 | 50 | 40 | 70 | 40 | 40 |
| 21 | 2.24 | 5 | 0.28 | 35 | 40 | 90 | 90 | 90 | 90 | 85 |
| 21 | 2.24 | 5 | 1.12 | 65 | 75 | 85 | 90 | 95 | 95 | 95 |
| 21 | 2.24 | 4 | 0.001 | 0 | 0 | 0 | 0 | 0 | 0 | 0 |
| 21 | 2.24 | 4 | 0.004 | 0 | 20 | 0 | 0 | 70 | 20 | 60 |
| 21 | 2.24 | 4 | 0.02 | 10 | 90 | 60 | 50 | 80 | 20 | 80 |
| 21 | 2.24 | 3 | 0.28 | 0 | 0 | 0 | 0 | 60 | 0 | 0 |
| 21 | 2.24 | 3 | 1.12 | 0 | 20 | 40 | 20 | 90 | 30 | 20 |
| 21 | 2.24 | 3 | 4.48 | 0 | 50 | 75 | 50 | 95 | 70 | 80 |
| 21 | 2.24 | 2 | 0.07 | 0 | 0 | 0 | 0 | 0 | 0 | 0 |
| 21 | 2.24 | 2 | 0.28 | 0 | 20 | 0 | 20 | 65 | 40 | 40 |
| 21 | 2.24 | 2 | 1.12 | 0 | 75 | 25 | 40 | 90 | 80 | 80 |
| 21 | 2.24 | 1 | 0.14 | 0 | 0 | 70 | 0 | 80 | 0 | 40 |
| 21 | 2.24 | 1 | 0.56 | 5 | 65 | 80 | 30 | 60 | 80 | 60 |
| 21 | 2.24 | 1 | 2.24 | 40 | 90 | 95 | 60 | 80 | 90 | 90 |
| 10 | 2.24 | 9 | 0.009 | 0 | 0 | 0 | 0 | 80 | 30 | 30 |
| 10 | 2.24 | 9 | 0.04 | 0 | 40 | 0 | 15 | 90 | 70 | 80 |
| 10 | 2.24 | 9 | 0.14 | 0 | 98 | 0 | 45 | 95 | 85 | 90 |
| 10 | 2.24 | 8 | 0.009 | 0 | 0 | 0 | 0 | 70 | 0 | 30 |
| 10 | 2.24 | 8 | 0.04 | 35 | 95 | 20 | 80 | 90 | 30 | 70 |
| 10 | 2.24 | 8 | 0.14 | 75 | 98 | 70 | 90 | 95 | 80 | 90 |
| 10 | 2.24 | 6 | 0.07 | 0 | 0 | 0 | 0 | 0 | 0 | 0 |
| 10 | 2.24 | 6 | 0.28 | 0 | 30 | 15 | 0 | 40 | 30 | 40 |
| 10 | 2.24 | 6 | 1.12 | 0 | 90 | 75 | 70 | 95 | 90 | 95 |
| 10 | 2.24 | 5 | 0.07 | 0 | 0 | 65 | 45 | 40 | 60 | 60 |

TABLE 9-continued

| Antidote | Rate | Herbicide | Rate | % Plant Inhibition | | | | | | |
|---|---|---|---|---|---|---|---|---|---|---|
| No. | Kg/Ha | No. | Kg/Ha | Corn | GRSO | SOBE | WH | Rice | YEFT | VELE |
| 10 | 2.24 | 5 | 0.28 | 30 | 40 | 80 | 90 | 90 | 95 | 95 |
| 10 | 2.24 | 5 | 1.12 | 75 | 90 | 90 | 95 | 95 | 95 | 95 |
| 10 | 2.24 | 4 | 0.001 | 0 | 0 | 0 | 0 | 0 | 0 | 0 |
| 10 | 2.24 | 4 | 0.004 | 0 | 15 | 0 | 0 | 20 | 20 | 20 |
| 10 | 2.24 | 4 | 0.02 | 0 | 70 | 45 | 60 | 80 | 20 | 80 |
| 10 | 2.24 | 3 | 0.28 | 0 | 0 | 0 | 0 | 40 | 0 | 0 |
| 10 | 2.24 | 3 | 1.12 | 0 | 10 | 50 | 10 | 70 | 30 | 30 |
| 10 | 2.24 | 3 | 4.48 | 0 | 55 | 80 | 55 | 98 | 80 | 80 |
| 10 | 2.24 | 2 | 0.07 | 0 | 0 | 0 | 0 | 0 | 10 | 0 |
| 10 | 2.24 | 2 | 0.28 | 0 | 40 | 0 | 0 | 90 | 40 | 60 |
| 10 | 2.24 | 2 | 1.12 | 0 | 95 | 30 | 60 | 95 | 85 | 85 |
| 10 | 2.24 | 1 | 0.14 | 0 | 0 | 65 | 0 | 0 | 80 | 70 |
| 10 | 2.24 | 1 | 0.56 | 0 | 50 | 80 | 40 | 80 | 90 | 80 |
| 10 | 2.24 | 1 | 2.24 | 10 | 95 | 90 | 90 | 95 | 90 | 90 |

In the test of this example, Antidote Nos. 10 and 21 safened corn against all test herbicides. At 2.24 kg/ha these antidotes safened corn to Herbicide No. 2, reducing injury by 35%; reducing sorghum injury by 50–70%; injury to wheat by 20–40% and rice by 60%. Both antidotes slightly reduced the phytotoxicity of Herbicide No. 2 to the test weeds. Antidote No. 15 exhibited higher activity than No. 21 in reducing corn injury by Herbicide Nos. 1 and 6.

EXAMPLE 10

The example describes the results of tests with Antidote Nos. 18 and 20 to safen Herbicide Nos. 2 and 4 in corn, grain sorghum, soybean and wheat crops in the presence of green foxtail (GRFT); seeding johnsongrass (SEJG); barnyardgrass (BYGR); morningglory (MOGL) and velvetleaf weeds. The preplant incorporation ("PPI") procedure used in this example was the same as in preceding examples. Observations were made sixteen days after treatment. Test results are shown in Table 10.

Antidote Nos. 18 and 20 in this test were shown to reduce injury to wheat by Herbicide No. 4 at 0.02 kg/ha from 85% to 20–30% when the antidote rate was 2.24 kg/ha. These antidotes also provided some corn protection against Herbicide No. 4.

Still other tests were conducted to determine the efficacy of a variety of antidotal compounds against herbicides according to Formula I above as the primary herbicide in combination with various other compounds as co-herbicides in various crops. The results of those tests are described in Examples 11–14 below.

EXAMPLE 11

This example describes tests with Antidote Nos. 9, 10 and 12 to safen corn and grain sorghum against combinations of Herbicide No. 6 with acetochlor, metolachlor and EPTC, i.e., Co-herbicide Nos. A, B and D, respectively. The PPI test procedure used in this test was the same as described in Example 1. Observations were taken two weeks after treatment. Test results are shown in Table 11 in which test plants (not previously identified above) are identified by abbreviated symbols as follows:

TABLE 10

| Herbicide | Rate | Antidote | Rate | % Plant Inhibition | | | | | | | | |
|---|---|---|---|---|---|---|---|---|---|---|---|---|
| No. | Kg/Ha | No. | Kg/Ha | Corn | GRSO | SOBE | WH | GRFT | SEJG | BYGR | MOGL | VELE |
| 2 | 1.12 | — | — | 30 | 40 | 20 | 20 | 0 | 30 | 60 | 40 | 70 |
| 2 | 0.28 | — | — | 10 | 20 | 0 | 0 | 0 | 20 | 30 | 0 | 30 |
| 4 | 0.02 | — | — | 90 | 98 | 90 | 85 | 90 | 90 | 80 | 70 | 30 |
| 4 | 0.004 | — | — | 60 | 80 | 70 | 60 | 60 | 80 | 70 | 0 | 0 |
| 2 | 1.12 | 18 | 2.24 | 35 | 80 | 60 | 20 | 40 | 40 | 40 | 50 | 75 |
| 2 | 0.28 | 18 | 2.24 | 0 | 60 | 20 | 0 | 0 | 0 | 30 | 30 | 40 |
| 4 | 0.02 | 18 | 2.24 | 80 | 95 | 80 | 20 | 70 | 80 | 90 | 60 | 20 |
| 4 | 0.004 | 18 | 2.24 | 40 | 70 | 60 | 20 | 30 | 50 | 60 | 0 | 10 |
| 2 | 1.12 | 20 | 2.24 | 20 | 70 | 50 | 40 | 70 | 60 | 70 | 80 | 90 |
| 2 | 0.28 | 20 | 2.24 | 15 | 70 | 40 | 0 | 20 | 20 | 30 | 0 | 40 |
| 4 | 0.02 | 20 | 2.24 | 85 | 95 | 80 | 30 | 60 | 70 | 70 | 40 | 20 |
| 4 | 0.004 | 20 | 2.24 | 50 | 60 | 40 | 10 | 40 | 40 | 50 | 30 | 0 |
| — | — | 18 | 2.24 | 0 | 0 | 0 | 0 | 0 | 0 | 0 | 0 | 0 |
| — | — | 20 | 2.24 | 0 | 0 | 0 | 0 | 0 | 0 | 0 | 0 | 0 |

Shattercane (SHCA);
Yellow nutsedge (YENS);
Black Nightshade (BLNS) and
Cocklebur (COBU).

EXAMPLE 12

In this example, tests were conducted to evaluate the safening effect of Antidote Nos. 3 and 18 against herbicidal combinations of Herbicide No. 2 and isoproturon (Co-herbicide E) in wheat, again using the test procedure as in

TABLE 11

| Herb. No. | Rate Kg/Ha | Co-Herbi-cide | Rate Kg/Ha | Anti-dote No. | Rate Kg/Ha | Corn | SHCA | BYGR | YENS | YEFT | GRSO | BLNS | VELE | COBU | MOGL |
|---|---|---|---|---|---|---|---|---|---|---|---|---|---|---|---|
| 6 | 1.12 | A | 0.56 | — | — | 75 | 90 | 100 | 95 | 100 | 95 | 90 | 60 | 0 | 0 |
| 6 | 0.28 | A | 0.56 | — | — | 5 | 90 | 100 | 100 | 100 | 85 | 80 | 30 | 0 | 0 |
| 6 | 1.12 | B | 1.12 | — | — | 65 | 85 | 100 | 90 | 98 | 45 | 90 | 60 | 0 | 0 |
| 6 | 0.28 | B | 1.12 | — | — | 10 | 85 | 100 | 90 | 98 | 80 | 80 | 30 | 0 | 0 |
| 6 | 1.12 | D | 1.12 | — | — | 60 | 90 | 95 | 90 | 90 | 100 | 85 | 60 | 0 | 0 |
| 6 | 0.28 | D | 1.12 | — | — | 0 | 45 | 90 | 70 | 85 | 85 | 75 | 30 | 0 | 0 |
| 6 | 1.12 | A | 0.56 | 9 | 2.24 | 20 | 95 | 100 | 100 | 100 | 95 | 90 | 70 | 0 | 0 |
| 6 | 0.28 | A | 0.56 | 9 | 2.24 | 0 | 75 | 100 | 95 | 100 | 70 | 85 | 40 | 0 | 0 |
| 6 | 1.12 | B | 1.12 | 9 | 2.24 | 35 | 90 | 100 | 100 | 100 | 98 | 90 | 75 | 0 | 0 |
| 6 | 0.28 | B | 1.12 | 9 | 2.24 | 0 | 80 | 100 | 100 | 100 | 70 | 80 | 40 | 0 | 0 |
| 6 | 1.12 | D | 1.12 | 9 | 2.24 | 25 | 85 | 75 | 90 | 85 | 95 | 75 | 60 | 0 | 0 |
| 6 | 0.28 | D | 1.12 | 9 | 2.24 | 0 | 60 | 70 | 70 | 70 | 70 | 50 | 30 | 0 | 0 |
| 6 | 1.12 | A | 0.56 | 10 | 2.24 | 15 | 90 | 100 | 100 | 100 | 90 | 95 | 80 | 0 | 0 |
| 6 | 0.28 | A | 0.56 | 10 | 2.24 | 0 | 30 | 100 | 85 | 100 | 25 | 80 | 20 | 0 | 0 |
| 6 | 1.12 | B | 1.12 | 10 | 2.24 | 15 | 70 | 100 | 90 | 100 | 85 | 80 | 60 | 0 | 0 |
| 6 | 0.28 | B | 1.12 | 10 | 2.24 | 0 | 20 | 100 | 100 | 100 | 10 | 70 | 0 | 0 | 0 |
| 6 | 1.12 | D | 1.12 | 10 | 2.24 | 10 | 75 | 80 | 80 | 80 | 90 | 80 | 40 | 0 | 0 |
| 6 | 0.28 | D | 1.12 | 10 | 2.24 | 0 | 60 | 80 | 70 | 70 | 70 | 50 | 0 | 0 | 0 |
| 6 | 1.12 | A | 0.56 | 12 | 2.24 | 40 | 95 | 100 | 98 | 100 | 95 | 90 | 80 | 0 | 0 |
| 6 | 0.28 | A | 0.56 | 12 | 2.24 | 0 | 85 | 100 | 90 | 100 | 90 | 90 | 60 | 0 | 0 |
| 6 | 1.12 | B | 1.12 | 12 | 2.24 | 50 | 90 | 100 | 90 | 100 | 95 | 95 | 70 | 0 | 0 |
| 6 | 0.28 | B | 1.12 | 12 | 2.24 | 5 | 80 | 100 | 85 | 100 | 95 | 80 | 60 | 0 | 0 |
| 6 | 1.12 | D | 1.12 | 12 | 2.24 | 40 | 90 | 80 | 80 | 100 | 95 | 85 | 80 | 30 | 40 |
| 6 | 0.28 | D | 1.12 | 12 | 2.24 | 15 | 80 | 60 | 70 | 85 | 95 | 80 | 70 | 0 | 0 |

In the above test all of combinations of Herbicide No. 6 applied at 1.12 kg/ha with Co-herbicides A, B and D were safened to corn with all of the test antidotes. Antidote No. 10 was the most active safener, followed by Antidote No. 9. At 2.24 kg/ha Antidote No. 10 reduced corn injury from 60–75% to 10–15% and also reduced sorghum injury and shattercane activity when mixed in Herbicide No. 6 plus Co-herbicides A and B.

the foregoing examples. In this test, the weed catchwood bedstraw (Galium aparine), commonly associated with wheat cultures, was the test weed. Observations were made sixteen days after treatment of the plants with the test chemicals. Test results are shown in Table 12, wherein the above weed is identified by the abbreviation "CWBS"; "WH" symbolizes wheat.

TABLE 12

| Antidote No. | Rate Kg/Ha | (Co-) Herb. No. | Rate Kg/Ha | Co-Herb. E | Rate Kg/Ha | % Plant Inhibition WH | CWBS |
|---|---|---|---|---|---|---|---|
| — | — | 2 | 2.24 | — | — | 95 | 100 |
| — | — | 2 | 0.56 | — | — | 75 | 100 |
| — | — | E | 4.48 | — | — | 20 | 100 |
| — | — | E | 1.12 | — | — | 10 | 90 |
| — | — | 2 | 2.24 | E | 4.48 | 90 | 100 |
| — | — | 2 | 2.24 | E | 1.12 | 75 | 100 |
| — | — | 2 | 0.56 | E | 4.48 | 75 | 100 |
| — | — | 2 | 0.56 | E | 1.12 | 70 | 100 |
| 3 | 2.24 | 2 | 2.24 | — | — | 95 | 100 |
| 3 | 2.24 | 2 | 0.56 | — | — | 70 | 100 |
| 3 | 2.24 | E | 4.48 | — | — | 20 | 100 |
| 3 | 2.24 | E | 1.12 | — | — | 10 | 100 |
| 3 | 2.24 | 2 | 2.24 | E | 4.48 | 95 | 100 |
| 3 | 2.24 | 2 | 2.24 | E | 1.12 | 90 | 100 |
| 3 | 2.24 | 2 | 0.56 | E | 4.48 | 65 | 100 |
| 3 | 2.24 | 2 | 0.56 | E | 1.12 | 70 | 100 |
| 18 | 2.24 | 2 | 2.24 | — | — | 35 | 100 |
| 18 | 2.24 | 2 | 0.56 | — | — | 30 | 100 |
| 18 | 2.24 | E | 4.48 | — | — | 15 | 80 |

TABLE 12-continued

| Antidote No. | Rate Kg/Ha | (Co-) Herb. No. | Rate Kg/Ha | Co-Herb. E | Rate Kg/Ha | % Plant Inhibition WH | CWBS |
|---|---|---|---|---|---|---|---|
| 18 | 2.24 | E | 1.12 | — | — | 0 | 70 |
| 18 | 2.24 | 2 | 2.24 | E | 4.48 | 40 | 100 |
| 18 | 2.24 | 2 | 2.24 | E | 1.12 | 20 | 100 |
| 18 | 2.24 | 2 | 0.56 | E | 4.48 | 40 | 100 |
| 18 | 2.24 | 2 | 0.56 | E | 1.12 | 25 | 100 |
| 3 | 2.24 | — | — | — | — | 0 | 0 |
| 18 | 2.24 | — | — | — | — | 0 | 0 |

In the above test Antidote No. 18 at 2.24 kg/ha reduced wheat injury by the combination of Herbicide No. 2 (at 2.24 kg/ha) and Co-herbicide E at 4.48 kg/ha from 90–95% to 35–40%. Antidote No. 3 was not shown to be particularly effective against the above herbicide/co-herbicide combination in wheat under the test conditions.

EXAMPLE 13

This example describes the results of tests to evaluate the antidotal efficacy of Antidote Nos. 1, 2 and 6 to safen rice against the combined herbicidal effects of Herbicide No. 2 and butachlor (Co-herbicide H). The test procedure was the same as in preceding examples. Barnyardgrass (BYGR) was the test weed. Observations were made thirteen days after treatment. Test results are shown in Table 13.

The data in the above test indicates that Antidote Nos. 2 and 6 reduced butachlor injury from 50% to 0–20% at 4.48 kg/ha of butachlor. However, combinations of Herbicide No. 1 at 0.28 kg/ha with or without butachlor at 1.12 kg/ha were not effectively safened by the test antidotes under the conditions of this test.

EXAMPLE 14

In this example Antidote Nos. 10 and 21 were tested for their efficacy against the combined herbicidal effects of Herbicide No. 2 and Co-herbicide B (metolachlor) to protect corn in the presence of yellow foxtail (Yeft), barnyardgrass (Bygr) and shattercane (Shca), under PPI conditions, the procedure used in the foregoing examples. Observations were made eight days after treatment. Test results are shown in Table 14.

TABLE 13

| Antidote No. | Rate Kg/Ha | (Co-) Herb. No. | Rate Kg/Ha | Co-Herb. E | Rate Kg/Ha | T Plant Inhibition Rice | BYGR |
|---|---|---|---|---|---|---|---|
| — | — | 2 | 1.12 | — | — | 90 | 95 |
| — | — | 2 | 0.28 | — | — | 40 | 75 |
| — | — | H | 4.48 | — | — | 50 | 100 |
| — | — | H | 1.12 | — | — | 35 | 100 |
| — | — | 2 | 1.12 | H | 4.48 | 80 | 100 |
| — | — | 2 | 1.12 | H | 1.12 | 80 | 100 |
| — | — | 2 | 0.28 | H | 4.48 | 40 | 100 |
| — | — | 2 | 0.28 | H | 1.12 | 50 | 100 |
| 2 | 2.24 | 2 | 1.12 | — | — | 85 | 90 |
| 2 | 2.24 | 2 | 0.28 | — | — | 70 | 70 |
| 2 | 2.24 | H | 4.48 | — | — | 20 | 100 |
| 2 | 2.24 | H | 1.12 | — | — | 0 | 100 |
| 2 | 2.24 | 2 | 1.12 | H | 4.48 | 75 | 100 |
| 2 | 2.24 | 2 | 1.12 | H | 1.12 | 90 | 100 |
| 2 | 2.24 | 2 | 0.28 | H | 4.48 | 70 | 100 |
| 2 | 2.24 | 2 | 0.28 | H | 1.12 | 55 | 100 |
| 6 | 2.24 | 2 | 1.12 | — | — | 95 | 95 |
| 6 | 2.24 | 2 | 0.28 | — | — | 85 | 70 |
| 6 | 2.24 | H | 4.48 | — | — | 0 | 100 |
| 6 | 2.24 | H | 1.12 | — | — | 0 | 100 |
| 6 | 2.24 | 2 | 1.12 | H | 4.48 | 100 | 100 |
| 6 | 2.24 | 2 | 1.12 | H | 1.12 | 99 | 100 |
| 6 | 2.24 | 2 | 0.28 | H | 4.48 | 55 | 100 |
| 6 | 2.24 | 2 | 0.28 | H | 1.12 | 50 | 100 |
| 1 | 2.24 | 2 | 1.12 | — | — | 95 | 95 |
| 1 | 2.24 | 2 | 0.28 | — | — | 80 | 60 |
| 1 | 2.24 | H | 4.48 | — | — | 70 | 90 |
| 1 | 2.24 | H | 1.12 | — | — | 70 | 100 |
| 1 | 2.24 | 2 | 1.12 | H | 4.48 | 95 | 100 |
| 1 | 2.24 | 2 | 1.12 | H | 1.12 | 70 | 100 |
| 1 | 2.24 | 2 | 0.28 | H | 4.48 | 75 | 100 |
| 1 | 2.24 | 2 | 0.28 | H | 1.12 | 70 | 100 |
| 2 | — | — | — | — | — | 0 | 0 |
| 6 | — | — | — | — | — | 0 | 0 |
| 1 | — | — | — | — | — | 0 | 0 |

TABLE 14

| Antidote No. | Rate Kg/Ha | Herbicide No. | Rate Kg/Ha | Co-Herbicide | Rate Kg/Ha | Corn | YEFT | BYGR | SHCA |
|---|---|---|---|---|---|---|---|---|---|
| — | — | 2 | 0.56 | — | — | 80 | 90 | 90 | 60 |
| — | — | 2 | 0.14 | — | — | 40 | 60 | 60 | 60 |
| — | — | — | — | B | 2.24 | 30 | 100 | 100 | 100 |
| — | — | — | — | B | 0.56 | 0 | 100 | 100 | 95 |
| — | — | 2 | 0.56 | B | 2.24 | 85 | 100 | 100 | 100 |
| — | — | 2 | 0.56 | B | 0.56 | 70 | 100 | 100 | 90 |
| — | — | 2 | 0.14 | B | 2.24 | 70 | 100 | 100 | 90 |
| — | — | 2 | 0.14 | B | 0.56 | 60 | 100 | 100 | 100 |
| 21 | 2.24 | 2 | 0.56 | — | — | 40 | 60 | 50 | 50 |
| 21 | 2.24 | 2 | 0.14 | — | — | 10 | 20 | 0 | 30 |
| 21 | 2.24 | — | — | B | 2.24 | 0 | 100 | 100 | 70 |
| 21 | 2.24 | — | — | B | 0.56 | 0 | 100 | 100 | 70 |
| 21 | 2.24 | 2 | 0.56 | B | 2.24 | 70 | 100 | 100 | 100 |
| 21 | 2.24 | 2 | 0.56 | B | 0.56 | 55 | 100 | 100 | 100 |
| 21 | 2.24 | 2 | 0.14 | B | 2.24 | 40 | 100 | 100 | 90 |
| 21 | 2.24 | 2 | 0.14 | B | 0.56 | 0 | 100 | 90 | 70 |
| 10 | 2.24 | 2 | 0.56 | — | — | 25 | 70 | 60 | 60 |
| 10 | 2.24 | 2 | 0.14 | — | — | 15 | 20 | 20 | 0 |
| 10 | 2.24 | 2 | — | B | 2.24 | 0 | 100 | 100 | 95 |
| 10 | 2.24 | 2 | — | B | 0.56 | 0 | 100 | 100 | 100 |
| 10 | 2.24 | 2 | 0.56 | B | 2.24 | 60 | 100 | 100 | 100 |
| 10 | 2.24 | 2 | 0.56 | B | 0.56 | 40 | 100 | 100 | 90 |
| 10 | 2.24 | 2 | 0.14 | B | 2.24 | 20 | 100 | 100 | 95 |
| 10 | 2.24 | 2 | 0.14 | B | 0.56 | 0 | 100 | 100 | 70 |
| 21 | 2.24 | — | — | — | — | 0 | 0 | 0 | 0 |
| 10 | 2.24 | — | — | — | — | 0 | 0 | 0 | 0 |

Reference to the data in Table 14 will show that Herbicide No. 2 alone or in combination with Co-Herbicide B was significantly moderated in phytotoxicity to corn by both Antidote Nos. 10 and 21, the former antidote being more active than the latter. At 2.24 kg/ha Antidote No. 10 reduced corn injury by the Herbicide No. 2/Co-herbicide B combination at rates of 0.14/2.24 kg/ha from 70% to 20%. Both antidotes reduced activity of Herbicide No. 2 against the narrowleaf weeds yellow foxtail and barnyardgrass, but did not reduce the activity of the Co-herbicide B.

EXAMPLE 15

This example was designed to evaluate the antidotal effectiveness of representative antidote compounds against herbicidal compounds according to Formula I either alone or in combination with co-herbicidal compounds when the antidotes are applied as a crop seed coating on crop seeds, e.g., corn and sorghum seeds, according to the procedure described below.

The following procedure was used to determine the interaction between a herbicide and antidote when the herbicide is topically applied to the soil surface and the antidote is applied to crop seed. Crop plant seed may be treated with the antidote either by contacting the seed with antidote in powder form or by contacting the seed with a solution or suspension of antidote compound dissolved or suspended in a suitable solvent, typically methylene chloride or toluene. Relative amounts of antidote compound and seed are used to provide an antidote-on-seed concentration, on a percent weight/weight basis, typically within the range of about 0.03 to 0.13%. Containers were filled and compacted with fumigated silt loam type soil to a depth of about 1.3 cm from the top of the container. A first container was designated as an untreated control, a second container was designated as a herbicide control, and a third container was designated as a herbicide+antidote test container. Untreated crop seed was placed in the first and second containers. Antidote-treated crop seed was placed in the third container. Then, each of the second and third containers was filled and leveled with a cover layer of soil having incorporated therein the selected herbicide at a pre-determined concentration. The first container was filled and leveled with soil containing no herbicide. All containers were given about 0.6 cm of overhead water to simulate an activating rainfall. The containers were placed on a greenhouse bench and sub-irrigated as required for the duration of the test. Plant response is typically observed within about three weeks after initial treatment; in this example the observation was made twelve days after treatment.

In this example, Antidotes No. 5 (common name "flurazole"), No. 10 and No. 8 (common name "oxabetrinil") were coated onto sorghum and corn seeds for testing with Herbicide No. 2, the herbicides alachlor (Co-herbicide G) or metolachlor (Co-herbicide B) and mixtures thereof. Yellow foxtail (YEFT), wild proso millet (WIPM), velvetleaf (VELE) and morningglory (MOGL) were present as the test weeds. Test results are shown in Table 15. The percent injury or inhibition values resulting from the herbicide treatments are shown under each test plant.

TABLE 15

| Antidote No. | Rate Kg/Ha | Herbicide No. | Rate Kg/Ha | Co-Herbicide | Rate Kg/Ha | % Plant Inhibition | | | | | |
|---|---|---|---|---|---|---|---|---|---|---|---|
| | | | | | | Corn | GRSO | YEFT | WIPM | VELE | MOGL |
| — | — | 2 | 0.56 | G | 0.28 | 35 | 90 | 90 | 90 | 75 | 40 |
| — | — | 2 | 0.14 | G | 0.28 | 10 | 80 | 90 | 90 | 60 | 30 |
| 5 | 0.28 | 2 | 0.56 | G | 0.28 | 60 | 95 | — | — | — | — |
| 5 | 0.28 | 2 | 0.14 | G | 0.28 | 20 | 30 | — | — | — | — |
| 8 | 0.28 | 2 | 0.56 | G | 0.28 | 15 | 70 | — | — | — | — |
| 8 | 0.28 | 2 | 0.14 | G | 0.28 | 15 | 40 | — | — | — | — |
| 10 | 0.28 | 2 | 0.56 | G | 0.28 | 10 | 60 | — | — | — | — |
| 10 | 0.28 | 2 | 0.14 | G | 0.28 | 15 | 35 | — | — | — | — |
| — | — | 2 | 0.56 | B | 0.28 | 30 | 95 | 90 | 90 | 70 | 50 |
| — | — | 2 | 0.14 | B | 0.28 | 0 | 75 | 95 | 95 | 40 | 20 |
| 5 | 0.28 | 2 | 0.56 | B | 0.28 | 45 | 70 | — | — | — | — |
| 5 | 0.28 | 2 | 0.14 | B | 0.28 | 15 | 25 | — | — | — | — |
| 8 | 0.28 | 2 | 0.56 | B | 0.28 | 0 | 50 | — | — | — | — |
| 8 | 0.28 | 2 | 0.14 | B | 0.28 | 0 | 20 | — | — | — | — |
| 10 | 0.28 | 2 | 0.56 | B | 0.28 | 15 | 35 | — | — | — | — |
| 10 | 0.28 | 2 | 0.14 | B | 0.28 | 10 | 20 | — | — | — | — |
| — | — | 2 | 0.56 | — | — | 35 | 95 | 80 | 80 | 70 | 20 |
| — | — | 2 | 0.14 | — | — | 10 | 60 | 0 | 0 | 20 | 0 |
| 5 | 0.28 | 2 | 0.56 | — | — | — | 90 | — | — | — | — |
| 5 | 0.28 | 2 | 0.14 | — | — | — | 30 | — | — | — | — |
| 8 | 0.28 | 2 | 0.56 | — | — | — | 75 | — | — | — | — |
| 8 | 0.28 | 2 | 0.14 | — | — | — | 25 | — | — | — | — |
| 10 | 0.28 | 2 | 0.56 | — | — | — | 75 | — | — | — | — |
| 10 | 0.28 | 2 | 0.14 | — | — | — | 25 | — | — | — | — |
| — | — | — | — | G | 0.28 | 10 | 50 | 90 | 90 | 0 | 0 |
| 5 | 0.28 | — | — | G | 0.28 | — | 15 | — | — | — | — |
| 8 | 0.28 | — | — | G | 0.28 | — | 0 | — | — | — | — |
| 10 | 0.28 | — | — | G | 0.28 | — | 0 | — | — | — | — |
| — | — | — | — | B | 0.28 | 0 | 40 | 90 | 90 | 0 | 0 |
| 5 | 0.28 | — | — | B | 0.28 | — | 0 | — | — | — | — |
| 8 | 0.28 | — | — | B | 0.28 | — | 0 | — | — | — | — |
| 10 | 0.28 | — | — | B | 0.28 | — | 0 | — | — | — | — |
| 5 | 0.28 | — | — | — | — | 0 | 0 | 0 | 0 | 0 | 0 |
| 8 | 0.28 | — | — | — | — | 0 | 0 | 0 | 0 | 0 | 0 |
| 10 | 0.28 | — | — | — | — | 0 | 0 | 0 | 0 | 0 | 0 |

The data in Table 15 indicate that Antidotes 8 and 10 provided higher safening of corn and sorghum against Herbicide No. 2 than did Antidote No. 5. At 0.28 kg/ha Antidote Nos. 8 and 10 reduced injury by Herbicide No. 2 at 0.56 kg/ha in combination with Co-herbicides B or G at 0.28 kg/ha from 30–35% to 0% to 15%. Antidote No. 5 at 0.25 kg/ha appeared to enhance corn injury (an occasional anomaly) by the same combination of herbicides.

At 0.28 kg/ha Antidotes 5 and 10 reduced sorghum injury by Herbicide No. 2 at 0.56 kg/ha with and without Co-herbicides B and G also at 0.56 kg/ha (20–55%), while Antidote No. 5 at 0.25 kg/ha did not reduce sorghum injury in this test. At the rate of 0.14 kg/ha for Herbicide No. 2 with and without Co-herbicides B and G at 0.28 kg/ha, all of the antidotes reduced injury to sorghum from 60–80% to 20–40%.

Since sorghum is normally safened by each of the test antidotes to commercially-acceptable levels against alachlor and metolachlor, it is believed that excess injury to sorghum was due to Herbicide No. 2. Accordingly, it is suggested that lower rates of that herbicide and/or higher concentrations of one or more of the antidotes as a seed coating would further reduce sorghum injury by the above mixtures of herbicides/co-herbicides. Adjustment of relative ratios of herbicide(s) and/or antidotes for maximum safety is standard practice.

Herbicide No. 5 at 0.56 kg/ha enhanced herbicidal activity against the broadleaf weed velvetleaf in combinations with alachlor or metolachlor.

EXAMPLE 16

TEST A. In other tests with safener-coated crop seeds, e.g., corn seeds, following the procedure described in Example 16, Antidotes 9, 10 and 13 were used to evaluate their efficacy against Herbicide No. 2 alone and in combination with primisulfuron (Co-herbicide F) in corn with velvetleaf as the weed.

Test data for observations in one test made at nine days after application (DAA) of the chemicals are shown in Table 16A. For informational purposes, plant injury observations were made for solvents and a surfactant present used in the seed coating procedure

TABLE 16A

| Antidote No. | Rate Kg/Ha | Herb. No. | Rate Kg/Ha | Co-Herb. | Rate Kg/Ha | % Inhibition (9 DAA) | |
|---|---|---|---|---|---|---|---|
| | | | | | | Corn | VELE |
| — | — | 2 | 2.24 | — | — | 60 | 45 |
| — | — | — | — | F | 1.12 | 25 | 80 |
| — | — | 2 | 2.24 | F | 1.12 | 60 | 70 |
| 10 | 2.24 | 2 | 2.24 | — | — | 35 | 30 |
| 10 | 2.24 | 2 | 2.24 | F | 1.12 | 28 | 98 |
| 9 | 2.24 | 2 | 2.24 | F | 1.12 | 35 | 95 |
| 13 | 2.24 | 2 | 2.24 | F | 1.12 | 45 | 80 |
| 10 | 2.24 | — | — | — | — | 20 | 0 |
| 9 | 2.24 | — | — | — | — | 20 | 0 |
| 13 | 2.24 | — | — | — | — | 15 | 0 |
| Acetone | | | | | | 0 | 0 |
| X-77 Surfactant (0.5%) | | | | | | 20 | 0 |
| Acetone/X-77 | | | | | | 20 | 0 |

TEST B. In a similar test, observations were taken at the time of seven days after application of the chemicals instead of nine days as in Test A. Primary interest in this test was to determine the effect, if any, on corn injury of a shortened observation period, together with test readings with three each of the antidotes and their combinations with the herbicide and/or co-herbicides instead of two as used in Test A. Test B results are shown in Table 16B; no weed was present in that test.

TABLE 16B

| Antidote No. | Rate Kg/Ha | Herb. No. | Rate Kg/Ha | Co— Herb. | Rate Kg/Ha | % Inhibition (7 DAA) Corn |
|---|---|---|---|---|---|---|
| — | — | 2 | 2.24 | — | — | 35 |
| — | — | — | — | F | 1.12 | 15 |
| — | — | 2 | 2.24 | F | 1.12 | 35 |
| 10 | 2.24 | 2 | 2.24 | — | — | 20 |
| 10 | 2.24 | — | — | F | 1.12 | 15 |
| 10 | 2.24 | 2 | 2.24 | F | 1.12 | 25 |
| 9 | 2.24 | 2 | 2.24 | — | — | 15 |
| 9 | 2.24 | — | — | F | 1.12 | 0 |
| 9 | 2.24 | 2 | 2.24 | F | 1.12 | 20 |
| 13 | 2.24 | 2 | 2.24 | — | — | 10 |
| 13 | 2.24 | — | — | F | 1.12 | 15 |
| 13 | 2.24 | 2 | 2.24 | F | 1.12 | 15 |
| Acetone/X77 | | | | | | 5 |

In the above tests, the data in Table 16A show that unsafened corn had 60% injury due to Herbicide No. 2 applied at 2.24 kg/ha. However, when the corn seed was coated the antidotes, also at 2.24 kg/ha, corn injury was reduced to 35%–45%. Still further reduction in corn injury by Herbicide No. 2 is shown in Table 16B, wherein under the Test B conditions, each of the antidotes at 2.24 kg/ha reduced corn injury by Herbicide No. 2 at 2.24 kg/ha with or without co-herbicide F at 1.12 kg/ha from 35% to 10–20%.

It appears that the higher corn injury due to Herbicide No. 2 with no safener present in Table 16A may be due to the longer exposure time of the herbicide to the unsafened corn seed.

As will be apparent, the data in the above tables reflect the fact that azolopyrimidine sulfonamide herbicides are susceptible of having their phytotoxicity to crops reduced by various antidotal (safener) compounds, while still providing control or suppression of various narrowleaf and broadleaf weeds. The data also reflect the common occurrence that the safening effect on various herbicides by various safeners will have different degrees of effect in different crops and weeds depending upon a variety of factors, including, relative concentrations of herbicides and/or co-herbicides and/or antidotes, weather and soil conditions, water content, etc., as well appreciated in the art.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, and polymethylene bisnaphthalene sulfonate. Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5–20 parts) of active ingredient, from about 0.25 to 25 parts (preferably 1–15 parts) of wetting agent, from about 0.25 to 25 parts (preferably 1.0–15 parts) of dispersant and from 5 to about 95 parts (preferably 5–50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1–10% by weight.

Aqueous suspensions or emulsions may be prepared by stirring a nonaqueous solution of a water-insoluble active ingredient and an emulsification agent with water until uniform and then homogenizing to give stable emulsion of very finely divided particles. The resulting concentrated aqueous suspension is characterized by its extremely small particle size, so that when diluted and sprayed, coverage is very uniform. Suitable concentrations of these formulations contain from about 0.1–60%, preferably 5–50% by weight of active ingredient, the upper limit being determined by the solubility limit of active ingredient in the solvent. Concentrates are usually solutions of active ingredient in water-immiscible or partially water-immiscible solvents together with a surface active agent. Suitable solvents for the active ingredient of this invention include dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 5 to 94 parts solvent, all parts being be weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate extender, a surface active agent can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, sulfonylureas, carbamates, acetamides, acetanilides, uracils, acetic acid or phenol derivatives, thiol-carbamates, triazoles, benzoic acid and its derivatives, nitrites, biphenyl ethers, nitrobenzenes, etc.

Fertilizers useful in combination with the active ingredients include, for example, ammonium nitrate, urea, potash and superphosphate. Other useful additaments include materials in which plant organisms take root and grow such as compost, manure, humus, sand and the like.

Herbicidal formulations of the types described above contemplated as within the purview of this invention are exemplified in several illustrative embodiments below.

|   |   | Weight Percent |
|---|---|---|
| I. Emulsifiable Concentrates | | |
| A. | Herbicide No. 1 | 11.0 |
|   | Antidote No. 9 | 10.0 |
|   | Free acid of complex organic phosphate or aromatic or aliphatic hydrophobe base (e.g., GAFAC RE-610, registered trademark of GAF Corp.) | 5.59 |
|   | Polyoxyethylene/polyoxypropylene block copolymer with butanol (e.g., Tergitol XH, registered trademark of Union Carbide Corp.) | |
|   | Phenol | 5.34 |
|   | Monochlorobenzene | 66.96 |
|   |   | 100.00 |
| B. | Herbicide No. 2 | 25.00 |
|   | Antidote No. 10 | 15.00 |
|   | Free acid of complex organic phosphate of aromatic or aliphatic hydrophobe base (e.g., GAFAC RE-610) | 5.00 |
|   | Polyoxyethylene/polyoxypropylene block copolymer with butanol (e.g., Tergitol XH) | 1.60 |
|   | Phenol | 4.75 |
|   | Monochlorobenzene | 48.65 |
|   |   | 100.00 |
| C. | Herbicide No. 3 | 12.0 |
|   | Antidote No. 1 | 12.0 |
|   | Free acid of complex organic phosphate or aromatic or aliphatic hydrophobe base (e.g., GAFAC RE-610, registered trademark of GAF Corp.) | 6.0 |
|   | Polyoxyethylene/polyoxypropylene block copolymer with butanol (e.g., Tergitol XH, registered trademark of Union Carbide Corp.) | 1.5 |
|   | Phenol | 5.5 |
|   | Monochlorobenzene | 63.0 |
|   |   | 100.00 |
| D. | Herbicide No. 4 | 20.0 |
|   | Antidote No. 2 | 15.0 |
|   | Free acid of complex organic phosphate | 5.00 |

-continued

|   |   | Weight Percent |
|---|---|---|
|   | of aromatic or aliphatic hydrophobe base (e.g., GAFAC RE-610 | |
|   | Polyoxyethylene/polyoxypropylene block copolymer with butanol (e.g., Tergitol XH) | 2.0 |
|   | Phenol | 5.0 |
|   | Monochlorobenzene | 53.0 |
|   |   | 100.00 |
| E. | Herbicide No. 5 | 11.0 |
|   | Antidote No. 3 | 5.0 |
|   | Free acid of complex organic phosphate or aromatic or aliphatic hydrophobe base (e.g. GAFAC RE-610, registered trademark of GAF Corp.) | 5.59 |
|   | Polyoxyethylene/polyoxypropylene block copolymer with butanol (e.g., Tergitol XH, registered trademark of Union Carbide Corp.) | 1.11 |
|   | Phenol | 5.34 |
|   | Monochlorobenzene | 71.96 |
|   |   | 100.00 |
| F. | Herbicide No. 6 | 15.00 |
|   | Antidote No. 4 | 10.00 |
|   | Free acid of complex organic phosphate of aromatic or aliphatic hydrophobe base (e.g., GAFAC RE-610 | 5.00 |
|   | Polyoxyethylene/polyoxypropylene block copolymer with butanol (e.g., Tergitol XH) | 1.60 |
|   | Phenol | 4.75 |
|   | Monochlorobenzene | 63.65 |
|   |   | 100.00 |
| II. Flowables | | |
| A. | Herbicide No. 7 | 15.0 |
|   | Antidote No. 5 | 10.0 |
|   | Methyl cellulose | 0.3 |
|   | Silica Aerogel | 1.5 |
|   | Sodium lignosulfonate | 3.5 |
|   | Sodium N-methyl-N-oleyl taurate | 1.0 |
|   | Water | 67.7 |
|   |   | 100.00 |
| B. | Herbicide No. 8 | 30.0 |
|   | Antidote No. 6 | 15.0 |
|   | Methyl cellulose | .3 |
|   | Silica aerogel | 1.5 |
|   | Sodium lignosulfonate | 3.5 |
|   | Sodium N-methyl-N-oleyl taurate | 1.0 |
|   | Water | 47.7 |
|   |   | 100.00 |
| C. | Herbicide No. 9 | 20.0 |
|   | Antidote No. 7 | 10.0 |
|   | Methyl cellulose | 0.3 |
|   | Silica Aerogel | 1.5 |
|   | Sodium lignosulfonate | 3.5 |
|   | Sodium N-methyl-N-oleyl taurate | 3.0 |
|   | Water | 62.0 |
|   |   | 100.00 |
| D. | Herbicide No. 1 | 20.0 |
|   | Antidote No. 8 | 25.0 |
|   | Methyl cellulose | 0.5 |
|   | Silica Aerogel | 2.0 |
|   | Sodium lignosulfonate | 3.5 |
|   | Sodium N-methyl-N-oleyl taurate | 2.0 |
|   | Water | 47.0 |
|   |   | 100.00 |
| E. | Herbicide No. 2 | 40.0 |
|   | Antidote No. 10 | 20.0 |
|   | Methyl cellulose | .3 |
|   | Silica aerogel | 1.5 |
|   | Sodium lignosulfonate | 3.5 |

-continued

| | | Weight Percent |
|---|---|---|
| | Sodium N-methyl-N-oleyl taurate | 1.0 |
| | Water | 33.7 |
| | | 100.00 |

III. Wettable Powders

| | | Weight Percent |
|---|---|---|
| A. | Herbicide No. 2 | 15.0 |
| | Antidote No. 10 | 10.0 |
| | Sodium lignosulfonate | 3.0 |
| | Sodium N-methyl-N-oleyl-taurate | 1.0 |
| | Amorphous silica (synthetic) | 71.0 |
| | | 100.0 |
| B. | Herbicide No. 4 | 60.0 |
| | Antidote No. 11 | 20.0 |
| | Sodium dioctyl sulfosuccinate | 1.25 |
| | Calcium lignosulfonate | 1.75 |
| | Amorphous silica (synthetic) | 17.0 |
| | | 100.0 |
| C. | Herbicide No. 5 | 10.0 |
| | Antidote No. 12 | 10.0 |
| | Sodium lignosulfonate | 3.0 |
| | Sodium N-methyl-N-oleyl-taurate | 1.0 |
| | Kaolinite clay | 86.0 |
| | | 100.00 |
| D. | Herbicide No. 6 | 20.0 |
| | Antidote No. 13 | 20.0 |
| | Sodium lignosulfonate | 3.0 |
| | Sodium N-methyl-N-oleyl-taurate | 1.0 |
| | Amorphous silica (synthetic) | 66.0 |
| | | 100.0 |
| E. | Herbicide No. 7 | 65.0 |
| | Antidote No. 14 | 10.0 |
| | Sodium dioctyl sulfosuccinate | 1.25 |
| | Calcium lignosulfonate | 1.75 |
| | Amorphous silica synthetic | 22.0 |
| | | 100.00 |
| F. | Herbicide No. 8 | 15.0 |
| | Antidote No. 15 | 15.0 |
| | Sodium lignosulfonate | 3.0 |
| | Sodium N-methyl-N-oleyl-taurate | 1.0 |
| | Kaolinite clay | 66.0 |
| | | 100.00 |

IV. Dusts

| | | Weight Percent |
|---|---|---|
| A. | Herbicide No. 9 | 2.0 |
| | Antidote No. 16 | 4.0 |
| | Attapulgite | 94.0 |
| | | 100.00 |
| B. | Herbicide No. 1 | 50.0 |
| | Antidote No. 10 | 20.0 |
| | Montmorillonite | 40.0 |
| | | 100.00 |
| C. | Herbicide No. 3 | 10.0 |
| | Antidote No. 11 | 10.0 |
| | Ethylene glycol | 1.0 |
| | Bentonite | 69.0 |
| | | 100.00 |
| D. | Herbicide No. 3 | 10.0 |
| | Antidote No. 12 | 12.0 |
| | Attapulgite | 78.0 |
| | | 100.00 |
| E. | Herbicide No. 4 | 50.0 |
| | Antidote No. 13 | 10.0 |
| | Montmorillonite | 40.0 |
| | | 100.00 |
| F. | Herbicide No. 5 | 30.0 |
| | Antidote No. 14 | 30.0 |

-continued

| | | Weight Percent |
|---|---|---|
| | Ethylene glycol | 1.0 |
| | Bentonite | 39.0 |
| | | 100.00 |
| G. | Herbicide No. 6 | 5.0 |
| | Antidote No. 15 | 5.0 |
| | Diatomaceous earth | 9.0 |
| | | 100.0 |

V. Granules

| | | Weight Percent |
|---|---|---|
| A. | Herbicide No. 7 | 15.0 |
| | Antidote No. 16 | 15.0 |
| | Granular attapulgite (20/40 mesh) | 70.0 |
| | | 100.0 |
| B. | Herbicide No. 8 | 30.0 |
| | Antidote No. 1 | 20.0 |
| | Diatomaceous earth (20/40) | 70.0 |
| | | 100.0 |
| C. | Herbicide No. 9 | 1.0 |
| | Antidote No. 4 | 2.0 |
| | Ethylene glycol | 5.0 |
| | Methylene blue | 0.1 |
| | Pyrophyllite | 91.9 |
| | | 100.0 |
| D. | Herbicide No. 1 | 15.0 |
| | Antidote No. 10 | 5.0 |
| | Pyrophyllite (20/40) | 80.0 |
| | | 100.0 |
| E. | Herbicide No. 2 | 15.0 |
| | Antidote No. 9 | 15.0 |
| | Granular attapulgite (20/40 mesh) | 70.0 |
| | | 100.0 |
| F. | Herbicide No. 3 | 20.0 |
| | Antidote No. 11 | 10.0 |
| | Diatomaceous earth (20/40) | 70.0 |
| | | 100.0 |
| G. | Herbicide No. 4 | 5.0 |
| | Antidote No. 12 | 5.0 |
| | Ethylene glycol | 5.0 |
| | Methylene blue | 0.5 |
| | Pyrophyllite | 89.0 |
| | | 100.00 |
| H. | Herbicide No. 5 | 10.0 |
| | Antidote No. 13 | 10.0 |
| | Pyrophyllite (20/40) | 80.0 |
| | | 100.0 |

VI. Suspension Concentrates

| | | Weight Percent |
|---|---|---|
| A. | Herbicide No. 1 | 16.0 |
| | Antidote No. 18 | 15.0 |
| | Nonylphenol ethoxylate 9.5 mole EO Sterox NJ | 13.8 |
| | Sodium lignosulfonate (Reax 88B) | 12.2 |
| | Water | 43.0 |
| | | 100.0 |
| B. | Herbicide No. 2 | 30.0 |
| | Antidote No. 19 | 10.0 |
| | Potassium salt of napthalene sulfonate formaldehyde condensate (DAXAD aag) | 9.0 |
| | Nonylphenol ethoxylate 10 mole EO (Igepal CO-660) | 9.0 |
| | Water | 42.0 |
| | | 100.0 |
| C. | Herbicide No. 3 | 10.0 |
| | Antidote No. 20 | 10.0 |
| | Sodium dioctyl sulfosuccinate Aerosol OTB | 11.0 |

|  |  | Weight Percent |
|---|---|---|
|  | Castor oil + 36 Ethylene oxide (FloMo 3G) | 11.0 |
|  | Methanol | 60.0 |
|  |  | 100.0 |
| D. | Herbicide No. 4 | 15.0 |
|  | Antidote No. 6 | 5.0 |
|  | Nonylphenol ethoxylate 9.5 mole EO Sterox NJ | 14.8 |
|  | Sodium lignosulfonate (Reax 88B) | 11.2 |
|  | Water | 54.0 |
|  |  | 100.0 |
| E. | Herbicide No. 5 | 30.0 |
|  | Antidote No. 7 | 30.0 |
|  | Potassium salt of napthalene sulfonate formaldehyde condensate (DAXAD aag) | 8.0 |
|  | Nonylphenol ethoxylate 10 mole EO (Igepal CO-660) | 7.0 |
|  | Water | 25.0 |
|  |  | 100.0 |
| F. | Herbicide No. 6 | 18.0 |
|  | Antidote No. 8 | 22.0 |
|  | Nonylphenol ethoxylate 9.5 mole EO Sterox NJ | 14.0 |
|  | Sodium lignosulfonate (Reax 88B) | 12.0 |
|  | Water | 34.0 |
|  |  | 100.0 |
| G. | Herbicide No. 7 | 25.0 |
|  | Antidote No. 9 | 9.0 |
|  | Potassium salt of napthalene sulfonate formaldehyde condensate (DAXAD aag) | 8.0 |
|  | Nonylphenol ethoxylate 10 mole EO (Igepal CO-660) | 10.0 |
|  | Water | 48.0 |
|  |  | 100.0 |
| H. | Herbicide No. 8 | 14.0 |
|  | Antidote No. 10 | 14.0 |
|  | Sodium dioctyl sulfosuccinate Aerosol OTB | 12.0 |
|  | Castor oil + 36 Ethylene oxide (FloMo 3G) | 12.0 |
|  | Methanol | 48.0 |
|  |  | 100.0 |

VII. Suspoemulsions

|  |  | Weight Percent |
|---|---|---|
| A. | Herbicide No. 9 | 15.0 |
|  | Antidote No. 1 | 15.0 |
|  | Calcium dodecylbenzene sulfonate/-polyoxyethylene ethers blend (e.g., Atlox 3437F) | 13.0 |
|  | Calcium dodecylbenzene sulfonate (FloMo 60H) | 9.0 |
|  | Sodium salt of a polymerized alkyl napthalene sulfonic acid (Daxad 1G) | 3.0 |
|  | Water | 45.0 |
|  |  | 100.0 |
| B. | Herbicide No. 1 | 20.0 |
|  | Co-Herbicide - acetochlor | 20.0 |
|  | Antidote No. 1 | 20.0 |
|  | Calcium dodecyl sulfonate/alkylaryl polyether alcohol blend | 9.0 |
|  | Sodium Lignosulfonate (Marasperse N-22) | 4.10 |
|  | Water | 37.0 |
|  |  | 100.0 |
| C. | Herbicide No. 2 | 20.0 |
|  | Co-Herbicide - alachlor | 20.0 |
|  | Antidote No. 10 | 15.0 |
|  | Calcium dodecylbenzene sulfonate/-polyoxyethylene ethers blend (Atlox ® 3437F) | 6.0 |
|  | Sodium dioctyl sulfosuccinate Aerosol OT | 5.0 |
|  | Water | 34.0 |
|  |  | 100.0 |
| D. | Herbicide No. 3 | 15.0 |
|  | Co-herbicide - acetochlor | 15.0 |
|  | Antidote No. 18 | 5.0 |
|  | Atlox 3437F | 9.0 |
|  | Sodium salt of a condensed napthalene sulfonic acid (Tamol SN) | 6.0 |
|  | Water | 70.0 |
|  |  | 100.0 |
| E. | Herbicide No. 1 | 20.0 |
|  | Co-Herbicide - butachlor | 20.0 |
|  | Antidote No. 10 | 20.0 |
|  | Monochlorobenzene | 10.0 |
|  | Atlox 3437F | 10.0 |
|  | Sodium lignosulfonate (Reax 88B) | 5.0 |
|  | Water | 55.0 |
|  |  | 100.0 |
| F. | Herbicide No. 2 | 35.0 |
|  | Co-Herbicide - pretilachlor | 20.0 |
|  | Antidote No. 10 | 20.0 |
|  | Calcium dodecylbenzene sulfonate/-polyoxyethylene ethers blend (e.g., Atlox 3437F) | 11.0 |
|  | Calcium dodecylbenzene sulfonate (FloMo 60H) | 6.0 |
|  | Sodium salt of a polymerized alkyl napthalene sulfonic acid (Daxad 1G) | 3.0 |
|  | Water | 5.0 |
|  |  | 100.0 |
| G. | Herbicide No. 3 | 30.0 |
|  | Co-Herbicide - trimexachlor | 15.0 |
|  | Antidote No. 10 | 20.0 |
|  | Calcium dodecyl sulfonate/alkylaryl polyether alcohol blend | 11.0 |
|  | Sodium Lignosulfonate (Marasperse N-22) | 2.0 |
|  | Water | 32.0 |
|  |  | 100.0 |
| H. | Herbicide No. 1 | 28.0 |
|  | Co-Herbicide - EPTC | 20.0 |
|  | Antidote No. 10 | 20.0 |
|  | Calcium dodecylbenzene sulfonate/-polyoxyethylene ethers blend (Atlox ® 3437F) | 5.0 |
|  | Sodium dioctyl sulfosuccinate Aerosol OT | 3.0 |
|  | Water | 24.0 |
|  |  | 100.0 |

VIII. Liquid Concentrates

|  |  | Weight Percent |
|---|---|---|
| A. | Herbicide No. 2 | 20.0 |
|  | Co-Herbicide - EPTC | 15.0 |
|  | Antidote No. 10 | 15.0 |
|  | Xylene | 50.0 |
|  |  | 100.0 |
| B. | Herbicide No. 3 | 30.0 |
|  | Co-Herbicide - butylate | 20.0 |
|  | Antidote No. 10 | 20.0 |
|  | Dimethyl sulfoxide | 30.0 |
|  |  | 100.0 |
| C. | Herbicide No. 1 | 10.0 |
|  | Co-Herbicide - acetochlor | 15.0 |
|  | Antidote No. 9 | 20.0 |
|  | N-methylpyrrolidone | 55.0 |
|  |  | 100.0 |
| D. | Herbicide No. 2 | 15.0 |
|  | Co-Herbicide - metolachlor | 15.0 |

|   |   | Weight Percent |
|---|---|---|
|   | Antidote No. 9 | 10.0 |
|   | Ethoxylated castor oil | 15.0 |
|   | Rhodamine B | 1.5 |
|   | Dimethylformamide | 43.5 |
|   |   | 100.0 |
| E. | Herbicide No. 3 | 10.0 |
|   | Co-Herbicide - butachlor | 10.0 |
|   | Antidote No. 10 | 10.0 |
|   | Atlox 3437F | 5.0 |
|   | Xylene | 65.0 |
|   |   | 100.0 |
| F. | Herbicide No. 4 | 25.0 |
|   | Co-Herbicide - pretilachlor | 15.0 |
|   | Antidote No. 7 | 10.0 |
|   | Xylene | 50.0 |
|   |   | 100.0 |
| G. | Herbicide No. 5 | 27.0 |
|   | Co-Herbicide - metolachlor | 13.0 |
|   | Antidote No. 8 | 22.0 |
|   | Dimethyl sulfoxide | 38.0 |
|   |   | 100.0 |
| H. | Herbicide No. 6 | 25.0 |
|   | Co-Herbicide - butylate | 25.0 |
|   | Antidote No. 9 | 30.0 |
|   | N-methylpyrrolidone | 20.0 |
|   |   | 100.0 |
| I. | Herbicide No. 7 | 15.0 |
|   | Co-Herbicide - acetochlor | 15.0 |
|   | Antidote No. 10 | 20.0 |
|   | Ethoxylated castor oil | 15.0 |
|   | Rhodamine B | 1.5 |
|   | Dimethylformamide | 34.5 |
|   |   | 100.0 |
| J. | Herbicide No. 8 | 15.0 |
|   | Co-Herbicide - alachlor | 15.0 |
|   | Antidote No. 11 | 15.0 |
|   | Atlox 3437F | 5.0 |
|   | Xylene | 30.0 |
|   |   | 100.0 |

IX. Microcapsules

|   |   | Weight Percent |
|---|---|---|
| A. | Herbicide No. 1 encapsulated in a polyurea shell wall | 15.0 |
|   | Reax ® C-21 | 5.0 |
|   | Co-Herbicide - acetochlor | 10.0 |
|   | Antidote No. 10 | 10.0 |
|   | Water | 60.0 |
|   |   | 100.0 |
| B. | Herbicide No. 2 encapsulated in a polyurea shell wall | 15.0 |
|   | Co-Herbicide - acetochlor | 10.0 |
|   | Antidote No. 10 | 10.0 |
|   | Treax, LTM ® | 5.0 |
|   | Water | 60.0 |
|   |   | 100.0 |
| C. | Herbicide No. 2 encapsulated in a polyurea shell wall | 20.0 |
|   | Co-Herbicide - alachlor | 10.0 |
|   | Antidote No. 10 | 10.0 |
|   | Reax C-21 | 3.0 |
|   | Water | 47.0 |
|   |   | 100.0 |
| D. | Herbicide No. 2 encapsulated in a polyurea shell wall | 22.0 |
|   | Co-Herbicide - butachlor | 13.0 |
|   | Antidote No. 18 | 10.0 |
|   | Reax 88 ®B | 2.0 |
|   | Water | 43.9 |
|   |   | 100.0 |
| E. | Herbicide No. 2 encapsulated in a polyurea shell wall | 16.0 |
|   | Co-Herbicide - pretilachlor | 10.0 |
|   | Antidote No. 19 | 15.0 |
|   | Reax ® C-21 | 4.0 |
|   | Water | 55.0 |
|   |   | 100.0 |
| F. | Herbicide No. 2 encapsulated in a polyurea shell wall | 18.0 |
|   | Co-Herbicide - EPTC | 5.0 |
|   | Antidote No. 20 | 15.0 |
|   | Treax, LTM ® | 5.0 |
|   | Water | 57.0 |
|   |   | 100.0 |
| G. | Herbicide No. 1 encapsulated in a polyurea shell wall | 10.0 |
|   | Co-Herbicide - butylate | 10.0 |
|   | Antidote No. 10 | 15.0 |
|   | Reax C-21 | 5.0 |
|   | Water | 60.0 |
|   |   | 100.0 |
| H. | Herbicide No. 1 encapsulated in a polyurea shell wall | 10.0 |
|   | Co-Herbicide - metolachlor | 10.0 |
|   | Antidote No. 10 | 20.0 |
|   | Reax 88 ®B | 2.0 |
|   | Water | 58.0 |
|   |   | 100.0 |

As will be appreciated by those skilled in the art, the practice of this invention comprises the use of the antidotal compounds disclosed and claimed herein with any herbicidally-active azolopyrimidine sulfonamide or derivative compound which may optionally be combined with co-herbicides from many different classes of chemistry. Obviously, the above listings of exemplary compounds is not intended to be exhaustive, but representative. Again, as noted earlier herein, it is expected that not every combination of herbicide and antidote will result in safening of all crops, but it is within the skill of the art to test any given herbicide with an invention antidote in plant screens of any spectrum of plants and note the results.

The foregoing embodiments illustrate that the combinations of herbicide and antidote of this invention are useful in controlling weeds while reducing herbicidal injury to crop plants under greenhouse test conditions.

The herbicide, antidote, or a mixture thereof, may be applied to the plant locus without any adjuvants other than a solvent. These mixtures may be in the form of emulsifiable concentrates, microencapsulates, particulate solids, granules of varying particle size, e.g., water-dispersible or water-soluble granules or larger dry granules, pellets, wettable powders, dusts, solutions, aqueous dispersions, or emulsions.

Examples of suitable adjuvants are finely-divided solid carriers and extenders including talcs, clays, pumice, silica, diatomaceous earth, quartz, Fuller's earth, sulfur, powdered cork, powdered wood, walnut flour, chalk, tobacco dust, charcoal, and the like. Typical liquid diluents include Stoddard's solvent, acetone, methylene chloride, alcohols, glycols, ethyl acetate, benzene, and the like. Liquids and wettable powders usually contain as a conditioning agent one or more surface-active agents in amounts sufficient to make a composition readily dispersible in water or in oil. The term "surface-active agent" includes wetting agents, dispersing agents, suspending agents, and emulsifying agents. Typical surface-active agents are mentioned in U.S. Pat. No. 2,547,724.

Compositions of this invention generally contain from about 5 to 95 parts herbicide-and-antidote, about 1 to 50 parts surface-active agent, and about 4 to 94 parts solvent, all parts being by weight based on the total weight of the composition.

The crop may be protected by treating the crop seed with an effective amount of antidote prior to planting. Generally, smaller amounts of antidote are required to treat such seeds. A weight ratio of as little as 0.6 parts of antidote per 1000 parts of seed may be effective. The amount of antidote utilized in treating the seed may be increased if desired. Generally, however, a weight ratio of antidote-to-seed weight may range from 0.1 to 10.0 parts of antidote per 1000 parts of seed. Since only a very small amount of active antidote is usually required for the seed treatment, the compound preferably is formulated as an organic solution, powder, emulsifiable concentrate, water solution, or flowable formulation, which can be diluted with water by the seed treater for use in seed treating apparatus. Under certain conditions, it may be desirable to dissolve the antidote in an organic solvent or carrier for use as a seed treatment or the pure compound alone may be used under properly controlled conditions.

For antidote seed-coating for antidotes applied to soil in granular or liquid formulations, suitable carriers may be either solids, such as talc, sand, clay, diatomaceous earth, sawdust, calcium carbonate, and the like, or liquids, such as water, kerosene, acetone, benzene, toluene, xylene and the like, in which the active antidote may be either dissolved or dispersed. Emulsifying agents are used to achieve a suitable emulsion if two immiscible liquids are used as a carrier. Wetting agents may also be used to aid in dispersing the active antidote in liquids used as a carrier in which the antidote is not completely soluble. Emulsifying agents and wetting agents are sold under numerous tradenames and trademarks and may be either pure compounds, mixtures of compounds of the same general groups, or they may be mixtures of compounds of different classes. Typical satisfactory surface active agents which may be used are alkali metal higher-alkylarylsulfonates such as sodium dodecylbenzenesulfonate and the sodium salts of alkylnaphthalene-sulfonic acids, fatty alcohol sulfates such as the sodium salts of monoesters of sulfuric acid with n-aliphatic alcohols containing 8–18 carbon atoms, long-chain quaternary ammonium compounds, sodium salts of petroleum-derived alkylsulfonic acids, polyethylene sorbitan monooleate, alkylaryl polyether alcohols, water-soluble lignin sulfonate salts, alkali casein compositions, long-chain alcohols usually containing 10–18 carbon atoms, and condensation products of ethylene oxide with fatty acids, alkylphenols and mercaptans.

The invention herein has been specifically exemplified with the herbicidal compounds identified above as Herbicide Nos. 1–9 as representative of the compounds of Formula I, by the commercial herbicides acetochlor and metolachlor as representative of the co-herbicidal compounds of Formula V and by butylate and EPTC as representative of the thiocarbamate class of herbicides and by various dichloroacetamide antidotes as representative of the compounds according to Formulae II and III, as well as a multiplicity of other antidotes having a variety of chemical structures. It is to be understood that other compounds within the scope of the above formulae and other chemical classes are specifically contemplated as within the scope of this invention. For example, other triazolopyrimidine—and imidazolopyrimidine sulfonamides and their derivatives contemplated herein include the compounds described in the following U.S. patents and EP applications as relevant to the compounds of Formula I:

A. Compounds wherein R is the —SO$_2$N(R$_6$) (R$_7$) moiety A and B are both N and 1. R$_1$ and R$_2$ are discrete, uncombined radicals:
   U.S. Pat. No. 4,889,553
   U.S. Pat. No. 4,959,094

2. R$_1$ and R$_2$ are combined to form substituted and/or unsubstituted bivalent radicals which may contain one or more hetero atoms and saturated, partially saturated or unsaturated bonds:

| | | |
|---|---|---|
| 4,740,233 | 4,854,964 | 5,041,157 |
| 4,741,764 | 4,960,455 | EP Appln. 0 375 076 |
| 4,755,212 | 4,859,231 | EP Appln. 0 343 752 |
| 4,818,273 | 4,795,483 | AU Appln.AU-A-68391 |
| 4,886,883 | 4,910,306 | |
| 4,954,163 | 4,979,981 | |
| 4,959,473 | 5,013,351 | |

B. Compounds analogous to those in A2 above, except that in Formula I only one of A or B is N while the other is CR$_3$ as defined above:
   U.S. Pat. No. 4,731,446
   U.S. Pat. No. 4,799,952
   U.S. Pat. No. 4,892,576

C. Compounds wherein R is the —N(R$_4$)SO$_2$R$_5$ moiety, A and B are both N and R$_1$ and R$_2$ are combined to form a bivalent radical as in A2 above:

| | |
|---|---|
| 4,638,075 | 4,822,404 |
| 4,650,892 | 4,685,958 |

The above specifically mentioned herbicidal compounds used as co-herbicides herein are intended merely as exemplary of the classes of herbicides which they represent. However, it is expressly contemplated that many other herbicidal compounds analogous to those represented herein having a variety of equivalent radicals substituted on the central nucleus may similarly be safened to various crop plants to a greater or lesser extent with the antidotal compounds of this invention. For example, other α-haloacetamide and α-haloacet-anilide compounds useful as herbicides are described in U.S. Pat. Nos. 3,442,945, 3,547,620, 3,574,746, 3,586,496, 3,830,841, 3,901,768, 4,249,935, 4,319,918, 4,517,011, 4,601,745, 4,657,579 and 4,666,502 and Australian Patent No. AU-A1-18044/88.

Herbicidally-useful thiocarbamate compounds are described in U.S. Pat. Nos. 2,913,327, 3,330,643 and 3,330,821.

Other herbicidal pyridine compounds are described in U.S. Pat. No. 4,692,184 and copending U.S. Ser. No. 07/134,231 and U.S. Pat. No. 4,826,532, both of common assignment herewith.

Herbicidally-useful heterocycyl phenyl ethers (especially pyrazolyl aryl ethers) are described, e.g., in U.S. Pat. No. 4,298,749.

Herbicidal diphenyl ethers and nitrophenyl ethers include 2,4-dichlorophenyl 4'-nitrophenyl ether ("nitrofen"), 2-chloro-1-(3'-ethoxy-4'-nitrophenoxy)-4- trifluoromethylbenzene ("Oxyfluorfen"), 2',4'-dichlorophenyl 3-methoxy-4-nitrophenyl ether ("Chlormethoxynil"), methyl 2-[4'-(2",4"-dichlorophenoxy)-phenoxy]-propionate, N-(2'-phenoxyethyl)-2-[5'-(2"-chloro-4"-trifluoromethylphenoxy)-phenoxy]-propionamide, 2-methoxyethyl 2-[nitro-5-(2-chloro-4-trifluoromethylphenoxy)-phenoxyl-propionate and 2-chloro-4-trifluoromethylphenyl 3'-oxazolin-2'-yl-4'-nitrophenylether.

Another generic class of agrichemically-important herbicidal compounds specifically contemplated for use as co-herbicidal compounds in combination with the antidotal compounds of this invention are the ureas and sulfonylurea derivatives. Important herbicidal ureas include 1-(benzothiazol-2-yl)-1,3-dimethylurea; phenylureas, for example: 3-(3-chloro-p-tolyl)-1,1-dimethylurea ("chlorotoluron"), 1,1-dimethyl-3-(α,α,α-trifluoro-m-tolyl) urea ("fluometuron"), 3-(4-bromo-3-chlorophenyl)-methoxy-1-methylurea ("chlorbromuron"), 3-(4-bromophenyl)-1-methoxy-1-methylurea ("metobromuron"), 3-(3,4-dichlorophenyl)-1-methoxy-1-methylurea ("linuron"), 3-(4-chlorophenyl)-1-methoxy-1-methylurea ("monolinuron"), 3-(3,4-dichlorophenyl)-1,1-dimethylurea ("diuron"), 3-(4-chlorophenyl)-1,1-dimethylurea ("monuron") and 3-(3-chloro-4-methoxyphenyl)-1,1-dimethylurea ("metoxuron");

Important herbicidal sulfonylureas and sulfonamides specifically contemplated as useful as co-herbicides in compositions with the antidotal compounds of this invention include those disclosed in the following patents: U.S. Pat. Nos. 4,383,113, 4,127,405, 4,479,821, 4,481,029, 4,514,212, 4,420,325, 4,638,004, 4,675,046, 4,681,620, 4,741,760, 4,723,123, 4,411,690, 4,718,937, 4,620,868, 4,668,277, 4,592,776, 4,666,508, 4,696,695, 4,731,446, 4,678,498, 4,786,314, 4,889,550, 4,931,081 and 4,668,279; EP Numbers 084224, 173312, 87780, 190105, 256396, 264021, 264672, 142152, 244847, 176304, 177163, 187470, 187489, 184385, 232067, 234352, 189069, 224842, 249938, 246984 and 282613, and German Offen. DE 3,618,004.

Among other herbicidal sulfonylureas disclosed in one or more of the above patents which are of particular interest are mentioned the species N-[(4-methoxy-6-methylpyrimidin-2-yl)aminocarbonyl]-3-chloro-4-methoxy-carbonyl-1-methylpyrazole-5-sulfonamide; N-[(4-methoxy-6-methylpyrimidin-2-yl)aminocarbonyl]-3-chloro-4-ethoxycarbonyl-1-methylpyrazole-5-sulfonamide; N-[(4,6-dimethoxypyrimidin-2-yl)aminocarbonyl]-3-chloro-4-ethoxycarbonyl-1-methylpyrazole-5-sulfonamide; N-[(4-methoxy-6-methylpyrimidin-2-yl)aminocarbonyl]-3-bromo-4-ethoxycarbonyl-1-methylpyrazole-5-sulfonamide; N-[(4,6-dimethoxypyrimidin-2-yl)aminocarbonyl]-3-bromo-4-ethoxy-carbonyl-1-methylpyrazole-5-sulfonamide and N-(methoxy-carbonyl-1-phenyl sulfonyl-N'-(bis-difluoromethoxy-pyrimidin-2-yl)urea.

Other herbicidal imidazolinone or imidazolidi-none or -dione compounds within the purview of this invention as co-herbicides which may be safened for use in various crops include the compounds disclosed in the following exemplary publications: EP Numbers 041623, 133310, 198552, 216360 and 298029; JA 1109-790, JA 1197-580A, J6 1183-272A and J6 3196-750A; and Australian published Application No. AU 8661-073A, GB 2 172 886A and U.S. Pat. Nos. 4,188,487, 4,297,128, 4,562,257, 4,554,013, 4,647,301, 4,638,068, 4,650,514, 4,709,036, 4,749,403, 4,749,404, 4,776,619, 4,798,619 and 4,741,767.

Still other classes of herbicidal compounds contemplated for combination with azolopyrimidine sulfonamide derivatives and the antidotes of this invention include the following representative species:

Triazines and triazinones: 2,4-bis-(isopropylamino)-6-methylthio-1,3,5-triazine ("prometryn"), 2,4-bis-(ethylamino)-6-methylthio-1,3,5-triazine ("simetryn"), 2-(1',2'-dimethylpropylamino)-4-ethylamino-6-methyl-thio-1,3,5-triazine ("dimethametryn"), 2-(chloro-4,6-bis-(ethylamino)-1,3,5-triazine ("simazine"), 2-tert-butyl-amino-4-chloro-6-ethylamino-1,3,5-triazine ("terbuthylazine"), 2-tert-butylamino-4-ethylamino-6-methoxy-1,3,5-triazine ("terbumeton"), 2-tertbutylamino-4-ethylamino-6-methylthio-1,3,5-triazine ("terbutryn"), 2-ethylamino-4-isopropylamino-6-methylthio-1,3,5-triazine ("ametryn") and 3,4-bis-(methylamino)-6-tert-butyl-4,4-dihydro-1,2,4-triazin-5-one.

Oxadiazolones: 5-tert-butyl-3-(2',4'-dichloro-5'-isopropoxyphenyl)-1,3,4-oxadiazol-2-one ("Oxadiazon").

Phosphates: S-2-methylpiperidinocarbonylmethyl O,O-dipropyl phosphorodithioate ("Piperophos").

Pyrazoles: 1,3-dimethyl-4-(2',4'-dichlorobenzolyl)-5-(4'-tolylsulfonyloxy)-pyrazole; aryl- and heterocyclic-substituted pyrazoles, e.g., as exemplified in EP No. 0361114; Japanese Kokai No. JP 50137061 and U.S. Pat. No. 4,008,249. Preferred species of such substituted-pyrazole compounds include 4-chloro-3-(4-chloro-2-fluoro-5-(2-propynyloxy)phenyl)-1-methyl-5-(methylsulfonyl)-1H pyrazole and analogs thereof, e.g., where the substituent in the 5-position of the pyrazole ring is a haloalkyl radical, preferably $CF_3$.

Also α-(phenoxyphenoxy)-propionic acid derivatives and α-pyridyl-2-oxyphenoxy)-propionic acid derivatives.

Other herbicidal compounds useful as co-herbicides with the azolopyrimidine sulfonamide compounds of Formula I include aromatic and heterocyclic di- and triketones exemplified in U.S. Pat. Nos. 4,797,147, 4,853,028, 4,854,966, 4,855,477, 4,938,796 and 4,869,748.

Still other co-herbicidal compounds contemplated herein are pyrrolidinones, e.g., the 1-phenyl-3-carboxyamidopyrrolidinones disclosed in U.S. Pat. No. 4,874,422, and the 1-phenyl-4-haloalkylpyrrolidones disclosed in U.S. Pat. No. 4,515,627, etc.

Still other herbicidal compounds useful as co-herbicides herein include benzoic acid derivatives of the type exemplified by 5-(2'-chloro-4'-trifluoromethylphenoxy)-2-nitrobenzoic acid ("Acifluorfen"), 2,6-dichlorobenzonitrile ("dichlobenil"), 3,6-dichloro-2-methoxybenzoic acid ("dicamba"), etc. and compounds disclosed in U.S Pat. Nos. 3,013,054, 3,027,248 and 3,979,437, etc.

In addition to the antidotal compounds exemplified herein, other representative antidotal compounds according to Formula II or other structure expressly contemplated herein are disclosed in various patents, e.g., U.S. Pat. Nos. 3,959,304, 4,072,688, 4,137,070, 4,124,372, 4,124,376, 4,483,706, 4,636,244, 4,033,756, 4,493,726, 4,708,735, 4,256,481, 4,199,506, 4,251,261, 4,070,389, 4,231,783, 4,269,775, 4,152,137, 4,755,218, 4,964,893, 4,623,727, 4,822,884, 4,851,031, 4,902,340, 4,749,406, 4,758,264, 4,785,105, 4,785,106, 4,294,764, 5,028,256 and 5,037,468; PCT Appln. Nos. WO 91/07874 and WO 91/08202; EP Nos. 159,287, 159,290, 258,184, 94,349, 2,121,403, 0253291, 0007588, 0190105, 0229649, 0430004 and 16618; W. German Patent Application Nos. 28 28 222, 28 28 293.1, and 29 30 450.5; South African Patent No. 82/7681 and PRC Application No. 102 879-87.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

We claim:

1. Composition comprising a herbicidally-effective amount of 5-methyl-N-(2,6-difluorophenyl)-1,2,4-triazolo[1,5-a]pyrimidine-2-sulfonamide and an antidotally-effective amount of oxazolidine, 3-(dichloroacetyl)-5-(2-furanyl)-2,2-dimethyl-.

2. Composition comprising
   (a) a herbicidally-effective amount which is damaging to crops of a compound according to Formula I or agriculturally acceptable salts thereof:

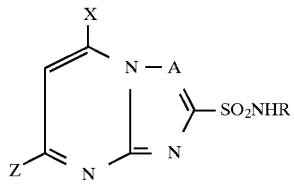

wherein
   A is N or C(Cl);
   X is H or $C_{1-4}$ alkyl or alkoxy;
   Z is $C_{1-4}$ alkyl or haloalkyl;
   R is phenyl substituted in the ortho positions independently with H, chloro, fluoro, nitro, —$OCH_3$ or —$CF_3$ groups and in the meta positions with H or $CH_3$ groups and
   (b) an antidotally-effective amount of one or more of the compounds:
   4-Pentenenitrile, 2-methyl-2-[(4-methylphenyl)thio],
   Acetic acid, (diphenylmethoxy)-, methyl ester,
   Benzenemethanamine, N-[4-(dichloromethylene)-1,3-dithiolan-2-ylidene]-α-methyl-, hydrochloride,
   Phosphorothioic acid, O,O-diethyl-O-(3-methylphenyl) ester,
   5-Thiazolecarboxylic acid, 2-chloro-4-(trifluoromethyl)-, (phenylmethyl ester),
   Pyrimidine, 4,6-dichloro-2-phenyl-,
   1H, 3H-Naphtho[1,8-cd]pyran-1,3-dione,
   Benzeneacetonitrile, α-{[(1,3-dioxolan-2-yl)-methoxy]imino}-,
   Acetamide, N,N-Bis(2-propenyl)-α,α-dichloro,
   Oxazolidine, 3-(dichloroacetyl)-5-(2-furanyl)-2,2-dimethyl-,
   Cis/Trans-piperazine, 1,4-bis(dichloroacetyl)-2,5-dimethyl,
   1-Oxa-4-azaspiro[4.5]decane, 4-(dichloroacetyl)-,
   Oxazolidine, 3-(dichloroacetyl)-2,2,5-trimethyl,
   Oxazolidine, 3-(dichloroacetyl)-2,2-dimethyl,
   Acetamide, 2,2-dichloro-N-(1,3-dioxolan-2-yl-methyl)-N-2-propenyl,
   Ethanone, 2,2-dichloro-1-(1,2,3,4-tetrahydro-1-methyl-2-isoquinolinyl,
   1,3-Dioxolane, 2-(dichloromethyl)-2-methyl-,
   5-Chloro-8-(cyanomethoxy)quinoline,
   1-Methylhexyl-2-(5-chloro-8-quinolinoxy)acetate,
   O-(Methoxycarbonyl)-2-(8-quinolinoxy)-acetamide oxime,
   4-(Dichloroacetyl)-2,3-dihydro-3-methyl-2H-1,4-benzoxazine.

3. Composition according to claim 2 wherein said compound according to Formula I is
   5,7-Dimethyl-N-(2,6-dichloro-3-methylphenyl)-1,2,4-triazolo[1,5-a]pyrimidine-2-sulfonamide,
   5-Methyl-N-(2,6-difluorophenyl)-1,2,4-triazolo-[1,5-a]-pyrimidine-2-sulfonamide,
   5,7-Dimethyl-N-(2-nitrophenyl)-1,2,4-triazolo-[1,5-a]-pyrimidine-2-sulfonamide,
   5,7-Dimethyl-N-[2-methoxy-6-(trifluoromethyl)-phenyl]-1,2,4-triazolo-[1,5-a]-pyrimidine-2-sulfonamide,
   5-Methyl-7-ethoxy-N-(2,6-dichloro-3-methyl-phenyl)-1,2,4-triazolo-[1,5-a]-pyrimidine-2-sulfonamide,
   N-(2,6-Difluorophenyl)-3-chloro-4,6-dimethylimidazolo-[1,2-a]-pyrimidine-2-sulfonamide,
   5-Fluoromethyl-7-methoxy-N-(2,6-dichlorophenyl)-1,2,4-triazolo-[1,5-a]-pyrimidine-2-sulfonamide.

4. Composition according to claim 3 wherein said antidotal is
   Oxazolidine, 3-(dichloroacetyl)-2,2,5-trimethyl-,
   Oxazolidine, 3-(dichloroacetyl)-2,2-dimethyl-5-(2-furanyl)-.

5. Composition according to claim 4 wherein said compound of Formula I is 5-methyl-N-(2,6-difluorophenyl)-1,2,4-triazolo[1,5-a]-pyrimidine-2-sulfonamide.

6. Composition according to claim 3 wherein said antidotal compound is
   N,N-diallyl dichloroacetamide,
   Oxazolidine, 3-(dichloroacetyl)-2,2,5-trimethyl-,
   Oxazolidine, 3-(dichloroacetyl)-5-(2-furanyl-2,2-dimethyl-,
   4-(Dichloroacetyl)-1-oxa-4-azaspiro-(4,5)-decane,
   Acetamide, 2,2-dichloro-N-(1,3-dioxolany-2-yl-methyl)-N-2-propenyl,
   5-Chloro-8-(cyanomethoxy)quinoline,
   1-Methylhexyl-2-(5-chloro-8-quinolinoxy) acetate or
   O-(Methoxycarbonyl)-2-(8-quinolinoxy) acetamide oxime.

7. Method for reducing phytotoxicity to crop plants due to herbicidal compounds according to Formula I

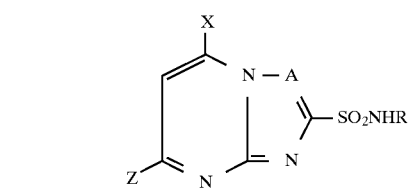

wherein
   A is N or C(Cl);
   X is H or $C_{1-4}$ alkyl or alkoxy;
   Z is $C_{1-4}$ alkyl or haloalkyl;
   R is phenyl substituted in the ortho positions independently with H, chloro, fluoro, nitro, —$OCH_3$ or —$CF_3$ groups and in the meta positions with H or $CH_3$ groups which comprises applying to the locus or seeds of the crop an antidotally-effective amount which is damaging to said crop one or more of the compounds
   4-Pentenenitrile, 2-methyl-2-[(4-methylphenyl)thio],
   Acetic acid, (diphenylmethoxy)-, methyl ester,
   Benzenemethanamine, N-[4-(dichloromethylene)-1,3-dithiolan-2-ylidene]-α-methyl-, hydrochloride,
   Phosphorothioic acid, O,O-diethyl-O-(3-methylphenyl) ester,
   5-Thiazolecarboxylic acid, 2-chloro-4-(trifluoromethyl)-, (phenylmethyl ester),
   Pyrimidine, 4,6-dichloro-2-phenyl-, 1H, 3H-Naphtho[1,8-cd]pyran-1,3-dione, Benzeneacetonitrile, α-{[(1,3-dioxolan-2-yl)-methoxy]imino}-, Acetamide, N,N-Bis(2-propenyl)-α,α-dichloro, Oxazolidine, 3-(dichloroacetyl)-5-(2-furanyl)-2,2-dimethyl-, Cis/Trans-piperazine, 1,4-bis(dichloroacetyl)-2,5-dimethyl, 1-Oxa-4-azaspiro[4.5]decane, 4-(dichloroacetyl)-, Oxazolidine, 3-(dichloroacetyl)-2,2,5-trimethyl, Oxazolidine, 3-(dichloroacetyl)-2,2-dimethyl, Acetamide, 2,2-dichloro-N-(1,3-dioxolan-2-yl-methyl)-N-2-propenyl, Ethanone, 2,2-dichloro-1-(1,2,3,4-tetrahydro-1-methyl-2-isoquinolinyl, 1,3-Dioxolane, 2-(dichloromethyl)-2-methyl-, 5-Chloro-8-(cyanomethoxy)quinoline, 1-Methylhexyl-2-(5-chloro-8-quinolinoxy)acetate, O-(Methoxycarbonyl)-2-(8-quinolinoxy)-acetamide oxime, 4-(Dichloroacetyl)-2,3-dihydro-3-methyl-2H-1,4-benzoxazine.

8. Method according to claim 7 wherein said compounds of Formula I are 5,7-Dimethyl-N-(2,6-dichloro-3-methylphenyl)-1,2,4-triazolo[1,5-a]pyrimidine-2-sulfonamide, 5-Methyl-N-(2,6-difluorophenyl)-1,2,4-triazolo-[1,5-a]-pyrimidine-2-sulfonamide, 5,7-Dimethyl-N-(2-nitrophenyl)-1,2,4-triazolo-[1,5-a]-pyrimidine-2-sulfonamide, 5,7-Dimethyl-N-[2-methoxy-6-(trifluoromethyl)-phenyl]-1,2,4-triazolo-[1,5-a]-pyrimidine-2-sulfonamide, 5-Methyl-7-ethoxy-N-(2,6-dichloro-3-methyl-phenyl)-1,2,4-triazolo-[1,5-a]-pyrimidine-2-sulfonamide, N-(2,6-Difluorophenyl)-3-chloro-4,6-dimethylimidazolo-[1,2-a]-pyrimidine-2-sulfonamide, 5-Fluoromethyl-7-methoxy-N-(2,6-dichlorophenyl)-1,2,4-triazolo-[1,5-a]-pyrimidine-2-sulfonamide.

9. Method according to claim 8 wherein said antidotal compound is

Oxazolidine, 3-(dichloroacetyl)-2,2,5-trimethyl-,

Oxazolidine, 3-(dichloroacetyl)-2,2-dimethyl-5-(2-furanyl)-, 4-(dichloroacetyl)-1-oxa-4-azaspiro-(4,5)-decane.

10. Method according to claim 9 wherein said compound of Formula I is 5-methyl-N-(2,6-difluorophenyl)-1,2,4-triazolo[1,5-a]-pyrimidine-2-sulfonamide.

11. Method according to claim 8 wherein said compound of Formula I is 5-methyl-N-(2,6-difluorophenyl)-1,2,4-triazolo[1,5-a]pyrimidine-2-sulfonamide and said antidotal compound is oxazolidine, 3-(dichloroacetyl)-5-(2-furanyl)-2,2-dimethyl-.

12. Method according to claim 8 wherein said crop is corn, wheat, rice, sorghum, soybeans or cotton.

13. Method according to claim 7 wherein said antidotal compound of component (b) is N,N-diallyl dichloroacetamide, Oxazolidine, 3-(dichloroacetyl)-2,2,5-trimethyl-, Oxazolidine, 3-(dichloroacetyl)-5-(2-furanyl-2,2-dimethyl-, 4-(Dichloroacetyl)-1-oxa-4-azaspiro-(4,5)-decane, Acetamide, 2,2-dichloro-N-(1,3-dioxolany-2-yl-methyl)-N-2-propenyl, 5-Chloro-8-(cyanomethoxy)quinoline, 1-Methylhexyl-2-(5-chloro-8-quinolinoxy) acetate or O-(Methoxycarbonyl)-2-(8-quinolinoxy) acetamide oxime.

* * * * *

UNITED STATES PATENT AND TRADEMARK OFFICE
CERTIFICATE OF CORRECTION

PATENT NO.   :   5,880,066

DATED        :   March 9, 1999

INVENTOR(S)  :   Barbara Heard Wells/Harrison Ross Hakes/David James Mayonado/
                 John Paul Chupp It is certified that error appears in the above-identified patent and that said Letters Patent is hereby corrected as shown below:

In claim 2(b), column 81, line 61, after "oxime," insert --or--.

In claim 4, column 82, line 18, after "furanyl)-," insert --4-(dichloroacetyl)-1-oxa-4-azaspiro-(4,5)-decane.--.

In claim 8, column 84, line 2, after "[1,2-a]-pyrimidine-2-sulfonamide," insert --or--.

In claim 9, column 84, line 10, after "furanyl)-," insert --or--.

Signed and Sealed this

Twenty-ninth Day of February, 2000

Attest:

Q. TODD DICKINSON

Attesting Officer

Commissioner of Patents and Trademarks